(12) United States Patent
Taylor et al.

(10) Patent No.: US 11,414,644 B2
(45) Date of Patent: *Aug. 16, 2022

(54) METHODS OF RECELLULARIZING A TISSUE OR ORGAN FOR IMPROVED TRANSPLANTABILITY

(71) Applicant: Regents of the University of Minnesota, Minneapolis, MN (US)

(72) Inventors: Doris Taylor, St. Paul, MN (US); Stefan M. Kren, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/260,997

(22) Filed: Jan. 29, 2019

(65) Prior Publication Data

US 2019/0284523 A1 Sep. 19, 2019

Related U.S. Application Data

(63) Continuation of application No. 13/820,079, filed as application No. PCT/US2011/050266 on Sep. 1, 2011, now Pat. No. 10,233,420.

(60) Provisional application No. 61/379,073, filed on Sep. 1, 2010.

(51) Int. Cl.
*C12N 5/00* (2006.01)
*A61L 27/36* (2006.01)
*A61L 27/38* (2006.01)

(52) U.S. Cl.
CPC ........ *C12N 5/0062* (2013.01); *A61L 27/3604* (2013.01); *A61L 27/3808* (2013.01)

(58) Field of Classification Search
None
See application file for complete search history.

(56) References Cited

U.S. PATENT DOCUMENTS

| 3,545,221 | A  | 12/1970 | Koski et al. |
| 3,639,084 | A  | 2/1972  | Goldhaber |
| 4,083,066 | A  | 4/1978  | Schmitz et al. |
| 4,801,299 | A  | 1/1989  | Brendel et al. |
| 5,336,616 | A  | 8/1994  | Livesey et al. |
| 6,376,244 | B1 | 4/2002  | Atala |
| 6,379,963 | B2 | 4/2002  | Haverich et al. |
| 6,416,995 | B1 | 7/2002  | Wolfinbarger |
| 6,432,712 | B1 | 8/2002  | Wolfinbarger, Jr. |
| 6,479,064 | B1 | 11/2002 | Atala |
| 6,689,161 | B2 | 2/2004  | Chen |

(Continued)

FOREIGN PATENT DOCUMENTS

| AU | 2006282783 A1 | 3/2007 |
| AU | 2006282783 B2 | 9/2013 |

(Continued)

OTHER PUBLICATIONS

"U.S. Appl. No. 12/064,613, Response filed Apr. 5, 2013 to Final Office Action dated Feb. 7, 2013", 11 pgs.

(Continued)

*Primary Examiner* — Erin M. Bowers
(74) *Attorney, Agent, or Firm* — Schwegman Lundberg & Woessner, P.A.

(57) ABSTRACT

Described herein are methods of recellularizing an organ or tissue matrix.

21 Claims, 12 Drawing Sheets

(56) References Cited

U.S. PATENT DOCUMENTS

| | | |
|---|---|---|
| 6,749,064 B1 | 6/2004 | Alrey |
| 6,753,181 B2 | 6/2004 | Atala |
| 6,960,427 B2 | 11/2005 | Haverich et al. |
| 6,962,814 B2 | 11/2005 | Mitchell et al. |
| 7,311,904 B2 | 12/2007 | Hariri |
| 7,354,749 B2 | 4/2008 | Fisher et al. |
| 8,470,520 B2 | 6/2013 | Ott et al. |
| 9,290,738 B2 | 3/2016 | Ross et al. |
| 9,334,479 B2 | 5/2016 | Herrera Sanchez et al. |
| 9,974,814 B2 | 5/2018 | Katane et al. |
| 10,220,056 B2 | 3/2019 | Ott et al. |
| 10,233,420 B2 | 3/2019 | Taylor et al. |
| 10,441,609 B2 | 10/2019 | Ott et al. |
| 2001/0049138 A1 | 12/2001 | Dennis et al. |
| 2002/0081728 A1 | 6/2002 | Haverich et al. |
| 2003/0087428 A1 | 5/2003 | Wolfinbarger, Jr. et al. |
| 2003/0096407 A1 | 5/2003 | Atala et al. |
| 2003/0124099 A1 | 7/2003 | Atala et al. |
| 2003/0215945 A1 | 11/2003 | Atala |
| 2003/0228692 A1 | 12/2003 | Goldstein et al. |
| 2004/0176855 A1 | 9/2004 | Badylak |
| 2004/0187877 A1 | 9/2004 | Badylak et al. |
| 2005/0084512 A1 | 4/2005 | Denizeau et al. |
| 2005/0130300 A1 | 6/2005 | Shimada et al. |
| 2005/0249816 A1 | 11/2005 | Atala et al. |
| 2007/0002061 A1 | 1/2007 | Sherley et al. |
| 2007/0059293 A1 | 3/2007 | Atala |
| 2008/0058956 A1 | 3/2008 | Badylak |
| 2009/0169525 A1 | 7/2009 | Anversa et al. |
| 2009/0202977 A1* | 8/2009 | Ott .................. C12N 5/0602 435/1.2 |
| 2010/0093066 A1 | 4/2010 | Taylor et al. |
| 2011/0059152 A1 | 3/2011 | Atala |
| 2012/0064537 A1 | 3/2012 | Ross |
| 2012/0183944 A1 | 7/2012 | Taylor et al. |
| 2013/0109088 A1 | 5/2013 | Ott et al. |
| 2013/0156744 A1 | 6/2013 | Taylor et al. |
| 2013/0344599 A1 | 12/2013 | Ott et al. |
| 2016/0030637 A1 | 2/2016 | Ross et al. |
| 2016/0030638 A1 | 2/2016 | Ross et al. |
| 2018/0064848 A1 | 3/2018 | Ross et al. |
| 2019/0343877 A1 | 11/2019 | Ott et al. |
| 2020/0222456 A1 | 7/2020 | Ott et al. |
| 2022/0062349 A1 | 3/2022 | Taylor et al. |

FOREIGN PATENT DOCUMENTS

| | | |
|---|---|---|
| AU | 2013224686 B2 | 6/2015 |
| CA | 2757457 | 5/2018 |
| CN | 1615162 A | 5/2005 |
| CN | 101066477 A | 11/2007 |
| CN | 101272815 A | 9/2008 |
| CN | 101272815 B | 9/2012 |
| CN | 102861359 A | 1/2013 |
| CN | 103458935 B | 8/2016 |
| EP | 1246903 A1 | 1/2008 |
| EP | 2431063 A2 | 3/2012 |
| EP | 1928519 B1 | 4/2012 |
| EP | 2431063 B1 | 6/2015 |
| EP | 2965769 A1 | 1/2016 |
| EP | 2611472 B1 | 2/2016 |
| EP | 2965769 B1 | 12/2018 |
| ES | 2384721 T3 | 7/2012 |
| HK | 1220646 A1 | 5/2017 |
| JP | 5516016 A | 2/1980 |
| JP | 55016016 A | 4/1980 |
| JP | 06261933 A | 9/1994 |
| JP | 1176400 A | 3/1999 |
| JP | H1176400 A | 3/1999 |
| JP | 2000004870 A | 1/2000 |
| JP | 2004167236 A | 6/2004 |
| JP | 2005509495 A | 4/2005 |
| JP | 2007222391 A | 9/2007 |
| JP | 2008541717 A | 11/2008 |
| JP | 2009505752 A | 2/2009 |
| JP | 2013536738 A | 6/2013 |
| JP | 2015094591 A | 5/2015 |
| JP | 2015164549 A | 9/2015 |
| JP | 2016039903 A | 3/2016 |
| JP | 2017038948 A | 2/2017 |
| JP | 6089062 B2 | 3/2017 |
| JP | 2017-195900 A | 11/2017 |
| JP | 2019-088910 A | 6/2019 |
| KR | 10-1900116 B1 | 9/2018 |
| MX | 343363 B | 11/2016 |
| MX | 350338 B | 9/2017 |
| RU | 2463081 C2 | 10/2012 |
| RU | 2011143730 A | 5/2013 |
| RU | 2611361 C2 | 2/2017 |
| RU | 2635478 C2 | 11/2017 |
| SG | 10201603074Q | 11/2020 |
| WO | WO-9608213 A1 | 3/1996 |
| WO | WO-0148153 A1 | 7/2001 |
| WO | WO-0149210 A1 | 7/2001 |
| WO | WO-0224244 A2 | 3/2002 |
| WO | WO-2002024244 A2 | 3/2002 |
| WO | WO-0240630 A2 | 5/2002 |
| WO | WO-0249681 A1 | 6/2002 |
| WO | WO-2002049681 A1 | 6/2002 |
| WO | WO-02063962 A1 | 8/2002 |
| WO | WO-2002063962 A1 | 8/2002 |
| WO | WO-03039610 A1 | 5/2003 |
| WO | WO-03043674 A1 | 5/2003 |
| WO | WO-2003039610 A1 | 5/2003 |
| WO | WO-2003043674 A1 | 5/2003 |
| WO | WO-03087428 A1 | 10/2003 |
| WO | WO-2004054571 A1 | 7/2004 |
| WO | WO-2004080501 A1 | 9/2004 |
| WO | WO-2004100832 A1 | 11/2004 |
| WO | WO-2005118014 A2 | 12/2005 |
| WO | WO-2006033415 A1 | 3/2006 |
| WO | WO-2006/126236 A1 | 11/2006 |
| WO | WO-2006122533 A2 | 11/2006 |
| WO | WO-2007025233 A1 | 3/2007 |
| WO | WO-2010120539 A1 | 10/2010 |
| WO | WO-2010120539 A2 | 10/2010 |
| WO | WO-2010120539 A3 | 2/2011 |
| WO | WO-2011031484 A2 | 3/2011 |
| WO | WO-2012031162 A1 | 3/2012 |

OTHER PUBLICATIONS

"U.S. Appl. No. 12/064,613, Declaration of Dr. Doris Taylor filed Jan. 26, 2012", 4 pgs.

"U.S. Appl. No. 12/064,613, Declaration of Dr. Jeffrey Ross filed Mar. 4, 2013", 8 pgs.

"U.S. Appl. No. 12/064,613, Examiner Interview Summary dated Mar. 7, 2013", 3 pgs.

"U.S. Appl. No. 12/064,613, Examiner Interview Summary dated Apr. 5, 2013", 4 pgs.

"U.S. Appl. No. 12/064,613, Examiner Interview Summary dated Jun. 20, 2012", 3 pgs.

"U.S. Appl. No. 12/064,613, Examiner Interview Summary dated Jul. 13, 2012", 3 pgs.

"U.S. Appl. No. 12/064,613, Examiner Interview Summary dated Jul. 18, 2012", 3 pgs.

"U.S. Appl. No. 12/064,613, Final Office Action dated Feb. 7, 2013", 16 pgs.

"U.S. Appl. No. 12/064,613, Final Office Action dated Apr. 6, 2012", 10 pgs.

"U.S. Appl. No. 12/064,613, Non Final Office Action dated Aug. 30, 2012", 18 pgs.

"U.S. Appl. No. 12/064,613, Notice of Allowance dated May 1, 2013", 11 pgs.

"U.S. Appl. No. 12/064,613, Preliminary Amendment filed Feb. 22, 2008", 8 pgs.

"U.S. Appl. No. 12/064,613, Response filed Jan. 27, 2012 to Non Final Office Action dated Sep. 29, 2011", 10 pgs.

"U.S. Appl. No. 12/064,613, Response filed Jul. 16, 2012 to Final Office Action dated Apr. 6, 2012", 12 pgs.

(56) References Cited

OTHER PUBLICATIONS

"U.S. Appl. No. 12/064,613, Response filed Jul. 21, 2011 to Restriction Requirement dated Jun. 29, 2011", 9 pgs.
"U.S. Appl. No. 12/064,613, Response filed Dec. 4, 2012 to Non Final Office Action dated Aug. 30, 2012", 11 pgs.
"U.S. Appl. No. 12/064,613, Restriction Requirement dated Jun. 29, 2011", 8 pgs.
"U.S. Appl. No. 12/547,021, Final Office Action dated May 14, 2012", 11 pgs.
"U.S. Appl. No. 12/547,021, Non Final Office Action dated Dec. 14, 2011", 11 pgs.
"U.S. Appl. No. 12/547,021, Response filed Mar. 14, 2012 to Non Final Office Action dated Dec. 14, 2011", 9 pgs.
"U.S. Appl. No. 13/262,286, Advisory Action dated Jun. 27, 2017", 3 pgs.
"U.S. Appl. No. 13/262,286, Final Office Action dated Jun. 11, 2015", 6 pgs.
"U.S. Appl. No. 13/262,286, Non Final Office Action dated Mar. 29, 2018", 10 pgs.
"U.S. Appl. No. 13/262,286, Non Final Office Action dated Jun. 10, 2016", 8 pgs.
"U.S. Appl. No. 13/262,286, Non Final Office Action dated Oct. 9, 2014", 7 pgs.
"U.S. Appl. No. 13/262,286, Preliminary Amendment filed Sep. 30, 2011", 3 pgs.
"U.S. Appl. No. 13/262,286, Response filed Feb. 14, 2014 to Final Office Action dated Aug. 14, 2013", 7 pgs.
"U.S. Appl. No. 13/262,286, Response filed Mar. 9, 2015 to Non Final Office Action dated Oct. 9, 2014", 7 pgs.
"U.S. Appl. No. 13/262,286, Response filed Jun. 9, 2017 to Final Office Action dated Mar. 9, 2017", 8 pgs.
"U.S. Appl. No. 13/262,286, Response filed Jun. 10, 2013 to Non Final Office Action dated Dec. 14, 2012", 7 pgs.
"U.S. Appl. No. 13/262,286, Response filed Nov. 30, 2012 to Restriction Requirement dated Oct. 30, 2012", 8 pgs.
"U.S. Appl. No. 13/262,286, Response filed Dec. 7, 2015 to Final Office Action dated Jun. 11, 2015", 8 pgs.
"U.S. Appl. No. 13/262,286, Response filed Dec. 8, 2016 to Non Final Office Action dated Jun. 10, 2016", 7 pgs.
"U.S. Appl. No. 13/262,286, Restriction Requirement dated Oct. 30, 2012", 8 pgs.
"U.S. Appl. No. 13/725,030, Advisory Action dated Jun. 5, 2014", 3 pgs.
"U.S. Appl. No. 13/725,030, Examiner Interview Summary dated Jan. 22, 2015", 4 pgs.
"U.S. Appl. No. 13/725,030, Examiner Interview Summary dated Jan. 29, 2016", 5 pgs.
"U.S. Appl. No. 13/725,030, Examiner Interview Summary dated Mar. 6, 2015", 3 pgs.
"U.S. Appl. No. 13/725,030, Examiner Interview Summary dated Jun. 29, 2015", 3 pgs.
"U.S. Appl. No. 13/725,030, Final Office Action dated Mar. 17, 2014", 14 pgs.
"U.S. Appl. No. 13/725,030, Final Office Action dated May 19, 2015", 23 pgs.
"U.S. Appl. No. 13/725,030, Final Office Action dated Jun. 23, 2016", 22 pgs.
"U.S. Appl. No. 13/725,030, Final Office Action dated Sep. 13, 2017", 20 pgs.
"U.S. Appl. No. 13/725,030, Non Final Office Action dated Jan. 6, 2017", 28 pgs.
"U.S. Appl. No. 13/725,030, Non Final Office Action dated Jan. 29, 2018", 19 pgs.
"U.S. Appl. No. 13/725,030, Non Final Office Action dated Jul. 5, 2013", 12 pgs.
"U.S. Appl. No. 13/725,030, Non Final Office Action dated Oct. 2, 2015", 31 pgs.
"U.S. Appl. No. 13/725,030, Non Final Office Action dated Dec. 5, 2014", 19 pgs.
"U.S. Appl. No. 13/725,030, Preliminary Amendment filed Dec. 21, 2012", 6 pgs.
"U.S. Appl. No. 13/725,030, Response filed Jan. 2, 2014 to Non Final Office Action dated Jul. 5, 2013", 10 pgs.
"U.S. Appl. No. 13/725,030, Response filed Mar. 4, 2015 to Non Final Office Action dated Dec. 5, 2014", 14 pgs.
"U.S. Appl. No. 13/725,030, Response filed Apr. 1, 2016 to Non Final Office Action dated Oct. 2, 2015", 23 pgs.
"U.S. Appl. No. 13/725,030, Response filed May 19, 2014 to Final Office Action dated Mar. 17, 2014", 11 pgs.
"U.S. Appl. No. 13/725,030, Response filed Jun. 5, 2013 to Restriction Requirement dated Apr. 5, 2013", 7 pgs.
"U.S. Appl. No. 13/725,030, Response filed Jul. 6, 2017 to Non Final Office Action dated Jan. 6, 2017", 16 pgs.
"U.S. Appl. No. 13/725,030, Response filed Aug. 25, 2015 to Final Office Action dated May 19, 2015", 21 pgs.
"U.S. Appl. No. 13/725,030, Response Filed Dec. 12, 2017 to Final Office Action dated Sep. 13, 2017", 17 pgs.
"U.S. Appl. No. 13/725,030, Restriction Requirement dated Apr. 5, 2013", 9 pgs.
"U.S. Appl. No. 13/820,079, Advisory Action dated Aug. 13, 2015", 3 pgs.
"U.S. Appl. No. 13/820,079, Examiner Interview Summary dated Sep. 28, 2015", 3 pgs.
"U.S. Appl. No. 13/820,079, Final Office Action dated Apr. 23, 2015", 15 pgs.
"U.S. Appl. No. 13/820,079, Final Office Action dated May 30, 2018", 16 pgs.
"U.S. Appl. No. 13/820,079, Final Office Action dated Nov. 21, 2016", 16 pgs.
"U.S. Appl. No. 13/820,079, Non Final Office Action dated May 31, 2016", 15 pgs.
"U.S. Appl. No. 13/820,079, Non Final Office Action dated Oct. 23, 2014", 14 pgs.
"U.S. Appl. No. 13/820,079, Non Final Office Action dated Nov. 1, 2017", 18 pgs.
"U.S. Appl. No. 13/820,079, Preliminary Amendment filed Feb. 28, 2013", 8 pgs.
"U.S. Appl. No. 13/820,079, Response filed Jan. 22, 2015 to Non Final Office Action dated Oct. 23, 2014", 10 pgs.
"U.S. Appl. No. 13/820,079, Response filed Mar. 1, 2018 to Non Final Office Action dated Nov. 1, 2017", 9 pgs.
"U.S. Appl. No. 13/820,079, Response filed May 18, 2017 to Final Office Action dated Nov. 21, 2016", 11 pgs.
"U.S. Appl. No. 13/820,079, Response filed Jul. 23, 2015 to Final Office Action dated Apr. 23, 2015", 10 pgs.
"U.S. Appl. No. 13/820,079, Response filed Aug. 30, 2016 to Non Final Office Action dated May 31, 2016", 8 pgs.
"U.S. Appl. No. 13/820,079, Response filed Sep. 23, 2015 to Final Office Action dated Apr. 23, 2015", 10 pgs.
"U.S. Appl. No. 13/820,079, Response Filed Sep. 27, 2018 to Final Office Action dated May 30, 2018", 10 pgs.
"U.S. Appl. No. 13/820,079, Response filed Dec. 26, 2013 to Restriction Requirement dated Oct. 25, 2013", 9 pgs.
"U.S. Appl. No. 13/820,079, Restriction Requirement dated Oct. 25, 2013", 9 pgs.
"U.S. Appl. No. 13/913,974, Declaration of Dr. Jeffrey Ross dated Feb. 23, 2016 and filed Feb. 24, 2016", 5 pgs.
"U.S. Appl. No. 13/913,974, Examiner Interview Summary dated Jan. 29, 2016", 3 pgs.
"U.S. Appl. No. 13/913,974, Examiner Interview Summary dated Mar. 2, 2017", 3 pgs.
"U.S. Appl. No. 13/913,974, Final Office Action dated May 4, 2016", 20 pgs.
"U.S. Appl. No. 13/913,974, Final Office Action dated Jun. 15, 2017", 14 pgs.
"U.S. Appl. No. 13/913,974, Non Final Office Action dated Aug. 24, 2015", 12 pgs.
"U.S. Appl. No. 13/913,974, Non Final Office Action dated Dec. 28, 2017", 19 pgs.
"U.S. Appl. No. 13/913,974, Preliminary Amendment filed Jun. 11, 2013", 6 pgs.

(56) References Cited

OTHER PUBLICATIONS

"U.S. Appl. No. 13/913,974, Response filed Feb. 24, 2016 to Non Final Office Action dated Aug. 24, 2015", 10 pgs.
"U.S. Appl. No. 13/913,974, Response filed Aug. 10, 2015 to Restriction Requirement dated Jun. 11, 2015", 7 pgs.
"U.S. Appl. No. 13/913,974, Response filed Oct. 4, 2016 to Final Office Action dated May 4, 2016", 9 pgs.
"U.S. Appl. No. 13/913,974, Response filed Dec. 13, 2017 to Final Office Action dated Jun. 15, 2017", 9 pgs.
"U.S. Appl. No. 13/913,974, Restriction Requirement dated Jun. 11, 2015", 8 pgs.
"Australian Application Serial No. 2006282783, First Examiner Report dated Sep. 23, 2011", 3 pgs.
"Australian Application Serial No. 2006282783, Response filed Apr. 12, 2012 to First Examiners Report dated Sep. 23, 2011", 21 pgs.
"Australian Application Serial No. 2006282783, Response filed Apr. 18, 2013 to Subsequent Examiners Report dated May 28, 2012", 5 pgs.
"Australian Application Serial No. 2006282783, Subsequent Examiners Report dated May 28, 2012", 2 pgs.
"Australian Application Serial No. 2010236855, First Amendment filed Aug. 6, 2014 to First Examiner Report dated Jan. 17, 2014", 10 pgs.
"Australian Application Serial No. 2010236855, First Examiner Report dated Jan. 17, 2014", 4 pgs.
"Australian Application Serial No. 2013224686, First Examiner Report dated Dec. 18, 2014", 2 pgs.
"Australian Application Serial No. 2013224686, Voluntary Amendment filed Jun. 13, 2014", 15 pgs.
"Australian Application Serial No. 2015224503, Response filed Oct. 9, 2017 to Subsequent Examiners Report dated May 4, 2017", 24 pgs.
"Australian Application Serial No. 2015224503, Response filed Nov. 16, 2017 to Subsequent Examiners Report dated Nov. 7, 2017", 17 pgs.
"Australian Application Serial No. 2015224503, Subsequent Examiners Report dated Nov. 7, 2017", 3 pgs.
"Australian Application Serial No. 2015224503, Subsequent Examiners Report dated Nov. 22, 2017", 3 pgs.
"Australian Application Serial No. 2015224503, Subsequent Examiners Report dated Dec. 5, 2017", 3 pgs.
"Austrialian Application Serial No. 2011295779, Examination Report dated Jan. 30, 2015", 3 pgs.
"Austrialian Application Serial No. 2011295779, Response filed Aug. 3, 2015 to Examination Report dated Jan. 30, 2015", 14 pgs.
"Canadian Application Serial No. 2,618,731, Office Action dated Mar. 27, 2013", 3 pgs.
"Canadian Application Serial No. 2,618,731, Office Action dated Mar. 29, 2018", 3 pgs.
"Canadian Application Serial No. 2,618,731, Office Action dated Jun. 13, 2014", 2 pgs.
"Canadian Application Serial No. 2,618,731, Response filed Sep. 26, 2017 to Office Action dated Apr. 7, 2017", 65 pgs.
"Canadian Application Serial No. 2,618,731, Response filed Sep. 27, 2013 to Office Action dated Mar. 27, 2013", 20 pgs.
"Canadian Application Serial No. 2,618,731, Response filed Oct. 1, 2018 to Office Action dated Mar. 29, 2018", 15 pgs.
"Canadian Application Serial No. 2,618,731, Response filed Dec. 12, 2014 to Office Action dated Jun. 13, 2014", 28 pgs.
"Canadian Application Serial No. 2,757,457, Office Action dated Feb. 26, 2016", 6 pgs.
"Canadian Application Serial No. 2,757,457, Office Action dated Dec. 29, 2016", 3 pgs.
"Canadian Application Serial No. 2,757,457, Response filed Jun. 28, 2017 to Office Action dated Dec. 29, 2016", 9 pgs.
"Canadian Application Serial No. 2,757,457, Response filed Aug. 26, 2016 to Office Action dated Feb. 26, 2016", (English Translation of Claims), 33 pgs.
"Canadian Application Serial No. 2,809,990, Office Action dated Jul. 23, 2018", 4 pgs.
"Canadian Application Serial No. 2,809,990, Office Action dated Nov. 27, 2017", 4 pgs.
"Canadian Application Serial No. 2.809.990, Response filed May 25, 2018 to Office Action dated Nov. 27, 2017", 27 Pgs.
"Chinese Application Serial No. 200680030925.4, First Office Action dated Jan. 2, 2010", (English Translation), 4 pgs.
"Chinese Application Serial No. 200680030925.4, Office Action dated Sep. 28, 2011", (w/ English Translation), 10 pgs.
"Chinese Application Serial No. 200680030925.4, Response filed Apr. 15, 2011 to Office Action dated Jan. 31, 2011", (w/ English Translation of Amended Claims), 9 pgs.
"Chinese Application Serial No. 200680030925.4, Response Filed Oct. 19, 2010 to Office Action dated Jun. 4, 2010", (w/ English Translation of Claims), 10 pgs.
"Chinese Application Serial No. 200680030925.4, Response filed Oct. 19, 2010 to Second Office Action dated Jun. 4, 2010", (w/ English Translation of Amended Claims), 10 pgs.
"Chinese Application Serial No. 200680030925.4, Response filed Dec. 12, 2011 to Office Action dated Sep. 28, 2011", (w/ English Translation of Amended Claims), 7 pgs.
"Chinese Application Serial No. 200680030925.4, Third Office Action dated Jan. 31, 2011", (w/ English Translation), 15 pgs.
"Chinese Application Serial No. 201080024899.0, Argument filed Oct. 14, 2013 in response to Office Action dated Jan. 9, 2013", (w/ English Translation), 5 pgs.
"Chinese Application Serial No. 201080024899.0, Decision on Rejection dated Oct. 30, 2013", 7 pgs.
"Chinese Application Serial No. 201080024899.0, Office Action dated Jan. 9, 2013", (w/ English Translation), 16 pgs.
"Chinese Application Serial No. 201180052952.2, Office Action dated Apr. 17, 2014", (w/ English Translation), 21 pgs.
"Chinese Application Serial No. 201180052952.2, Office Action dated May 15, 2015", (w/ English Translation), 31 pgs.
"Chinese Application Serial No. 201180052952.2, Office Action dated Oct. 19, 2015", (w/ English Translation), 12 pgs.
"Chinese Application Serial No. 201180052952.2, Office Action dated Dec. 18, 2014", (w/ English Translation), 11 pgs.
"Chinese Application Serial No. 201180052952.2, Response filed Feb. 27, 2015 to Office Action dated Dec. 18, 2014", (w/ English Translation of Claims), 13 pgs.
"Chinese Application Serial No. 201180052952.2, Response filed Jul. 30, 2015 to Office Action dated May 15, 2015", (w/ English Translation of Amended Claims).
"Chinese Application Serial No. 201180052952.2, Response filed Sep. 2, 2014 to Office Action dated Apr. 17, 2014", (w/ English Translation of Claims), 14 pgs.
"Chinese Application Serial No. 201180052952.2, Response filed Dec. 24, 2015 to Office Action dated Oct. 19, 2015", (w/ English Translation of Amended Claims), 14 pgs.
"Chinese Application Serial No. 201210287455.7, Office Action dated Nov. 14, 2013", (w/ English Translation), 11 pgs.
"Chinese Application Serial No. 201210287455.7, Response filed Mar. 31, 2014 to Office Action dated Nov. 14, 2013", (w/ English Translation of Amended Claims), 9 pgs.
"European Application Serial No. 06790024, Supplementary European Search Report, dated Jun. 5, 2009", 6 pgs.
"European Application Serial No. 06790024.1, Office Action dated Sep. 10, 2010", 7 pgs.
"European Application Serial No. 06790024.1, Office Action dated Sep. 18, 2009", 1 pg.
"European Application Serial No. 06790024.1, Response filed Jan. 20, 2011 to Office Action dated Sep. 10, 2010", 11 pgs.
"European Application Serial No. 06790024.1, Result of Consultation dated Nov. 30, 2009", 3 pgs.
"European Application Serial No. 06790024.1, Supplementary European Search Report dated Jun. 5, 2009", 9 pgs.
"European Application Serial No. 10723848.7, Office Action dated Jul. 8, 2014", 8 pgs.
"European Application Serial No. 10723848.7, Office Action dated Dec. 2, 2011", 2 pgs.

(56) References Cited

OTHER PUBLICATIONS

"European Application Serial No. 10723848.7, Response filed Jun. 12, 2012 to Office Action dated Dec. 2, 2011", 8 pgs.
"European Application Serial No. 11181797.9, Extended Search Report dated Jun. 11, 2012", 7 pgs.
"European Application Serial No. 11181797.9, Office Action dated Feb. 3, 2014", 4 pgs.
"European Application Serial No. 11181797.9, Office Action dated Feb. 21, 2013", 3 pgs.
"European Application Serial No. 11181797.9, Office Action dated Jul. 16, 2012", 2 pgs.
"European Application Serial No. 11181797.9, Response filed Jan. 11, 2013 to Extended European Search Report dated Jun. 11, 2012", 4 pgs.
"European Application Serial No. 11181797.9, Response filed Jun. 26, 2013 to Office Action dated Feb. 21, 2013", 5 pgs.
"European Application Serial No. 11181797.9, Response filed Aug. 13, 2014 to Office Action dated Feb. 3, 2014", 13 pgs.
"European Application Serial No. 11181797.9, Response filed Dec. 23, 2011 to Office Action dated Oct. 28, 2011", 5 pgs.
"European Application Serial No. 11181797.9, Result of Consultation dated Jun. 26, 2014", 3 pgs.
"European Application Serial No. 11776927.3, Examination Notification Art, 94(3) dated Feb. 5, 2014", 6 pgs.
"European Application Serial No. 11776927.3, Office Action dated Apr. 23, 2013", 2 pgs.
"European Application Serial No. 11776927,3, Response filed Jul. 2, 2015 to Telephone Interview on Jun. 23, 2015", 24 pgs.
"European Application Serial No. 11776927.3, Response filed Aug. 15, 14 to Examination Notification Art. 94(3) dated Feb. 5, 2014", 9 pgs.
"European Application Serial No. 11776927.3, Response filed Aug. 15, 2015 to Examination Notification Art. 94(3) dated Feb. 5, 2014", 8 pgs.
"European Application Serial No. 11776927.3, Response filed Nov. 4, 2013 to Office Action dated Apr. 23, 2013", 9 pgs.
"European Application Serial No. 11776927.3, Result of Consultation dated Jun. 29, 2015", 3 pgs.
"European Application Serial No. 15170077.0, Communication Pursuant to Article 94(3) EPC dated Feb. 1, 2017", 2 pgs.
"European Application Serial No. 15170077.0, Communication Pursuant to Article 94(3) EPC dated Oct. 24, 2017", 2 pgs.
"European Application Serial No. 15170077.0, Extended European Search Report dated Dec. 7, 2015", 12 pgs.
"European Application Serial No. 15170077.0, Response filed Mar. 5, 2018 to Communication Pursuant to Article 94(3) EPC dated Oct. 24, 2017", 22 pgs.
"European Application Serial No. 15170077.0, Response filed Jul. 13, 2016 to Extended European Search Report dated Dec. 7, 2015", 8 pgs.
"European Application Serial No. 15170077.0, Response filed Aug. 11, 2017 to Communication Pursuant to Article 94(3) EPC dated Feb. 1, 2017", 10 pgs.
"European Application Serial No. 15170077.0, Response filed Aug. 21, 2015 to Office Action dated Jun. 12, 2015", 4 pgs.
"Indian Application Serial No. 1741/DELNP/2008, First Examiner Report dated Jun. 24, 2013", 3 pgs.
"Indian Application Serial No. 1741/DELNP/2008, Response filed May 28, 2014 to Office Action dated Jun. 24, 2013", 13 pgs.
"Indian Application Serial No. 7719/DELNP/2011, Office Action dated Nov. 1, 2017", 6 pgs.
"International Application No. PCT/US/2011/050266, International Search Report dated Jan. 23, 2012", 6 pgs.
"International Application No. PCT/US/2011/050266, International Written Opinion dated Jan. 23, 2012", 8 pgs.
"International Application Serial No. PCT/US2006/033415, International Preliminary Report on Patentability dated Feb. 26, 2008", 5 pgs.
"International Application Serial No. PCT/US2006/033415, International Search Report dated Dec. 21, 2006", 3 pgs.

"International Application Serial No. PCT/US2006/033415, Written Opinion dated Dec. 21, 2006", 4 pgs.
"International Application Serial No. PCT/US2010/029463, International Preliminary Report on Patentability dated Oct. 13, 2011", 8 pgs.
"International Application Serial No. PCT/US2010/029463, International Search Report dated Dec. 20, 2010", 5 pgs.
"International Application Serial No. PCT/US2010/029463, Written Opinion dated Dec. 20, 2010", 8 pgs.
"International Application Serial No. PCT/US2010/046644, International Preliminary Report on Patentability dated Mar. 8, 2012", 8 pgs.
"International Application Serial No. PCT/US2010/046644, International Search Report dated Jun. 22, 2011", 6 pgs.
"International Application Serial No. PCT/US2010/046644, Written Opinion dated Jun. 22, 2011", 7 pgs.
"International Application Serial No. PCT/US2011/050266, International Preliminary Report on Patentability dated Mar. 5, 2013", 9 pgs.
"Israel Application Serial No. 215463, Notification Prior to Examination dated Nov. 19, 2012", (English Translation), 3 pgs.
"Israel Application Serial No. 215463, Office Action dated Oct. 20, 2014", (English Translation), 3 pgs.
"Israel Application Serial No. 233821, Office Action dated Jul. 7, 2015", (English Translation), 2 pgs.
"Israeli Application Serial No. 189418, Notification Prior to Refusal dated Jan. 13, 2014", (w/ English Summary), 2 pgs.
"Israeli Application Serial No. 189418, Office Action dated Apr. 7, 2013", (English Translation), 2 pgs.
"Israeli Application Serial No. 189418, Office Action dated May 17, 2010", (English Translation), 1 pg.
"Israeli Application Serial No. 189418, Office Action dated Oct. 5, 2011", (w/ English Summary, 2 pgs.
"Israeli Application Serial No. 189418, Response filed Feb. 9, 2014 to Office Action dated Apr. 7, 2013", (English Translation), 36 pgs.
"Israeli Application Serial No. 189418, Response filed Mar. 19, 2012 to Office Action dated Oct. 5, 2011", (English Translation), 9 pgs.
"Israeli Application Serial No. 189418, Response filed Sep. 14, 2010 to Office Action dated May 17, 2010", (English Translation), 5 pgs.
"Israeli Application Serial No. 224964, Office Action dated Nov. 23, 2016", (Translation), 2 pgs.
"Israeli Application Serial No. 224964, Office Action dated Dec. 20, 2015", (English Translation), 2 pgs.
"Israeli Application Serial No. 224964, Office Action Response dated Jun. 25, 2017 in reply to Office Action dated Nov. 23, 2016", (Translation), 4 pgs.
"Israeli Application Serial No. 224964, Response filed Jun. 19, 2016 to Office Action dated Dec. 20, 2015", (Translation), 9 pgs.
"Israeli Application Serial No. 233821, Response filed Apr. 10, 2016 to Office Action dated Jul. 7, 2015", (English Translation of Claims), 3 pgs.
"Japanese Application Serial No. 2008-528231, Decision of Rejection dated Feb. 4, 2013", (w/ English Translation), 4 pgs.
"Japanese Application Serial No. 2008-528231, Office Action dated May 10, 2012", (w/ English Translation), 8 pgs.
"Japanese Application Serial No. 2008-528231, Response filed Nov. 12, 2012 to Office Action dated May 10, 2012", (w/ English Translation of Amendment), 18 pgs.
"Japanese Application Serial No. 2012-248398, Amendment and Argument filed Aug. 18, 2014", (w/ English Translation), 50 pgs.
"Japanese Application Serial No. 2012-248398, Amendment filed Jun. 25, 2013", (w/ English Translation of Amendment), 10 pgs.
"Japanese Application Serial No. 2012-248398, Examiners Decision of Final Refusal dated Jan. 7, 2015", (w/ English Translation), 6 pgs.
"Japanese Application Serial No. 2012-248398, Notice of Reasons for Rejection dated Mar. 5, 2014", (w/ English Translation), 8 pgs.
"Japanese Application Serial No. 2012-503673, Argument and Amendment filed Nov. 28, 2014 in response to Office Action dated Aug. 28, 2014", (w/ English Translation), 20 pgs.

(56) References Cited

OTHER PUBLICATIONS

"Japanese Application Serial No. 2012-503673, Decision of Rejection dated Apr. 22, 2015", (w/English Translation), 6 pgs.
"Japanese Application Serial No. 2012-503673, Office Action dated Aug. 28, 2014", (w/ EnglishTranslation), 11 pgs.
"Japanese Application Serial No. 2013-527329, Office Action dated Jul. 8, 2015", (w/ English Translation), 12 pgs.
"Japanese Application Serial No. 2013-527329, Response filed Oct. 7, 2015 to Office Action dated Jul. 8, 2015", (w/ English Translation of Written Amendment), 12 pgs.
"Japanese Application Serial No. 2015-094591, Office Action dated Apr. 13, 2016", (w/ English Translation), 10 pgs.
"Japanese Application Serial No. 2015-094591, Written Argument and Amendment filed Oct. 13, 2016 to Office Action dated Apr. 13, 2016", (w/ English Translation Of Claims), 21 pgs.
"Japanese Application Serial No. 2015-164446, Examiners Decision of Final Refusal dated Mar. 30, 2017", (w/ English Translation), 9 pgs.
"Japanese Application Serial No. 2015-164446, Office Action dated Jul. 27, 2016", (w/ English Translation), 9 pgs.
"Japanese Application Serial No. 2015-164446, Response filed Nov. 21, 2016 to Office Action dated Jul. 27, 2016", (w/ English Translation of Written Amendment and Argument), 19 pgs.
"Japanese Application Serial No. 2015-164446, Written Amended filed Mar. 13, 2017 in response to Office Action dated Dec. 14, 2016", (Translation), 2 pgs.
"Japanese Application Serial No. 2015-94591, Amendment filed Jun. 5, 2015", (w/ English Translation), 5 pgs.
"Japanese Application Serial No. 2016-201559, Office Action dated Nov. 8, 2017", (w/ English Translation), 6 pgs.
"Japanese Application Serial No. 2016-201559, Response filed May 8, 2018 to Office Action dated Nov. 8, 2017", (w/ English Translation of Amended Claims), 16 pgs.
"Japanese Application Serial No. 2017-147965, Office Action dated Jun. 13, 2018", w/ English translation, 7 pgs.
"Japanese Application Serial No. 2017-147965, Response Filed Dec. 18, 2018 to Office Action dated Jun. 13, 2018", w/English Claims, 2 pgs.
"Korean Application Serial No. 10-2008-7007151, Notice of Preliminary Rejection dated Nov. 24, 2012", (w/ English Translation), 9 pgs.
"Korean Application Serial No. 10-2008-7007151, Office Action dated Jun. 27, 2013", (w/ English Translation), 4 pgs.
"Korean Application Serial No. 10-2008-7007151, Response filed Jan. 24, 2012 to Notice of Preliminary Rejection dated Nov. 24, 2012", (w/ English Translation of Claims), 18 pgs.
"Korean Application Serial No. 10-2008-7007151, Response filed Oct. 28, 2013 to Office Action dated Jun. 27, 2013", (w/ English Translation of Claims), 25 pgs.
"Korean Application Serial No. 10-2013-7008118, Notice of Preliminary Rejection dated Nov. 20, 2017", (w/ English Translation), 6 pgs.
"Korean Application Serial No. 10-2013-7028378, Notice of Preliminary Rejection dated Jan. 24, 2014", (w/ English Translation), 8 pgs.
"Korean Application Serial No. 10-2013-7028378, Response filed Mar. 24, 2014 to Notice of Preliminary Rejection dated Jan. 24, 2014", (w/ English Translation of the Claims), 28 pgs.
"Korean Application Serial No. 10-2014-7007674, Notice of Preliminary Rejection dated Jun. 23, 2014", (w/ English Translation), 4 pgs.
"Liver Regeneration", [online], (c) 1998-2016 Mayo Foundation for Medical Education and Research, Retrieved from the Internet: <URL: http://www.mayo.edu/research/centers-programs/center-regenerative-medicine/focus-areas/liver-regeneration>, (2016), 2 pgs.
"Mexican Application Serial No. MX/a/2008/002589, Office Action dated Nov. 12, 2013", (w/ English Translation), 3 pgs.
"Mexican Application Serial No. MX/a/2008/002589, Response filed Jan. 22, 2014 to Office Action dated Nov. 12, 2013", (w/ English Translation of Amendments), 12 pgs.
"Mexican Application Serial No. MX/A/2011/010197, Office Action dated Apr. 17, 2013", (w/ English Summary), 7 pgs.
"Mexican Application Serial No. MX/A/2011/010197, Office Action dated Aug. 31, 2012", (w/ English Summary), 3 pgs.
"Mexican Application Serial No. MX/A/2011/010197, Response filed Sep. 10, 2013 to Office Action dated Apr. 17, 2013", (w/ English Translation of Claims), 7 pgs.
"Mexican Application Serial No. MX/A/2011/010197, Response filed Dec. 19, 2012 to Office Action dated Aug. 31, 2012", (w/ English Translation of Amended Claims), 13 pgs.
"Mexican Application Serial No. MX/a/2013/002372, Substantive Examination Report dated Mar. 17, 2016", (w/ English Summary), 3 pgs.
"Mexican Application Serial No. MX/a/2014/006778, Office Action dated Jan. 30, 2017", (w/ English Translation), 4 pgs.
"Mexican Application Serial No. MX/a/2014/006778, Office Action dated Sep. 14, 2016", (w/ English Summary), 3 pgs.
"Mexican Application Serial No. MX/a/2014/006778, Response filed Jun. 5, 2017 to Office Action dated Jan. 30, 2017", (w/ English Translation of Claims), 14 pgs.
"Russian Application Serial No. 2008111503, Office Action dated Sep. 15, 2011", (English Translation), 4 pgs.
"Russian Application Serial No. 2008111503, Office Action dated Oct. 27, 2011", W/ English Translation, 10 pgs.
"Russian Application Serial No. 2008111503, Official Action dated Jul. 12, 2010", (w/ English Translation), 10 pgs.
"Russian Application Serial No. 2008111503, Response Filed Jan. 16, 2012 to Office Action dated Sep. 15, 2011", (w/ English Translation of Amended Claims), 10 pgs.
"Russian Application Serial No. 2008111503, Response filed Jul. 14, 2011 to Official Action dated Jul. 12, 2010", (w/ English Translation of Amended Claims), 18 pgs.
"Russian Application Serial No. 2008111503, Response filed Jul. 15, 2011 to Official Action dated Jul. 12, 2010", (w/ English Translation of Amended Claims), 18 pgs.
"Russian Application Serial No. 2011143730, Office Action dated Apr. 1, 2014", (w/ English Translation), 9 pgs.
"Russian Application Serial No. 2011143730, Office Action dated Sep. 19, 2014", (w/ English Translation), 7 pgs.
"Russian Application Serial No. 2011143730, Response filed Aug. 28, 2014 to Office Action dated Apr. 1, 2014", (w/ English Translation of Claims), 6 pgs.
"Russian Application Serial No. 2012122055, Office Action dated Mar. 9, 2017", (w/ English Translation), 7 pgs.
"Russian Application Serial No. 2012122055, Office Action dated Jul. 11, 2016", (With English Translation), 13 pgs.
"Russian Application Serial No. 2012122055, Official Decision of Grant dated Jul. 13, 2017", (w/ English Translation), 14 pgs.
"Russian Application Serial No. 2012122055, Response filed Jan. 11, 2017 to Office Action dated Jul. 11, 2016", (w/ English Summary), 4 pgs.
"Russian Application Serial No. 2012122055, Response filed Jun. 8, 2017", (w / English Translation of Claims), 14 pgs.
"Russian Application Serial No. 2013114382, Office Action dated Feb. 16, 2016", (w/ English Translations), 10 pgs.
"Russian Application Serial No. 2013114382, Office Action dated Nov. 21, 2015", (w/ English Translation), 7 pgs.
"Russian Application Serial No. 2013114382, Response filed Jan. 21, 2016 to Office Action dated Nov. 21, 2015", (w/ English Translation of Amended Claims), 7 pgs.
"Russian Application Serial No. 2013114382, Response filed Aug. 16, 2016 to Office Action dated Feb. 16, 2016", (w/ English Translation of Amended Claims), 8 pgs.
"Singapore Application Serial No. 200801197-5, Invitation to Respond to Written Opinion dated Apr. 2, 2009", 12 pgs.
"Singapore Application Serial No. 200801197-5, Response filed Sep. 2, 2009 to Written Opinion dated Apr. 2, 2009", 4 pgs.
"Singaporean Application Serial No. SG 200801197-5, Examination Report dated Sep. 16, 2010", 8 pgs.
"Stem Cell Definition", [online]. [retrieved on Sep. 21, 2015]. Printout from <www.google.com/search?q=%22stem+cell%22+definition&sourceid=ie7&rls=com.micorsoft.en.>, (2015), 1-2.

(56) References Cited

OTHER PUBLICATIONS

Alberts, B., et al., "In: Molecular Biology of the Cell", (3rd Edition), Garland Publishing, New York and London, (1994), 971-977.
Atala, A., "Recent developments in tissue engineering and regenerative medicine", Curr. Opin. Pediatr., 18(2), (2006), 167-171.
Atala, A., et al., "Tissue-engineered autologous bladders for patients needing cystoplasty", Lancet, 367(9518), (2006), 1241-1246.
Bader, A., et al., "Tissue engineering of heart valves—human endothelial cell seeding of detergent acellularized porcine valves", Eur. J. Cardiothorac. Surg, 14(3), (1998), 279-284.
Badylak, S. F., et al., "Whole-organ tissue engineering: decellularization and recellularization of three-dimensional matrix scaffolds", Annu Rev Biomed Eng., 13, (Aug. 15, 2011), 27-53.
Badylak, S. F., "Xenogeneic extracellular matrix as a scaffold for tissue reconstruction", Transpl. Immunol., 12(3-4), (2004), 367-377.
Baertschiger, R. M., et al., "Xenotransplantation Literature Update Nov.-Dec. 2005", Xenotransplantation, 13(2), (2006), 96-99.
Baptista, P. M., et al., "A Novel Acellular Biologically Derived Scaffold for Tissue Engineering", Pittsburgh Tissue Engineering Initiative, [retrieved on Jul. 27, 2005] [Online]. Retrieved from the Internet: <URL: www.regenerate-online.com/abstract__Baptista.html>, (2005), 2 pgs.
Baptista, P. M, et al., "Human liver bioengineering using a whole liver decellularized bioscaffold", Methods Mol Biol., 1001, (Abstract Only), (2013), 1 pg.
Baptista, P. M, et al., "The use of whole organ decellularization for the generation of a vascularized liver organoid.", Hepatology, 53(2), (Feb. 2011), 604-617.
Baptista, Pedro, et al., "A Novel Whole Organ Bioscaffold for Tissue Engineering and Regenerative Medicine Applications", The FASEB Journal, 21 (Meeting Abstract Supplement), Database Biosis Abstract, (2007), A1233.
Barakat, O., et al., "Use of Decellularized Porcine Liver for Engineering Humanized Liver Organ", Journal of Surgical Research, 173(1), (2012), e11-e25.
Batchelder, Cynthia A., et al., "Natural Scaffolds for Renal Differentiation of Human Human Embryonic Stem Celis for Kidney Tissue Engineering", PLOS One, 10(12): e0143849, (2015), 18 pgs.
Bauer, A., et al., "hDAF porcine cardiac xenograft maintains cardiac output after orthotopic gtransplantation into a baboon—a perioperative study", (Abstract), Xenotransplantation, 12(6), 444-449, (2005), 1 pg.
Bodnar, E., et al., "Damage of Porcine Aortic Valve Tissue Caused by the Surfactant Sodiumdodecylsulphate", Thorac,. Cardiovasc. Surg., 34(2), (1986), 82-85.
Bonandrini, Barbara, et al., "Recellularization of Well-Preserved Acellular Kidney Scaffold Using Embryonic Stem Cells", Tissue Engineering: Part A, vol. 20, Nos. 9 and 10, (2014), 1486-1498.
Bonvillain, R. W, et al., "A nonhuman primate model of lung regeneration: detergent-mediated decellularization and initial in vitro recellularization with mesenchymal stem cells.", Tissue Eng Part A., 18(23-24), (Abstract Only), (Dec. 2012), 1 pg.
Borschel, G. H., et al., "Contractile Skeletal Muscle Tissue-Engineered on an Acellular Scaffold", Plast.. Reconstr. Surg., 113(2), (2004), 595-602.
Brendel, Klaus, et al., "The acellular perfused kidney: a model for basement membrane permeability", Biology and Chemistry of Basement Membranes, Nicholas A Kefalides, author; New York : Academic Press, (1978), 177-193.
Brodie, T. G., "The perfusion of surviving organs", The Journal of Physiology, 29(3), (Jan. 1, 1903), 266-275.
Cartmell, J. S., et al., "Development of Cell-Seeded Patellar Tendon Allografts for Anterior Cruciate Ligament Reconstruction", Tissue Eng., 10(7-8), (2004), 1065-1075.
Cebotari, S., et al., "Construction of Autologous Human Heart Valves Based on an Acellular Allograft Matrix", Circulation,106 (Suppl 1), (2002), I-63-I-68.

Chen, F., et al., "Acellular collagen matrix as a possible "off the shelf" biomaterial for urethral repair", Urology, 54(3), (1999), 407-410.
Chen, F., et al., "Experimental and clinical experience using tissue regeneration for urethral reconstruction", World J. Urol., 18(1), (2000), 67-70.
Chen, R.-Y., et al., "Process development of an acellular dermal matrix (ADM) for biomedical applications", Biomateriais, 25, (2004), 2679-2686.
Conconi, M. T., et al., "Homologous muscle acellular matrix seeded with autologous myoblasts as a tissue-engineering approach to abdominal wall-defect repair", Biomaterials. 26(15), (2005), 2567-2574.
Courtman, D. W., et al., "Development of a pericardial acellular matrix biomaterial: Biochemical and mechanical effects of cell extraction", J Biomed Materi Res., 28(6), (1994), 655-666.
Crapo, Peter M., et al., "An overview of tissue and whole organ decellularization process", Biomaterials, 32, (2011), 3233-3243.
Czyz, Jaroslaw, et al., "Embryonic stem cell differentiation: The role of extracellular factors", Differentiation, 68, (2001), 167-174.
Dahl, S. L., et al., "Decellularized Native and Engineered Arterial Scaffolds for Transplantation", Cell Transplant., 12(6), (2003), 659-666.
Daly, A. B, et al., "Initial binding and recellularization of decellularized mouse lung scaffolds with bone marrow-derived mesenchymal stromal cells", Tissue Eng Part A., 18(1-2), (Abstract Only), (Jan. 2012), 1 pg.
Davis, G. E., et al., "Endothelial Extracellular Matrix— Biosynthesis, Remodeling, and Functions During Vascular Morphogenesis and Neovessel Stabilization", Circ. Res,. 97, (2005), 1093-1107.
Dellgren, G., et al., "Eleven years' experience with the Biocor stentless aortic bioprsthesis: clinical and hemodynamic follow-up with long-term relative survival rate", Eur. J. Cardiothorac.. Surg., 22(6), (2002), 912-921.
Den Butter, G., et al., "Comparison of solutions for preservation of the rabbit liver as tested by isolated perfusion", Transpl.. Int., 8(6), (1995), 466-471.
Deng, M. C., et al., "Destination Mechanical circulatory Support: Proposal for Clinical Standards", J. Heart Lung Transplant., 22(4), (2003), 365-369.
Deyl, Z., et al., "Steric Hindrances in Protein Permeation Through the Basement Membrane Studied in Acellular Kidney", Physiologia Bohemoslovaca, 36(5), (1987), 425-434.
Downing, Gregory J., et al., "Technical Assessment of the First 20 Years of Research Using Mouse Embryonic Stem Cell Lines", Stem Cells, 22, (2004), 1168-1180.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Elkins, R. C., et al., "Decellularized Human Valve Allografts", Ann. Thorac. Surg., 71(Suppl 5), (2001), S428-S432.
Engbers-Buijtenhuijs, P., et al., "Biological characterisation of vascular grafts cultured in a bioreactor", Biomaterials, 27(11), (2006), 2390-2397.
Eshenhagen, T., et al., "Engineering Myocardial Tissue", Circ. Res., 97(12), (2005), 1220-1231.
Faulk, D. M, et al., "Role of the Extracellular Matrix in Whole Organ Engineering", J Cell Physiol., (Abstract Only), (Dec. 18, 2013), 1 pg.
Firth, J. D., et al., "Sodium handling in the isolated perfused kidney of the cirrhotic rat", Clin. Sci., 77(6), (1989), 657-661.
Frantz, Christian, et al., "The extracellular matrix at a glance", Cell Science at a Glance 123(24), (2010), 4195-4200.
Fridman, Robert, et al., "A Pilot Study to Evaluate the Effects of Perfusion-decellularized Porcine Hepatic-derived Wound Matrix on Difficult-to-heal Diabetic Foot Ulcers", Wounds 29(10), (Oct. 2017), 318-324.
Furuta, A., et al., "Pulsatile Cardiac Tissue Grafts Using a Novel Three-Dimensional Cell Sheet Manipulation Technique Functionally Integrates With the Host Heart, in Vivo", Circ. Res,. 98(5), (2006), 705-712.

(56) References Cited

OTHER PUBLICATIONS

Gerecht-Nir, S., et al., "Biophysical regulation during cardiac development and application to tissue engineering", Int. J. Dev. Biol., 50(2-3), (2006), 233-243.

Gilpin, Sarah E., et al., "Enhanced Lung Epithelial Specification of Human Induced Pluripotent Stem Cells on Decellularized Lung Matrix", Ann Thorac Surg,, 98, (2014), 721-729.

Goh, S. K., et al., "Perfusion-decellularized pancreas as a natural 3D scaffold for pancreatic tissue and whole organ engineering.", Biomaterials, 34(28), (2013), 6760-6772.

Grabow, N., et al., "Mechanical and Structural Properties of a Novel hybrid heart Valve Scaffold for Tissue Engineering", Artif. Organs, 28(11), (2004), 971-979.

Groetzner, J., et al., "Results of Pediatric Cardiac Transplantation—Long-Term Results of a 15-Year Experience", Thorac. Cardiov. Surg., 53 (Suppl 2), (2005), S149-S154.

Guan, Yong, et al., "The effective bioengineering method of implantation decellularized renal extracellular matrix scaffolds", Oncotarget,6(34), (2015), 36126-36138.

Hohlfeld, J., et al., "Tissue engineered fetal skin constructs for paediatric burns". Lancet, 366(9488), (2005), 840-842.

Hopper, R. A., et al., "Acellulatization of Human Placenta With Preservation of the Basement Membrane", Ann. Plast. Surg., 51, (2003), 598-602.

Hou, S.-Y., et al., "Tissue-engineered peripheral nerve grafting by differentiated bone marrow stromal cells", Neuroscience, 140(1), (2006), 101-110.

Huang, et al., "Enhanced Functional Maturation of Fetal Porcine Hepatocytes in Three-Dimensional Poly-l-lactic Acid Scaffolds", A Culture Condition Suitable for Engineered Liver Tissues in Large-Scale Animal Studies,, Cell Transplantation, (2006), 799-809.

Hudson, T. W., et al., "Engineering an Improved Acellular Nerve Graft via Optimized Chemical Processing", Tissue Eng., 10(9-10), (2004), 1346-1358.

Hussein, Kamal H., "Three dimensional culture of HepG2 liver cells on a rat decellurized liver matrix for pharmacological studies", Journal of Biomedical Materials B: Applied Biomaterials, vol. 104B, Issue 2, (2015), 263-273.

Ikeda, E., et al., "Growing bioengineered teeth from single cells: potential for dental regenerative medicine", Expert Opin. Biol. Ther, 8(6), (2008), 735-744.

Isenberg, B. C., et al., "Small Diameter Artificial Arteries Engineered In Vitro", Circ. Res., 98(1), (2006), 25-35.

Jawad, H., et al., "Myocardial tissue engineering", British Medical Bulletin, 87, (2008), 31-47.

Juncosa-Melvin, N., et al., "The Effect of Autologous Mesenchymal Stem Cells on the Biomechanics and Histology of Gel-Collagen Sponge Constructs Used for Rabbit Patellar Tendon Repair", Tissue Eng., 12(2), (2006), 369-379.

Kang, Yu-Zhan, et al., "Decellularization technology application in which live reconstruct biological scaffold", National Medical Journal of China, vol. 89, No. 16, 1135-1138, (2009), 2 pgs.

Kasimir, M.-T., et al., "The decellularized porcine heart valve matrix in tissue engineering. Platelet adhesion and activation", Thromb. Haemost., 94, (2005), 562-567.

Keller, Gorder, "Embryonic stem cell differentiation: emergence of a new era in biology and medicine", Genes & Development, 19, (2005), 1129-1155.

Ketchedjian, A., et al., "Recellularization of Decellularized Allograft Scaffolds in Ovine Great Vessel Reconstructions", Ann. Thorac. Surg., 79(3), (2005), 888-896.

Kitahara, Hiroto, et al., "Heterotopic transplantation of a decellularized and recellularized whole porcine heart", Interactive Cardiovascular and Thoracic Surgery, (2016), 1-9.

Knight, R. L., et al., "Tissue Engineering of Cardiac Valves: Re-Seeding of Acellular Porcine Aortic Valve Matrices with human Mesenchymal Progenitor Cells", J. Heart Valve Dis., 14(6), (2005), 806-813.

Kofidis, T., et al., "Myocardial Restoration and Tissue Engineering of Heart Structures", Methods Mol. Med., 140, (2007), 273-290.

Kolker, A. R., et al., "Multilayer Reconstruction of abdominal Wall defects with Acellular Dermal Allograft (AlloDerm) and component Separation", Ann. Plast. Surg., 55(1), (2005), 36-41.

Kren, Stefan, et al., "The Production of a Bio-Engineered Endothelial Intima From Cultured Cells Using Whole Cardiac Cadaveric Extracellular Matrix", Circulation, 116 (Meeting Abstract Supplement), (2007), 4 pgs.

Lapidot, Tsvee, et al., "How do stem cells find their way home?", Blood, 106(6), (2005), 1901-1910.

Lee, M. S., "GraftJacket Augmentation of Chronic Achilles Tendon Ruptures", Orthopedics, 27(1 Suppl.), (2004), 151-153.

Levenberg, S., et al., "Engineering vascularized skeletal muscle tissue", Nat. Biotechnol., 23(7), (2005), 879-884.

Lichtenberg, A., et al., "Flow-Dependent Re-Endothelialization of Tissue-Engineered Heart Valve", J. Heart Valve Dis., 15(2), (2006), 287-294.

Lin, et al., "Assessing Porcine Liver-Derived Biomatrix for Hepatic Tissue Engineering", (2004), 1046-1053.

Lin, P., et al., "Accessing Porcine Liver-Derived Biomatrix for Hepatic Tissue Engineering", Tissue Eng., 10(7-8), (2004), 1046-1053.

Liu, Xiaoqing, et al., "Elastic fiber homeostasis requires lysyl oxidase-like 1 protein", Nature Genetics, 36(2), (2004), 178-182.

Lu, Tung-Ying, et al., "Repopulation of decellularized mouse heart with human induced pluripotent stem cell-derived cardiovascular progenitor cells", Nature Communications, 4, (2013), 1-11.

Matsuura, J. H., et al., "Cellular Remodeling of Depopulated Bovine Ureter Used as an Arteriovenous Graft in the Canine Model", J. Am. Coll. Surg., 198(5), (2004), 778-783.

Matthiesen, T. S., et al., "Abstract 572: Large Solid Organ Perfusion Decellularization—A Start for Human-Sized Tissue Scaffolds", Circulation, 116 Suppl. S,, (2007), 1 pg.

Matthiesen, Thomas, et al., "Creating Biocompatible 3-D Scaffolds for Engineering Cardiovascular Tissues: Heart, Lung, and Kidney", Circulation, 116 (Meeting Abstract Supplement), Database Biosis, (Oct. 2007), 4 pgs.

Matthiesen, Thomas S, et al., "Large Solid Organ Perfusion Decellularization—A Start for Human-Sized Tissue Scaffolds?", Circulation, vol. 116, No. 16, (2007), 103.

Mazzetti, S., et al., "Molecular anatomy of the cerebral microvessels in the isolated guinea-pig brain", Brain Res., 999(1), (2004), 81-90.

McFetridge, P. S., et al., "Preparation of porcine carotid arteries for vascular tissue engineering applications", J. Biomed. Mater Res. A, 70(2), (2004), 224-234.

Mirsadraee, S., et al., "Development and Characterization of an Acellular Human Pericardial matrix for Tissue Engineering", Tissue Eng., 12(4), (2006), 763-773.

Miyagawa, S., et al., "Tissue Cardiomyoplasty using bioengineered Contractile Cardiomyocyte Sheets to Repair Damaged Myocardium: Their Integration with Recipient Myocardium", Transplantation, 80(11), (2005), 1586-1595.

Munoz-Elias, Guillermo, et al., "Marrow Stromal Cells, Mitosis, and Neuronal Differentiation: Stem Cell and Precursor Functions", Stem Cells, 21(4), (Jul. 2003), 437-448.

Naito, H., et al., "Tjhree-Dimensinal Cardiac Tissue Engineering Using a Thermorespoonsive Artificial Extracellular Matrix", ASAIO Journal, 50(4):, (2004), 344-348.

Navarro-Tableros, Victor, et al., "Recellularization of Rat Liver Scaffolds by Human Liver Stem Cells", Tissue Engineering: Part A, vol. 21, Nos. 11 and 12, (2015), 1929-1939.

Oliver, R. F., et al., "Dermal collagen Implants", Biomaterials, 3(1), (1982), 38-40.

Oswald, Joachim, et al., "Mesenchymal Stem Cells can be Differentiated Into Endothelial Cells In Vitro", Stem Cells, 22(3), (2004), 377-384.

Ott, H. C, et al., "Perfusion-Decellularized Matrix: Using Nature's Platform to Engineer a Bioartificial Heart", Nat Med., 14(2), (Feb. 1, 2008), 213-221.

Ott, H. C, et al., "Perfusion-Decellularized Matrix: Using Nature's Platform To Engineer A Bioartificial Heart", Nat. Med., 14(2), (Abstract Only), (2008), 1 pg.

(56) References Cited

OTHER PUBLICATIONS

Ott, H. C, et al., "Regeneration and orthotopic transplantation of a bioartificial lung", Nat Med., 16(8), (Abstract Only), (Aug. 2008), 1 pg.

Ott, H. C., et al., "Regeneration and orthotopic transplantation of a bioartficial lung.", Nature Medicine, 16(18), (Aug. 2010), 927-933.

Park, H., et al., "A novel composite scaffold for cardiac tissue engineering", In Vitro Cell Dev. Biol. Anim., 41, (2005), 188-196.

Park, J.-K., et al., "Bioartificial Liver Systems: Current Status and Future Perspective", J Biosci Bioeng., 99(4), (2005), 311-319.

Pelham, Jr., et al., "Cell locomotion and focal adhesions are regulated by substrate flexibility", Proc. Natl. Acad. Sci. USA 94, (1997), 13661-13665.

Perry, Robert, et al., "Clinical Scale Expansion of Human Pluripotent Stem Cells", (Abstract Only), Blood, 106(11), (2005), 1 pg.

Peters, J. M., et al., "Organ Weights and Water Levels of the Rat following Reduced Food Intake", The Journal of Nutrition, 90, (1966), 354-360.

Petersen, T. H, et al., "Tissue-engineered lungs for in vivo implantation", Science Express, www.sciencexpress.org, (Jun. 24, 2010), 10 pgs.

Petersen, T. H, et al., "Tissue-engineered lungs for in vivo implantation", Science, 329(5991), (Abstract Only), (Jul. 30, 2010), 1 pg.

Petro, Clayton C., et al., "An in vivo analysis of Miromesh—a novel porcine liver prosthetic created by perfusion decellularization", Journal of Surgical Resarch 201, (2016), 29-37.

Phillips, J. B., et al., "Neural Tissue Engineering: A Self-Organizing Collagen Guidance Conduit", Tissue Eng., 11, (2005), 1611-1617.

Philp, D., et al., "Complex extracellular matrices promote tissue-specific stem cell differentiation.", (Abstract Only), Stem Cells, 23(2), 288-296, (2005), 1.

Powers, M. J., et al., "Functional Behavior of Primary Rat Liver Cells in a Three-Dimensional Perfused Microarray Bioreactor", Tissue Eng., 8(3), (2002), 499-513.

Radisic, M., et al., "Mathematical model of oxygen distribution in engineered cardiac tissue with parallel channel array perfused with culture medium containing oxygen carriers.", Am J Physiol Heart Circ Physiol., 288(3), (Mar. 2005), H1278-89.

Rieder, E., et al., "Decellularization protocols of porcine heart valves differ importantly in efficiency of cell removal and susceptibility of the matrix to recellularization with human vascular cells.", J Thorac Cardiovasc Surg., 127(2), (Feb. 2004), 399-405.

Robertson, Matthew J., et al., "Optimizing Recellularization of Whole Decellularized Heart Extracellular Matrix", PLoS ONE, 9(2): e90406, (Feb. 2014), 1-10.

Robinson, K. A., et al., "Extracellular Matrix Scaffold for Cardiac Repair", Circulation 112[suppl I], (2005), I-135-I-143.

Ross, Edward A, et al., "Embryonic Stem Cells Proliferate and Differentiate when Seeded into Kidney Scaffolds", Journal of The American Society of Nephrology, vol. 20, No. 11, (2009), 2338-2347.

Ross, Edward A., et al., "Mouse stem cells seeded into decellularized rat kidney scaffolds endothelialize and remodel basement membranes", Organogenesis, 8:2, (2012), 49-55.

Roy, S., et al., "Biomechanical properties of decellularized porcine common carotid arteries", Am. J. Physiol. Heart Circ. Physiol., 289(4), (2005), H1567-H1576.

Saito, A., "Development of bioartificial kidneys", Nephrology, 8(Issue s2). (Oct. 2003), S10-S15.

Sarraf, C. E., et al., "Cell proliferation rates in an artificial tissue-engineered environment", Cell Prolif., 38(4), (2005), 215-221.

Sayk, F., et al., "Histopathologic Findings in a Novel Decellularized Pulmonary Homograft: An Autopsy Study", Ann. Thorac.. Surg., 79(5), (2005), 1755-1758.

Schaner, P. J, et al., "Decellularized vein as a potential scaffold for vascular tissue engineering", J Vasc Surg., 40(1), (Jul. 2004), 146-53.

Schenke-Layland, K., et al., "Complete dynamic repopulation of decellularized heart valves by application of defined physical signais—an in vitro study.", Cardiovasc Res., 60(3), (Dec. 1, 2003), 497-509.

Schenke-Layland, K., et al., "Impact of decellularization of xenogeneic tissue on extracellular matrix integrity for tissue engineering of heart valves", J. Struct. Biol., 143, (2003), 201-208.

Schlager, Gunther, "Kidney Weight in Mice: Strain Differences and Genetic Determinatino", The Journal of Heredity, 59, (1968), 171-174.

Schmidt, C. E, et al., "Acellular vascular tissues: natural biomaterials for tissue repair and tissue engineering", Biomaterials, 21(22), (Nov. 2000), 2215-31.

Seaberg, R. M., et al., "Stem and progenitor cells: the premature desertion of rigorous definitions", TRENDS in Neurosciences, 26(3), (Mar. 2003), 125-131.

Sekine, H., et al., "Cardiomyocyte Bridging Between Hearts and Bioengineered Myocardial Tissues with Mesenchymal Transition of Mesothelial Cells", J. Heart Lung Transplant., 25(3), (2006), 324-332.

Shimizu, T., et al., "Fabrication of Pulsatile Cardiac Tissue Grafts Using A Novel 3-Dimensional Cell Sheet Manipulation Technique and Temperature-Responsive Cell Culture Surfaces", Circ Res., 90(3), (Feb. 22, 2002), e40-e48.

Shyy, J. Y.-J., et al., "Role of Integrins in Endothelial Mechanosensing of Shear Stress", Circ. Res., 91, (2002), 769-775.

Song, J. J., et al., "Enhanced In Vivo Function of Bioartificial Lungs in Rats", Ann. Thorac. Surg., 92(3), (2011), 998-1006.

Song, J. J, et al., "Regeneration and experimental orthotopic transplantation of a bioengineered kidney", Nat Med., 19(5), (May 2013), 646-651.

Song, Jeremy J,, et al., "Organ engineering based on decellularized matrix scaffolds", Trends in Molecular Medicine 17(8), (2011), 424-432.

Song, Jeremy J., et al., "Regeneration and experimental orthotopic transplantation of a bioengineered kidney", Nature Medicine Advance Online Publication, Received Sep. 4, 2012; accepted Feb. 11, 2013; published online Apr. 14, 2013, (2013), 1-8.

Soto-Gutierrez, A., et al., "A Whole-Organ Regenerative Medicine Approach for Liver Replacement", Tissue Engineering Part C: Methods, 17(6), (2011), 677-686.

Stevenson, L. W., et al., "Left Ventricular Assist Device as Destination for Patients Undergoing Intravenous Inotropic Therapy. A Subset Analysis from REMATCH (Randomized Evaluation of Mechanical Assistance in Treatment of Chronic Heart Failure)", Circulation, 110(8), (2004), 975-981.

Stocum, D. L., "Regenerative biology and medicine", J. Musculoskelet Neuronal Interact., 2(3), (2002), 270-273.

Sudo, R., et al., "Reconstruction of 3d stacked-up structures by rat small hepatocytes on microporous membranes", FASEB J., 19, (2005), 1695-1697.

Sun, T., et al., "Development of a Closed Bioreactor System for Culture of Tissue-Engineered Skin at an Air-Liquid Interface", Tissue Eng., 11(11/12), (2005), 1824-1831.

Suresh, Vijayan, et al., "A retrospective study of the prognostic impact of cytokine secretion in mixed lymphocyte culture on long-term graft function following allogeneic renal transplantation", Transpl Int.,18(9), (2005), 1067-1071.

Swanson, Julia C., et al., "Characterization of Mitral Valve Anterior Leaflet Perfusion Patterns", NIH Public Access, published in final edited form as: J. Heart Valve Dis., 18(5), (2009), 488-495.

Takagi, K., et al., "In Vivo Recellularization of Plain Decellularized Xenografts with Specific Cell Characterization in the Systemic Circulation: Histological and Immunohistochemical Study", Artif. Organs, 30(4), (2006), 233-241.

Taylor, D. A, et al., "Regenerating Functional Myocardium: Improved Performance after Skeletal Myoblast Transplantation", Nature Medicine, 4(8), (1998), 929-933.

Teebken, O. E., et al., "Tissue engineering of vascular grafts: human cell seeding of decellularised porcine matrix", Eur. J. Vasc. Endovasc. Surg., 19(4), (2000), 381-386.

Teebken, O. E, et al., "Tissue engineering:in vitro creation of tissue substitutes", Zentralbl Chir., 132(3), (2007), 236-246.

Toni, R., et al., "The Bioartifical Thyroid: a Biotechnical Perspective in Endocrine Organ Engineering for Transplantation Replacement", Acta Biomed., 78(Suppl 1), (2007), 129-155.

(56) References Cited

OTHER PUBLICATIONS

Uchimura, E., et al., "Novel method of preparing acellular cardiovascular grafts by decellularization with poly(ethylene glycol)", J. Biomed. Mater. Res,. 67(3), (2003), 834-837.
Uygun, B. E, et al., "Decellularization and recellularization of whole livers", J Vis Exp., (48), (Abstract Only), (Feb. 2011), 1 pg.
Uygun, Basak E, et al., "Organ reengineering through development of a transplantable recellularized liver graft using decellularized liver matrix", Nature Medicine, vol. 16, No. 7, (2010), 814-820.
Uzarski, Joseph S., et al., "Epithelial Cell Repopulation and Preparation of Rodent Extracellular Matrix Scaffolds for Renal Tissue Development", Journal of Visualized Experiments, e53271, (2015), 9 pgs.
Wagner, S. M., et al., "The isolated normothermic hemoperfused porcine forelimb as a test system for transdermal absoption studies", J. Artif. Organs, 6(3), (2003), 183-191.
Walles, T., et al., "Acellular Scaffold Implantation—No Alternative to Tissue Engineering", Int. J. Artif. Organs, 26(3), (2003), 225-234.
Wang, P.-C., et al., "Reconstruction of Renal Glomerular Tissue Using Collagen Vitrigel Scaffold", J. Biosci.. Bioeng., 99(6), (2005), 529-540.
Wang, X, et al., "Preparation and characterization of a collagen/chitosan/heparin matrix for an implantable bioartificial liver", J Biomater Sci Polym Ed., 16(9), (2005), 1063-1080.
Wang, Xiaojun, et al., "Decellularized liver scaffolds effectively support the proliferation and differentiation of mouse fetal hepatic progenitors", J. Biomed Mater Res Part A, 102A, (2014), 2027-2025.
Wang, Yunfang, et al., "Lineage Restriction of Human Hepatic Stem Cells to Mature Fates Is Made Efficient by Tissue-Specific Biomatrix Scaffolds", Hepatology, 53, (2011), 293-305.
Weind, Kirsten L., et al., "The Aortic Valve Blood Supply", J. Heart Valve Dis., 9(1), (Jan. 2000), 1-8.
Woods, T., et al., "Effectiveness of three extraction techniques in the development of a decellularized bone-anterior cruciate ligament-bone graft", Biomaterials, 26(35), (Dec. 1, 2005), 7339-7349.
Yagi, H., et al., "Human-Scale Whole-Organ Bioengineering for Liver Transplantation: A Regenerative Medicine Approach", Cell. Transplant., 22(2), (2013), 231-242.
Yang, Lijun, et al., "In vitro trans-differentiation of adult hepatic stem cells into pancreatic endocrine hormone-producing ceils", Proc. Natl. Acad. Sci. USA, 99(12), (2002), 8078-8083.
Yasui, Haruyo, et al., "Excitation propagation in three-dimensional engineered hearts using decellularized matrix", Biomaterials, 35, (2014), 7839-7850.
Zandonella, C., "Tissue Engineering: The Beat Goes On", Nature, 421 (6926), (2003), 884-886.
Zeltinger, J., et al., "Development and characterization of Tissue-Engineered Aortic Valves", Tissue Engineering, 7(11), (2001), 9-22.
Zhou, Pengcheng, et al., "Decellularization and Recellularization of Rat Livers With Hepatocytes and Endothelial Progenitor Cells", Artificial Organs, (2015), 1-14.
Zimmermann, W. H, et al., "Engineered heart tissue for regeneration of diseased hearts", Biomaterials, 25(9), (Apr. 2004), 1639-47.
Zimmermann, W. H., et al., "Engineered heart tissue grafts improve systolic and diastolic function in infarcted rat hearts", Nat. Med., 12(4), (2006), 452-458.
U.S. Appl. No. 12/064,613 8,470,520, filed Oct. 27, 2008, Decellularization and Recellularization of Organs and Tissues.
U.S. Appl. No. 13/725,030, filed Dec. 21, 2012, Decellularization and Recellularization of Solid Organs.
U.S. Appl. No. 13/913,974, filed Jun. 10, 2013, Decellularization and Recellularization of Solid Organs.
U.S. Appl. No. 13/262,286, filed Apr. 2, 2012, Decellularization and Recellularization of Organs and Tissues.
U.S. Appl. No. 13/820,079, filed Feb. 28, 2013, Methods of Recellularizing a Tissue or Organ for Improved Transplantability.
"Canadian Application Serial No. 2,618,731, Response filed Nov. 17, 2020 to Office Action dated Jul. 17, 2020", 47 pgs.

"Japanese Application Serial No. 2019-031120, Examiners Decision of Final Refusal dated Jan. 18, 2021", 6 pgs.
"Japanese Application Serial No. 2019-095766, Response filed Nov. 19, 2020 to Office Action dated May 28, 2020", w/ English Claims, 2 pgs.
"Australian Application Serial No. 2017272168, First Examination Report dated Mar. 5, 2019", 4 pgs.
"Australian Application Serial No. 2017272168, Reply filed Feb. 25, 2020 to Subsequent Examiners Report dated Oct. 4, 2019", 3 pgs.
"Australian Application Serial No. 2017272168, Response filed Aug. 28, 2019 to First Examination Report dated Mar. 5, 2019", 15 pgs.
"Australian Application Serial No. 2017272168, Subsequent Examiners Report dated Oct. 4, 2019", 3 pgs.
"Canadian Application Serial No. 2,809,990, Examiner's Rule 30(2) Requisition dated Oct. 18, 2019", 3 pgs.
"Canadian Application Serial No. 2,809,990, Response filed Apr. 16, 2020 to Examiner's Rule 30(2) Requisition dated Oct. 18, 2019", 18 pgs.
"Indian Application Serial No. 2789/DELNP/2013, First Examination Report dated Jan. 7, 2020", 7 pgs.
"Japanese Application Serial No. 2019-031120, Notification of Reasons for Rejection dated Mar. 23, 2020", (w/ English Translation), 12 pgs.
"Mexican Application Serial No. MX/a/2017/011107, Office Action dated Jun. 12, 2019", (w/ English Translation), 6 pgs.
"Mexican Application Serial No. MX/a/2017/011107, Response filed Aug. 26, 2019 to Office Action dated Jun. 12, 2019", (w/ English Translation of Claims), 13 pgs.
Sawada, N., et al., "Effects of Extracellular Matrix Components on the Growth and Differentiation of Cultured Rat Hepatocytes", *In Vitro Cellular & Developmental Biology,* vol. 23, No. 4, (Apr. 1987), 267-73.
"U.S. Appl. No. 12/064,613, Non Final Office Action dated Sep. 29, 2011", 8 pgs.
"U.S. Appl. No. 13/262,286, Final Office Action dated Jan. 11, 2019", 9 pgs.
"U.S. Appl. No. 13/262,286, Final Office Action dated Mar. 9, 2017", 7 pgs.
"U.S. Appl. No. 13/262,286, Final Office Action dated Aug. 14, 2013", 9 pgs.
"U.S. Appl. No. 13/262,286, Non Final Office Action dated Dec. 14, 2012", 10 pgs.
"U.S. Appl. No. 13/262,286, Respomse filed Sep. 28, 2018 to Non Final Office Action dated Mar. 29, 2018", 13 pgs.
"U.S. Appl. No. 13/725,030, Response Filed Nov. 23, 2016 Final Office Action dated Jun. 23, 2016", 14 pgs.
"U.S. Appl. No. 13/913,974, Amendment and Reply filed Jun. 27, 2018 in response to Non-Final Office Action dated Dec. 28, 2017", 8 pgs.
"U.S. Appl. No. 13/913,974, Applicant's Comments on Substance of Interview filed Dec. 18, 2018", 1 pg.
"U.S. Appl. No. 13/913,974, Applicant-Initiated Interview Summary dated Dec. 13, 2018", 1 pg.
"U.S. Appl. No. 13/913,974, Examiner-Initiated Interview Summary dated Dec. 10, 2018", 3 pgs.
"U.S. Appl. No. 13/913,974, Final Office Action dated Jun. 15, 2017", 16 pgs.
"U.S. Appl. No. 13/913,974, Non Final Office Action dated Nov. 17, 2016", 16 pgs.
"U.S. Appl. No. 13/913,974, Notice of Allowance dated Dec. 13, 2018", 11 pgs.
"U.S. Appl. No. 13/913,974, Response filed May 17, 2017 to Non Final Office Action dated Nov. 17, 2016", 9 pgs.
"Australian Application Serial No. 2015224503, First Examiner Report dated Dec. 5, 2016", 4 pgs.
"Australian Application Serial No. 2015224503, Second Amendment filed Apr. 5, 2017 to First Examiner Report dated Dec. 5, 2016", 14 pgs.
"Australian Application Serial No. 2015224503, Subsequent Examiners Report dated May 4, 2017", 4 pgs.

(56) References Cited

OTHER PUBLICATIONS

"Canadian Application Serial No. 2,618,731, Office Action dated Jan. 5, 2016", 4 pgs.
"Canadian Application Serial No. 2,618,731, Office Action dated Apr. 7, 2017", 5 pgs.
"Canadian Application Serial No. 2,618,731, Response filed Jul. 4, 2016 to Office Action dated Jan. 5, 2016", 4 pgs.
"Canadian Application Serial No. 2,809,990, Response filed Jan. 22, 2019 to Office Action dated Jul. 23, 2018", 15 pgs.
"Chinese Application Serial No. 200680030925.4, Second Office Action dated Jun. 4, 2010", (w/ English Translation), 8 pgs.
"European Application Serial No. 11181797.9, Examination Notification Art. 94(3) dated Feb. 3, 2014", 4 pgs.
"European Application Serial No. 11776927.3, Response filed Aug. 15, 2014 to Examination Notification Art. 94(3) dated Feb. 5, 2014", 9 pgs.
"Japanese Application Serial No. 2015-164446, Office Action dated Dec. 14, 2016", (w/ English Translation), 12 pgs.
"Japanese Application Serial No. 2016-201559, Decision dated Oct. 24, 2018", (w/ English Translation), 4 pgs.
"Japanese Application Serial No. 2017-147965, Examiners Decision of Final Refusal dated Jan. 23, 2019", (w/ English Translation), 8 pgs.
"Russian Application Serial No. 2008111503, Response filed Jan. 16, 2012 to Office Action dated Oct. 27, 2011", (w/ English Translation of Amended Claims), 10 pgs.
Tower, T. T., et al., "Fiber alignment imaging during mechanical testing of soft tissues", *Ann. Biomed. Eng.*, 30(10), (2002), 1221-1233.
Van Putte, Bart P., et al., "Single-pass isolated lung perfusion versus recirculating isolated lung perfusion with melphalan in a rat model", *Ann. Thorac. Surg.*, 74(3), (2002), 893-898.
"Canadian Application Serial No. 2,618,731, Office Action dated Jul. 17, 2020", 4 pgs.
"Canadian Application Serial No. 2,809,990, Office Action dated Jun. 15, 2020", 3 pgs.
"Indian Application Serial No. 2789/DELNP/2013, Response filed Jul. 6, 2020 to First Examination Report dated Jan. 7, 2020", 40 pgs.
"Japanese Application Serial No. 2019-095766, Office Action dated May 28, 2020", (w/ English Translation), 13 pgs.
"Korean Application Serial No. 10-2013-7008118, Response filed Mar. 20, 2018 to Notice of Preliminary Rejection dated Nov. 20, 2017", (w/ English Translation of Claims), 14 pgs.
"U.S. Appl. No. 13/173,400, Final Office Action dated Mar. 26, 2013", 21 pgs.
"U.S. Appl. No. 13/173,400, Final Office Action dated Apr. 23, 2015", 17 pgs.
"U.S. Appl. No. 13/173,400, Final Office Action dated Jun. 1, 2017", 17 pgs.
"U.S. Appl. No. 13/173,400, Final Office Action dated Jun. 4, 2018", 22 pgs.
"U.S. Appl. No. 13/173,400, Final Office Action dated Aug. 5, 2016", 35 pgs.
"U.S. Appl. No. 13/173,400, Non Final Office Action dated Sep. 2, 2014", 20 pgs.
"U.S. Appl. No. 13/173,400, Non Final Office Action dated Oct. 1, 2012", 17 pgs.
"U.S. Appl. No. 13/173,400, Non Final Office Action dated Dec. 3, 2015", 35 pgs.
"U.S. Appl. No. 13/173,400, Non Final Office Action dated Dec. 21, 2017", 18 pgs.
"U.S. Appl. No. 13/173,400, Non Final Office Action dated Dec. 22, 2016", 16 pgs.
"U.S. Appl. No. 13/262,286, Final Office Action dated Jul. 10, 2020", 12 pgs.
"U.S. Appl. No. 13/262,286, Non Final Office Action dated Aug. 9, 2019", 11 pgs.
"U.S. Appl. No. 13/262,286, Preliminary Amendment filed Aug. 17, 2012", 4 pgs.
"U.S. Appl. No. 13/262,286, Response filed Feb. 10, 2020 to Non Final Office Action dated Aug. 9, 2019", 12 pgs.
"U.S. Appl. No. 13/262,286, Response filed Jul. 11, 2019 to Final Office Action dated Jan. 11, 2019", 13 pgs.
"U.S. Appl. No. 13/725,030, Applicant's Summary of Examiner Interview filed Jun. 20, 2019", 2 pgs.
"U.S. Appl. No. 13/725,030, Examiner Interview Summary dated May 6, 2014", 3 pgs.
"U.S. Appl. No. 13/725,030, Examiner Interview Summary dated Jun. 7, 2019", 2 pgs.
"U.S. Appl. No. 13/725,030, Examiner Interview Summary dated Jun. 25, 2018", 3 pgs.
"U.S. Appl. No. 13/725,030, Final Office Action dated Sep. 13, 2018", 23 pgs.
"U.S. Appl. No. 13/725,030, Notice of Allowance dated Jun. 3, 2019", 13 pgs.
"U.S. Appl. No. 13/725,030, Response filed Mar. 13, 2019 to Final Office Action dated Sep. 13, 2018", 16 pgs.
"U.S. Appl. No. 13/725,030, Response filed Jun. 17, 2014 to Advisory Action dated Jun. 5, 2014", 15 pgs.
"U.S. Appl. No. 13/725,030, Response filed Jun. 28, 2018 to Non Final Office Action dated Jan. 29, 2018", 15 pgs.
"U.S. Appl. No. 13/787,625, Final Office Action dated Apr. 1, 2015", 10 pgs.
"U.S. Appl. No. 13/787,625, Non Final Office Action dated Jan. 9, 2014", 12 pgs.
"U.S. Appl. No. 13/787,625, Non Final Office Action dated Jul. 10, 2014", 10 pgs.
"U.S. Appl. No. 13/787,625, Notice of Allowance dated Sep. 25, 2015", 10 pgs.
"U.S. Appl. No. 13/787,625, Notice of Allowance dated Nov. 13, 2015", 7 pgs.
"U.S. Appl. No. 13/820,079, AFCP 2.0 Decision mailed Oct. 29, 2018", 1 pg.
"U.S. Appl. No. 13/820,079, Notice of Allowance dated Oct. 29, 2018", 10 pgs.
"U.S. Appl. No. 13/913,974, Applicant's Summary of Examiner Interview filed Nov. 27, 2018", 1 pg.
"U.S. Appl. No. 13/913,974, Examiner Interview Summary dated Jun. 25, 2018", 3 pgs.
"U.S. Appl. No. 13/913,974, Examiner Interview Summary dated Nov. 5, 2018", 3 pgs.
"U.S. Appl. No. 13/913,974, Notice of Non-Compliant Amendment dated Sep. 13, 2018", 3 pgs.
"U.S. Appl. No. 14/777,397, Final Office Action dated Feb. 22, 2018", 9 pgs.
"U.S. Appl. No. 14/777,397, Non Final Office Action dated Jun. 12, 2017", 8 pgs.
"U.S. Appl. No. 15/079,985, Non Final Office Action dated Aug. 15, 2017", 7 pgs.
"U.S. Appl. No. 15/079,985, Notice of Allowance dated Jan. 30, 2018", 7 pgs.
"U.S. Appl. No. 16/245,435, Preliminary Amendment filed Jan. 11, 2019", 3 pgs.
"U.S. Appl. No. 16/245,435, Supplemental Preliminary Amendment filed Aug. 6, 2019", 7 pgs.
"U.S. Appl. No. 16/554,792, Preliminary Amendment filed Apr. 3, 2020", 12 pgs.
"U.S. Appl. No. 16/554,792, Preliminary Amendment filed Aug. 29, 2019", 3 pgs.
"International Application Serial No. PCT/US2011/050266, International Search Report dated Jan. 23, 2012", 6 pgs.
"International Application Serial No. PCT/US2011/050266, Written Opinion dated Jan. 23, 2012", 8 pgs.
"Japanese Application Serial No. 2012-243398, Amendment filed Jun. 25, 2013", (w/ English Translation), 11 pgs.
"Japanese Application Serial No. 2012-243398, Notice of Reasons for Rejection dated Mar. 5, 2014", (w/ English Translation), 7 pgs.
"Japanese Application Serial No. 2019-095766, Notification of Reasons for Refusal dated Apr. 15, 2021", (w/ English Translation), 10 pgs.
"Japanese Application Serial No. 2021-082285, Voluntary Amendment filed Jun. 14, 2021", (w/ English claims, 8 pgs.

(56) References Cited

OTHER PUBLICATIONS

"Singapore Application Serial No. 200801197-5, Examination Report dated Sep. 16, 2010", 8 pgs.

Bonvillain, Ryan W, "A Nonhuman Primate Model of Lung Regeneration: Detergent-Mediated Decellularization and Initial In Vitro Recellularization with Mesenchymal Stem Cells", Tissue Engineering Part A ,18(23-24), (2012), 2437-2452.

Gilbert, Thomas W., et al., "Decellularization of tissues and organs", Biomaterials, 27, (2006), 3675-3683.

Langer, R., et al., "Tissue Engineering", Science, 260, (1993), 920-926.

L'Heureux, N., et al., "Human tissue-engineered blood vessels for adult arterial revascularization", Nat. Med., 12(3), (2006), 361-365.

Nikalson, L. E., et al., "Functional Arteries Grown in Vitro", Science, 284(5413), (1999), 489-493.

Ott, H. C, et al., "Cell-Based Cardiovascular Repair", Basic Res Cardiol, 100, (2005), 504-517.

Sharma, N. S., et al., "Sodium Butyrate-Treated EmbryonicStem Cells Yield Hepatocyte-Like CellsExpressing a Glycolytic Phenotype", Biotechnology and Bioengineering, 94(6), (2006), 1053-1063.

Zhang, Jianhua, et al., "Functional cardiomyocytes derived from human induced pluripotent stem cells", Circ. Res., 104(4), (2009), e30-e41.

"U.S. Appl. No. 16/245,435, Restriction Requirement dated Nov. 15, 2021", 31 pgs.

"U.S. Appl. No. 16/554,792, Restriction Requirement dated Feb. 17, 2022", 18 pgs.

"U.S. Appl. No. 17/394,243, Supplemental Preliminary Amendment Filed Nov. 18, 2021", 4 pgs.

"Japanese Application Serial No. 2019-095766, Examiners Decision of Final Refusal dated Jan. 26, 2022", w/ English translation, 10 pgs.

"Japanese Application Serial No. 2019-095766, Response filed Sep. 13, 2021 to Notification of Reasons for Refusal dated Apr. 15, 2021", w/English Translation, 21 pgs.

* cited by examiner

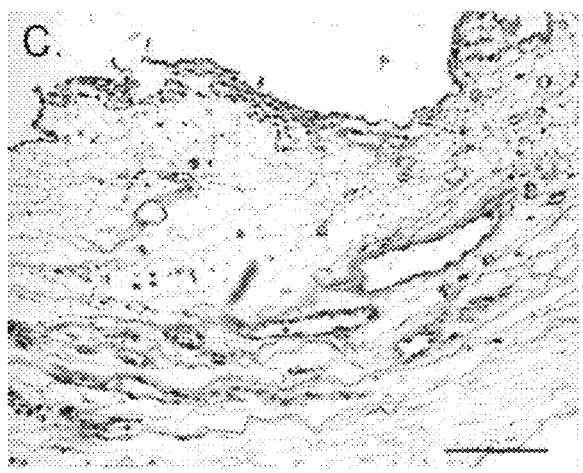 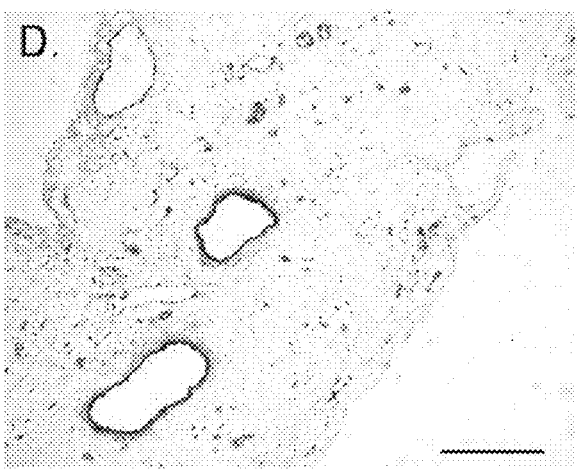
Fig. 3C    Fig. 3D
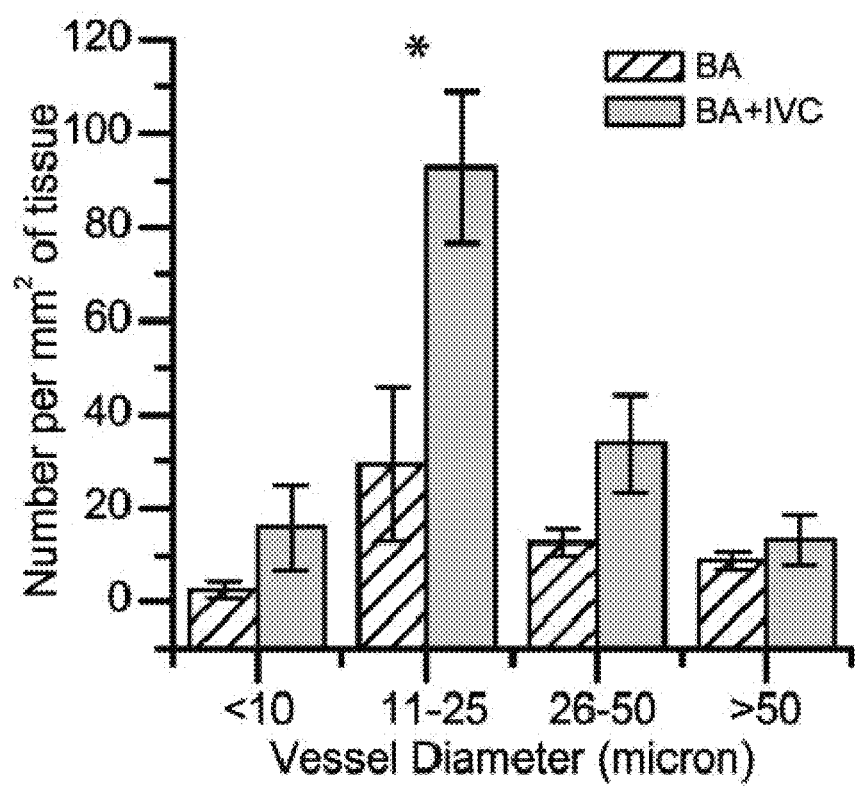
Fig. 3E

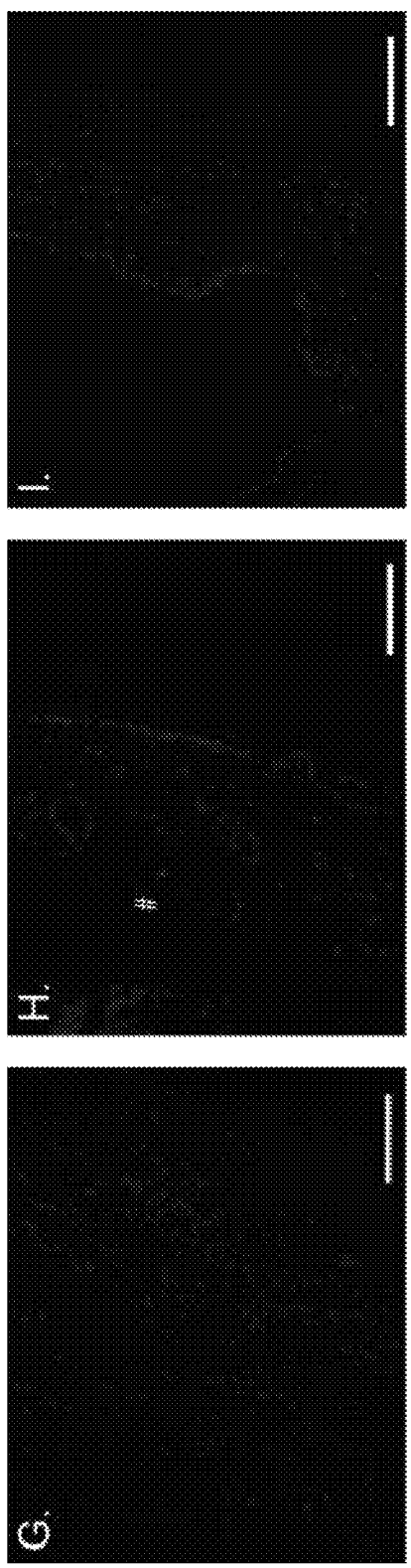

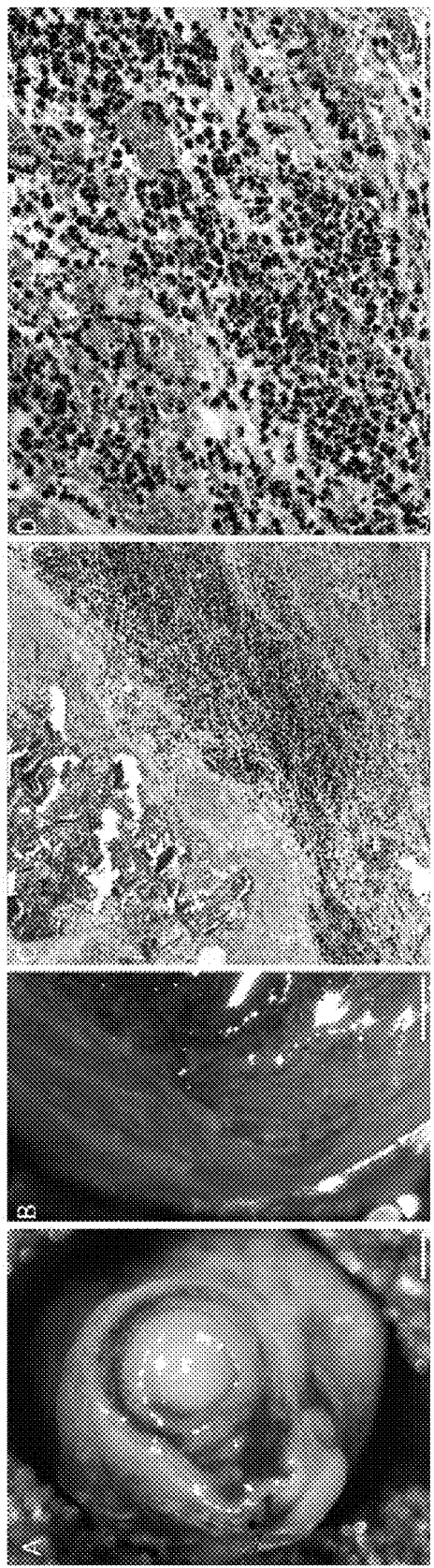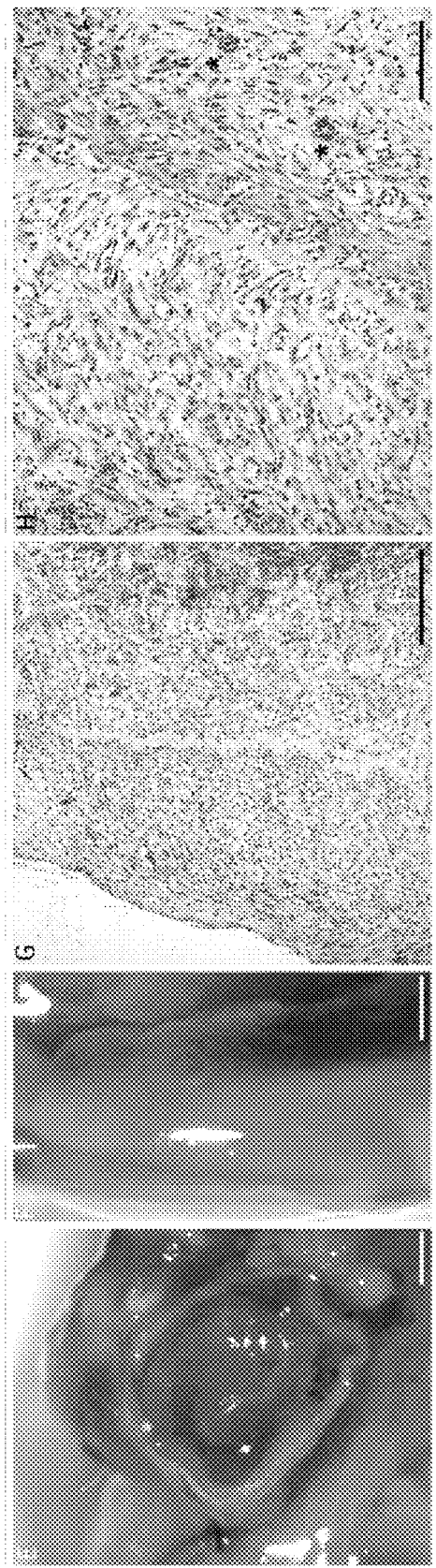

METHODS OF RECELLULARIZING A TISSUE OR ORGAN FOR IMPROVED TRANSPLANTABILITY

RELATED APPLICATIONS

This application is a continuation of U.S. application Ser. No. 13/820,079 which is a U.S. National Stage Filing under 35 U.S.C. § 371 from International Application No. PCT/US2011/050266, filed on 1 Sep. 2011, and published as WO 2012/031162 A1 on 8 Mar. 2012, which claims priority from U.S. Provisional Application Ser. No. 61/379,073 filed Sep. 1, 2010, which applications and publications are incorporated by reference in their entirety.

FEDERALLY SPONSORED RESEARCH OR DEVELOPMENT

This invention was made with government support under Grant Nos. HL 063346 and HL 100407-01 awarded by the National Institutes of Health. The government has certain rights in the invention.

TECHNICAL FIELD

This disclosure generally relates to methods of recellularizing a decellularized tissue or organ.

BACKGROUND

When a blood vessel is injured, or extracellular matrix is exposed, platelets and fibrin form a blood clot to prevent blood loss from the injury. Thrombosis is the formation of the blood clot, which is referred to as a thrombus, inside a blood vessel. The blood vessel may be a vein, an artery, or a capillary. A thrombus typically obstructs, to varying degrees, the flow of blood through the circulatory system. In vivo, antithrombotic and/or anticoagulant agents are used to reduce the clotting response, but these have not proven useful in reducing or eliminating the thrombosis observed during the transplantation of a decellularized organ, tissue, or scaffold.

SUMMARY

In one aspect, a method of recellularizing a tissue or organ matrix is provided. Such a method typically includes perfusing a tissue or organ matrix, e.g., a perfusion decellularized tissue or organ matrix, with a physiological buffer under pressure; and reendothelializing the tissue or organ matrix by perfusing the tissue or organ matrix with a physiological composition comprising a population of endothelial cells or endothelial progenitor cells. An exemplary population of differentiated endothelial cells or smooth muscle cells may be detected using immunocytochemical techniques known in the art including, for example, dual-label immunofluorescence and immunoperoxidase methods that use antibodies that detect cell proteins to distinguish the cellular characteristics or phenotypic properties of endothelial cells or smooth muscle cells. Cellular markers for endothelialcells include for example, VE-cadherin, CD144, CD141, CD 106, or CD142 whereas cellular markers for smooth muscle cells includes Flk. Immunocytochemistry can also be used to identify endothelial cells, by detecting the expression of endothelial cell genes such as CD31 and e-NOS. Mature endothelial cell populations should be relatively absent of hematopoietic cells such at CD45+ populations. In situ hybridization histochemistry may also be performed, using cDNA or RNA probes specific for the endothelial gene mRNAs. These techniques can be combined with immunocytochemical methods to enhance the identification of specific phenotypes. The antibodies and molecular probes discussed above can be applied to Western and Northern blot procedures respectively to aid in cell identification. In one embodiment, the substantially pure population is at least 50%, 60%, 70% or more, such as 80%, 85%, 90%, 95%, 99% or 100% endothelial cells or endothelial progenitor cells. Perfusion decellularization is s an ex vivo method of decellularizing a mammalian organ, part (portion) of an organ or vascularized tissue where a decellularization solution is perfused through organ, part of an organ or vascularized tissue to facilitate decellularization while maintaining the vascular conduits. The resulting decellularized organ, matrix, tissue scaffold or graft retains a vascular system comprising of an arterial supply, interstial space where capillary beds reside and venous output such that fluid or cells can be introduced via one or more entry points, e.g., one or more vessels, and exit the organ, matrix, tissue or graft through a different route. Whole organs will a primary artery input will have complete venous return of fluid. Isolated portions of organs or tissues will have a combination of venous return and fluid exiting via the exposed interstial matrix where the tissue or portion of the organ was excised. When present, the organ capsule remains intact, e.g., does not facilitate the movement of aqueous liquid across the capsule which is in contrast to organs subjected to immersion decellularization.

Representative endothelial cells include, without limitation, blood endothelial cells, bone marrow endothelial cells, circulating endothelial cells, human aorta endothelial cells, human brain microvascular endothelial cells, human dermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, liver sinusoidal endothelial cells, colony forming unit-endothelial cells (CFU-ECs), circulating angiogenic cells (CACs), circulating endothelial precursors (CEPs), endothelial colony-forming cells (ECFC), low proliferative potential ECFC (LPP-ECFC), high proliferative ECFC (HPP-ECFC), or combinations thereof. In some embodiments, the endothelial cells or endothelial progenitor cells are derived from embryonic stem cells (ESC), adult stem cells, progenitor cells or induced pluripotent stem cells (iPSCs).

In certain embodiments, the tissue or organ matrix is a biological tissue or organ matrix. In certain embodiments, the biological tissue or organ matrix originates from an organ selected from the group consisting of a heart, kidney, liver, lung, pancreas, intestine, muscle, skin, breast, esophagus, trachea, or omentum. In certain embodiments, the biological tissue or organ matrix is a perfusion-decellularized tissue or organ matrix.

In certain instances, the biological tissue or organ matrix and the endothelial cells or endothelial precursor cells are xenogeneic. In certain instances, the biological tissue or organ matrix and the endothelial cells or endothelial precursor cells are allogeneic.

In some embodiments, such a method further includes introducing cells other than endothelial or endothelial progenitor cells into or onto the tissue or organ matrix before the reendothelialization step. In some embodiment, such a method further includes introducing cells other than endothelial, endothelial derived, immature endothelial cells, or endothelial progenitor cells into or onto the tissue or organ matrix after the reendothelialization step.

In another aspect, a method of reducing thrombogenesis and immunogenicity in a recellularized tissue or organ following transplantation into a recipient is provided. Such a method typically includes perfusing a tissue or organ matrix with a physiological buffer under pressure; reendothelializing the tissue or organ matrix by perfusing the tissue or organ matrix with a physiological composition comprising a population of endothelial cells or endothelial progenitor cells; and transplanting the reendothelialized tissue or organ matrix into the recipient. Thrombogenicity in re-endothelialized tissues or organs may be assessed via standard hemocompatibility tests and assays including but not limited to, platelet activation, oxidative burst, hemolysis, fibrinolysis, fibrin formation, generation of thrombin, contact activation, thrombomodulin assay, and/or complement activation. In one embodiment, the re-endothelialized tissue or organ matrix is suitable for transplantation and remains patent upon transplantation.

Representative endothelial cells include, without limitation, blood endothelial cells, bone marrow endothelial cells, circulating endothelial cells, human aorta endothelial cells, human brain microvascular endothelial cells, human dermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, liver sinusoidal endothelial cells, colony forming unit-endothelial cells (CFU-ECs), circulating angiogenic cells (CACs), circulating endothelial precursors (CEPs), endothelial colony-forming cells (ECFC), low proliferative potential ECFC (LPP-ECFC), high proliferative ECFC (HPP-ECFC), or combinations thereof. In some embodiments, the endothelial cells or endothelial progenitor cells are derived from embryonic stem cells (ESC), adult stem cells, progenitor cells or induced pluripotent stem cells (iPSCs).

In certain embodiments, the tissue or organ matrix is a biological tissue or organ matrix. In certain embodiments, the biological tissue or organ matrix originates from an organ selected from the group consisting of a heart, kidney, liver, lung, pancreas, intestine, muscle, skin, breast, esophagus, trachea, or omentum. In certain embodiments, the biological tissue or organ matrix is a perfusion-decellularized tissue or organ matrix.

In some embodiments, the biological tissue or organ matrix and the endothelial cells or endothelial precursor cells are xenogeneic. In some embodiments, the biological tissue or organ matrix and the endothelial cells or endothelial precursor cells are allogeneic. In some embodiments, the biological tissue or organ matrix is xenogeneic to the recipient and wherein the endothelial cells or endothelial progenitor cells are allogeneic to the recipient.

In certain embodiments, such a method further includes introducing cells other than endothelial or endothelial progenitor cells into or onto the tissue or organ matrix before the reendothelialization step. In certain embodiments, such a method further includes introducing cells other than endothelial or endothelial progenitor cells into or onto the tissue or organ matrix after the reendothelialization step. In certain embodiments, such a method further includes introducing cells other than endothelial cells or endothelial progenitor cells into or onto the tissue or organ matrix after the transplantation step. The physiological composition that includes cells other than endothelial cells, endothelial derived, or immature endothelial cells or endothelial progenitor cells can be introduced to the tissue or organ matrix via, for example, perfusion, direct injection, topical application, or combinations thereof.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIGS. 3A-3E. Panels A-D are photographs showing the histologic assessment of decellularized rat heart ECM reseeded with RAECs via the BA (40 million cells, Panels A-B) or BA and IVC (20 million each injection, Panels C-D). Panels A and C are hematoxylin- and eosin-stained sections while Panels B and D are Verhoeff-van Gieson-stained. Vessel diameter was quantified and grouped according to size for the LV and RV wall, the data which is shown in Panel E (N=3 per data set). The scale bar is 250 microns.

Figure 1A:
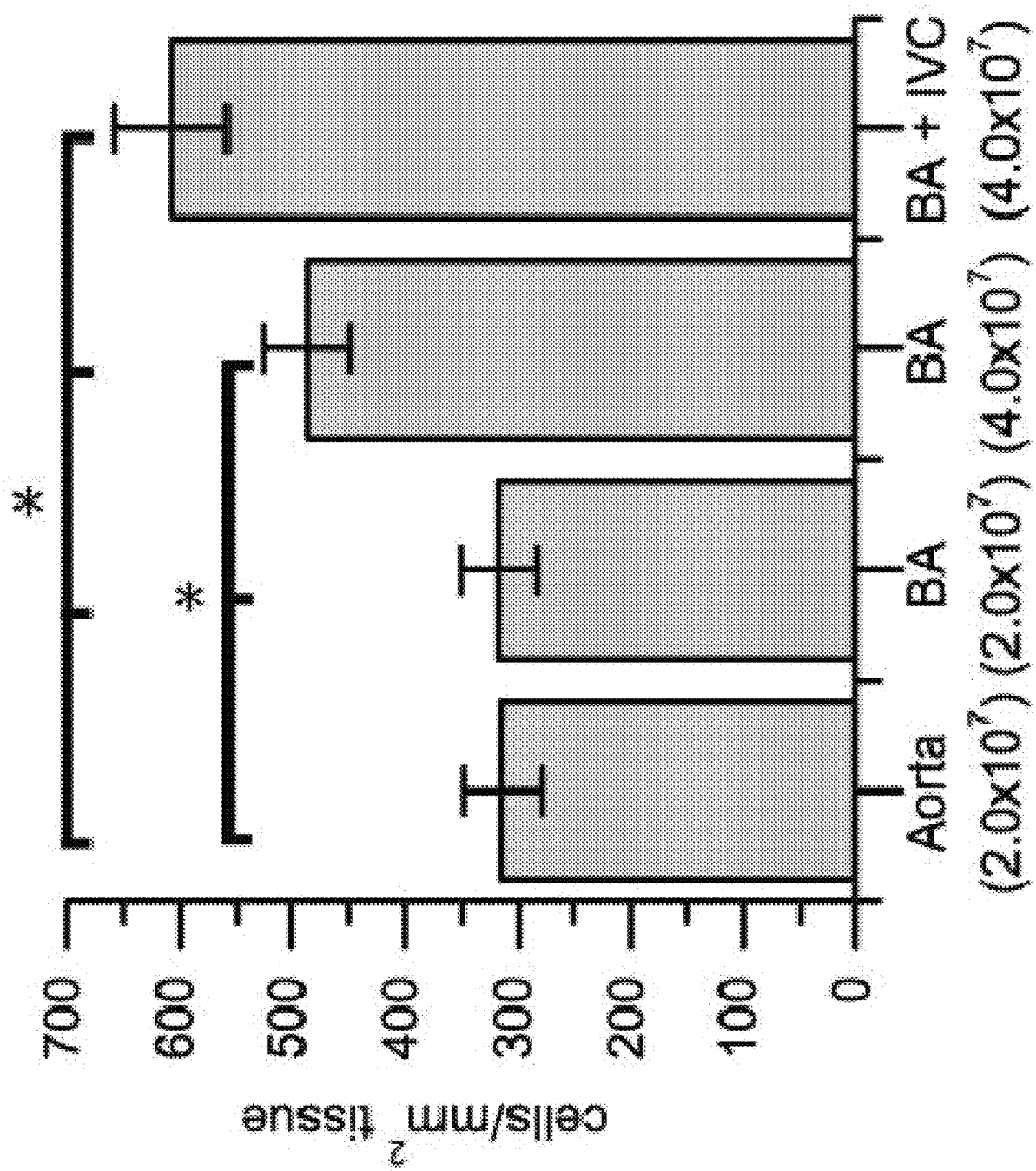
FIGS. 1A-1E. Panel A is a graph showing the presence of cells throughout the recellularized heart constructs, which was estimated by quantifying DAPI positive nuclei at four different short axis locations distributed from base to apex (N=3 hearts per method). Rat aortic endothelial cells (RAECs) were delivered either in a single dose or in two doses. The total number of cells delivered is indicated in parenthesis for each method. Single dose deliveries of cells involved either perfusion of RAECs into the aorta distal to the third branch (Aorta), or via the brachiocephalic artery (BA). In two dose deliveries, half the cells were delivered through the IVC followed by half through the BA (BA+IVC). The distribution of RAECs throughout the whole heart matrix was visualized by DiI (RED) and DiO (GREEN) labeling of cells prior to delivery. 40 million DiI labeled RAECs were delivered via the BA in Panels B and C, while 20 million DiO labeled cells were delivered via the IVC followed by an additional 20 million DiI labeled cells via the BA in Panels D and E. Error bars are the standard error of the mean, and scale bars are 5 mm. * indicates $p>0.05$.

Error bars are one standard deviation from the mean. * indicates a statistically significant difference between the delivery methods (p<0.001) for a given vessel diameter.

FIGS. 4A-4J are photographs of decellularized rat heart constructs seeded at day 0 with 40 million RAECs via infusion into the BA (Panel A) or 30 million RAECs into the IVC (Panels B and C). At day seven, heart constructs were perfused with the vital dye, CMFDA, via the aorta to fluorescently label living cells (GREEN). CMFDA-positive RAECs were seen in the ventricle walls (Panels A and B) and on the endocardial surface of the heart construct (Panel C), irrespective of route of delivery. Cell death due to apoptosis was examined by TUNEL staining (Panels D-I). Panels D-F are representative left ventricle, septum and right ventricle short axis images for a BA cell delivered constructs. Panels G-I are left ventricle, septum and right ventricles TUNEL images for BA and IVC cell seeded constructs. Cell nuclei are stained with DAPI (BLUE) and TUNEL positive staining is RED. To further quantify changes in cell viability over time, media was sampled daily and G6PDH activity was quantified (Panel J) (N=6). Error bars represent one standard deviation from the mean. The scale bar represents 100 microns in Panels A-C, while, in Panels D-I, the scale bar represents 250 microns. # designates TUNEL positive staining. Panel J is a graphical representation of the data.

FIGS. 5A-5D are photographs of histochemical staining of RAECs after seven days on decellularized heart scaffolds, which show that cells are still viable, proliferative (Panel A, GREEN is CMFDA and RED is PCNA), and express markers of functionally active ECs (Panel B, RED is eNOS. GREEN is CMFDA, BLUE is DAPI: Panel C, RED is vWF, GREEN is CMFDA, and BLUE is DAPI). Re-endothelialized matrices were still capable of reducing the thrombogenicity of the scaffolds via thrombomulin signaling (Panel D, N=6 for acellular controls, N=8 for BA and BA+IVC). The total number of RAECs delivered for each method is indicated in parenthesis. * indicates p<0.05 compared to acellular controls. Error bars are standard error of the mean. The scale bar represents 100 microns.

FIGS. 6A-6H are photographs showing a comparison between explants of acellular scaffolds (Panels A-D) and explants of re-endothelialized constructs (Panels E-H) seven days after heterotropic transplantation. Gross examination of the aorta and left ventricle of acellular scaffolds (Panels A and B, respectfully) and re-endothelialized constructs (Panels E and F, respectfully) revealed decreased thrombus formation. Hematoxylin- and eosin-staining of acellular scaffolds (Panels C-D) and re-endothelialized constructs (Panels G-H) revealed more loose blood in acellular scaffolds and comparable amounts of recruited cells within both acellular scaffold and re-endothelialized scaffold explants. * indicate patent vessels in the constructs. Scale bars indicate: 1 mm in Panels A, B, E and F, 250 microns in Panels C and G, 50 microns in Panel D and 100 microns in Panel H.

FIGS. 7A-7D are photographs of VEGF-R2 (RED)-staining of acellular scaffolds (Panel A) or re-endothelialized constructs (Panel B) seven days after transplantation. PECAM (RED) staining of an acellular scaffold (Panel C) and a re-endothelialized construct (Panel D) 7 days after transplantation. DAPI positive nuclei are BLUE. The scale bar represents 100 microns. * indicates blood autofluorescence.

DETAILED DESCRIPTION

Thrombosis of recellularized tissue or organ matrices is a phenomenon that has been reported to occur following transplantation and reperfusion of tissues or organs with blood. In addition, transplanted tissues or organs often are immunogenic, and the recipient often mounts an inflammatory response against the transplanted tissue or organ. Methods of recellularizing a tissue or organ matrix are described herein that result in reduced thrombogenicity when the tissue or organ matrix is subsequently transplanted into a host and re-perfused with blood. The methods of recellularization described herein also result in tissues and organs that, when transplanted and re-perfused with blood, exhibit limited inflammation.

The methods of recellularizing a tissue or organ matrix as described herein can utilize a biological tissue or organ matrix. Representative biological tissues and organ matrices include, for example, heart, liver, kidney, lung, pancreas, spleen, uterus, bladder, esophagus, trachea, spinal cord, joints (e.g., knees, shoulders, or hips), skin, breast, muscle, intestine, omentum, and adipose tissue. A biological matrix also can include, for example, a collagen matrix that has been secreted or remodeled by cells. Recellularizing a biological matrix as described herein typically requires that the matrix be devoid, or at least substantially devoid, of viable cells.

Biological tissues and organs can be decellularized using any number of known methods. For example, a biological tissue or organ can be decellularized using perfusion methods. See, for example, WO 2007/025233 and Ott et al. (2008, Nat. Med., 14:213-21) for descriptions of perfusion-based decellularization methods. Perfusion methods of decellularization have been shown to produce a very good matrix for recellularization. See, for example, WO 2007/025233; Ott et al. (2008, Nat. Med., 14:213-21); Uygun et al., 2010, Nat. Med., 16(7):814-20; Petersen et al., 2010, Science, e-pub June; and Ott et al., 2010, Nat Med., e-pub July.

As an alternative to perfusion-based decellularization, biological tissues or organs can be decellularized by immersed in a decellularization solution that removes the cells. See, for example, U.S. Pat. Nos. 6,376,244 and 6,753,181. In addition, as an alternative to utilizing biological tissues and organ matrices, the methods of recellularization described herein can utilize synthetic tissue or organ matrices, provided that such synthetic matrices possess a vascular bed-type structure. Representative synthetic tissues and organ matrices include, for example, hydrogels, polymers (e.g., biodegradable PLGA, PLA or durable polymers such as polyurethane), collagen scaffolds, ECM matrix scaffolds including collagen fibronectin, laminin, and combinations thereof.

The methods of recellularizing a tissue or organ matrix as described herein include perfusing a tissue or organ matrix with a physiological buffer under pressure. This perfusion of the tissue or organ matrix under pressure is performed prior to introducing any cells into the matrix and, similar to the perfusion used in the decellularization process described in WO 2007/025233, is via the vasculature or other lumen or conduit structure (e.g., the trachea in lungs, the bile duct in liver, the urethra in kidney, etc.) of the organ or tissue matrix, and generally begins with cannulation of the vasculature (e.g., arteries, veins, arterioles, venules and capillaries) and/or other lumens and/or conduits (referred to hereinafter as "vasculature-type" structures) of an organ or tissue matrix (about 1 to about 300 Hg). Cannulation thus includes the insertion of a cannula into a body duct, cavity or vessel, as into the trachea, bladder, or a blood vessel to introduce or remove a fluid, substance or waste. As used herein, perfusion of an organ or tissue matrix under pressure refers to delivering a fluid composition (e.g., a physiological buffer) under enough pressure such that the vasculature and vasculature-type structures in the tissue or organ matrix remains open and expanded, but not so high as to cause damage or distension to the vasculature or vasculature-type structures of the tissue or organ matrix. A physiological buffer suitable for pre-cellular perfusion of a tissue or organ matrix under pressure can be any buffer that is compatible with the tissue or organ matrix. For example, physiological buffers can include nutrients such as sugars and carbohydrates, and also can include pro-endothelial factors (e.g., compounds that have a positive effect on endothelial cells or endothelium) such as, for example, compounds that induce angiogenesis (e.g., VEGF, FGF-1 and/or bFGF). A physiological buffer is generally at physiological pH.

In one embodiment, the physiological buffer suitable for pre-cellular perfusion or cellular perfusion includes but is not limited to phosphate buffer saline (PBS) or culture media solutions suitable for endothelial cell culture including but not limited to EGM-2, EGM-2MV, DMEM, PromoCell Endothelial Cell Medium, Medium 200, DMEMF/12, buffers along with nutritional supplements. e.g., glucose, that may be employed for organ perfusion and/or preservation including transplantation. Those include, for example for heart tissues, Modified Krebs-Henseleit buffer of the following composition was prepared (in mM): 118 NaCl, 4.7 KCl, 1.2 $MgSO_4$, 1.2 $KH_2PO_4$, 25 $NaHCO_3$, 11 glucose, 1.75 $CaCl_2$), and 2.0 pyruvate and 5 U/L insulin or Krebs buffer containing (in mM) 118 NaCl, 4.7 KCl, 25 $NaHCO_3$, 1.2 $MgSO_4$, 1.2 $KH_2PO_4$, 2 $CaCl_2$) gassed with 95% O2, 5% CO2; or glucose (e.g., 11 mM) or glucose in combination with 1 or 1.2 mM palmitate. For kidney tissues, an exemplary medium is KPS-1 Kidney Perfusion Solution. For liver tissues, an exemplary medium is Krebs-Henseleit buffer containing 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$ supplemented with 2% BSA.

Although not bound by any particular mechanism, it is thought that this pre-cellular perfusion under pressure opens and flushes out the matrix and, particularly, the vascular bed of the tissue or organ matrix, thereby exposing more of the matrix to the cells during re-endothelialization and allowing the establishment of a viable endothelium throughout the vasculature of the tissue or organ matrix. It would be understood by those skilled in the art that different tissues and organ matrices (e.g., from different sources, e.g., a heart, liver, lung, kidney, pancreas, etc.) can withstand different amounts of pressure. The amount of pressure a particular tissue or organ matrix can withstand is related, at least in part, to the vascular bed of that particular tissue or organ matrix.

The methods of recellularizing a tissue or organ matrix as described herein also include re-endothelialization of the tissue or organ matrix with endothelial cells, endothelial derived, immature endothelial cells, or endothelial progenitor cells. Sources of endothelial cells include those obtained from an autologous harvest, e.g., a biopsy. Autologous endothelial cells may be harvested from a patient via a biopsy of an artery, vein or a specific tissue and placed into cell culture for normal outgrowth of the population. Selection of endothelial cells is achieved either through culture conditions where VEGF or bFGF suppresses contaminating cells populations including smooth muscle cells or through direct FACS sorting or other available ex vivo selection methods such as magnetic beads, microfluidics, lab-on-a-chip, affinity column or associated device for the population to select for a pure endothelial cell population based on any of the following accepted endothelial cell surface markers including but not limited to CD31, VEGFR-1, VEGFR-2, CD105, CD144, TEM7, CD146 and/or D2-40.

Endothelial progenitor cells (EPCs) are immature endothelial cells, which have the capacity to proliferate, migrate, and differentiate into endothelial cells but have not yet acquired characteristics of mature endothelial cells. EPCs may be mobilized from bone marrow into peripheral blood (circulating EPCs) in response to certain physiological stimuli, such as, for example, tissue injury. Circulating EPCs were identified in adult human blood (Asahara et al. (1997) Science 275:964-967) and subsequent studies have suggested a role for EPCs in the maintenance of endothelial integrity and function, as well as in postnatal neovascularization. EPCs can be isolated from blood, bone marrow, or cord blood and are identified in the CD34+ cell fraction in adult human peripheral mononuclear cells. These can be isolated using CD34+ cells or CD133+ cells alone or in combination with KDR+ as an EPC-rich cell fraction in peripheral blood via direct FACS sorting or other available ex-vivo selection method such as magnetic beads, microfluidics, lab-on-a-chip, affinity column or associated device. EPCs can then either be directly perfused onto the matrix and cultured under appropriate conditions to assist with proliferation and differentiation, or cultured in-vitro to increase overall cell numbers in an EPC maintaining culture medium such as culturing for seven days in serum free StemSpan® medium (StemCell Technologies, Vancouver, Canada) during the initial expansion period and supplemented with 1% penicillin-streptomycin (Sigma-Aldrich, St. Louis, USA) and recombinant human (rh) Flt-3 ligand (100 ng/mL), rh stem cell factor (100 ng/mL), rh IL-3 (20 ng/mL), rh IL-6 (20 ng/mL). These cells and then be perfused into the matrix as EPCs or predifferentiated into ECs and perfused into the matrix. Differentiation of EPCs can be achieved through methods such as culturing about $3 \times 10^5$ to about $1 \times 10^6/1.5$ mL/9.6 $cm^2$ in endothelial cell growth medium-2 (EGM-2) containing FBS (2%), hydrocortisone, hFGF, VEGF, $R^3$-IGF-1, ascorbic acid, hEGF, gentamycin, amphotericin-B and heparin (Lonza, Basel, Switzerland). After three days of culture, the cells can be collected and transferred to plates coated with fibronectin (10 µg/ml) (Sigma-Aldrich, St. Louis, USA) at a density of about $1 \times 10^6$ cells/1.5 mL/9.6 $cm^2$ and cultured for an additional three days in fresh EGM-2 medium.

A population of allogeneic endothelial or endothelial cell precursors may be used and prepared from tissue that is allogeneic to that of the recipient and is tested for use by the well-known methods of tissue typing, to closely match the histocompatibility type of the recipient. These include but are not limited to human umbilical vein endothelial cells (HUVECs), genetically modified endothelial cells to reduce immunogenicity. HLA matched endothelial cells, cord blood derived endothelial cells, ECs derived from EPCs, progenitor, iPS or embryonic stem cells. Most allogeneic approaches will require the use of immunosuppression agents post transplantation. Recent studies have demonstrated the immune privileged nature of ECs derived from EPCs (Cardiovasc Res. 2010 Oct. 1; 88(1):121-9. Epub 2010 Apr. 13) where immune suppression would not be required post transplantation. Examples of EPC differentiation methods include: isolating EPC from the blood by density gradient centrifugation with Pancoll rat (PAN-Biotech), and performing a CD45-depletion using an CD45 monoclonal antibody. The CD45 (−) fraction is cultured in endothelial differentiation medium [EBM supplemented with 5% FCS, 50 mg/mL gentamicin, 10 ng/mL rat VEGF, 1 ng/mL bovine bFGF. 10 ng/mL murine IGF-1 (both R&D Systems), 10 ng/mL murine EGF, and 1 mg/mL hydrocortisone] in 20 mg/mL fibronectin coated dishes. Non-adherent cells were removed by medium change every 4 days. Outgrowing cell clusters appeared after about 15 to about 22 days of culture, and are picked by trypsinization inside cloning rings. PECAM-1(+) cells are selected with MACS separation using a PECAM-1 antibody and IgG1 MicroBeads. The PECAM-1(+) fraction can be further cultured up to passage 25 and can be perfused in multiple matrices.

Additionally, an alternative to employing immunosuppression techniques, methods of gene replacement or knockout using homologous recombination in stem cells, taught by Smithies et al., 317 Nature 230-234 (1985), and extended to gene replacement or knockout in cell lines (Zheng et al., 88 Proc. Natl. Acad. Sci. 8067-8071 (1991)), can be applied to endothelial and endothelial deriving cells for the ablation of major histocompatibility complex (MHC) genes. Cells lacking MHC expression allows for the grafting of enriched endothelial cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 Transplantation 1-11 (1992). Exemplary approaches to the reduction of immunogenicity of transplants by surface modification are disclosed by PCT International patent application WO 92/04033 and PCT/US99/24630. Alternatively the immunogenicity of the graft may be reduced by preparing cells from a transgenic animal that has altered or deleted MHC antigens.

Endothelial cell precursors include but are not limited to colony forming unit-endothelial cells (CFU-ECs), circulating angiogenic cells (CACs), circulating endothelial precursors (CEPs), endothelial colony-forming cells (ECFC), low proliferative potential ECFC (LPP-ECFC), and high proliferative ECFC (HPP-ECFC).

In one embodiment, endothelial cells and endothelial progenitor cells are obtained by culturing embryonic stem cells (ESCs) or induced pluripotent stem cells (iPSCs) under appropriate conditions to direct the stem cells down an endothelial lineage. Endothelial progenitor cells are cells that have begun to differentiate into endothelial cells (e.g., e.g., lineage-restricted; e.g., cells that are destined to become endothelial cells) but are not considered fully differentiated endothelial cells. For example, endothelial progenitor cells can express a progenitor marker such as CD133 and also can express endothelial cell marker such as, without limitation, platelet endothelial cell-adhesion molecule-1 (PECAM1; aka CD31), VEGFR-1 (aka Flt-1), VEGFR-2 (aka Flk-1), guanylate-binding protein-1 (GBP-1), thrombomodulin (aka CD141), VE-cadherin (aka CD 144), von Willebrand factor (vWF), and intercellular adhesion molecule 2 (ICAM-2). Generally, endothelial progenitor cells also are able to take up acetylated LDL, and, further, may migrate toward VEGF and/or form tubes on Matrigel.

ESCs or iPSCs, such as human ESCs and human iPSCs, can be further cultured under conditions that result in fully differentiated endothelial cells, e.g., VEGF and bFGF. Additionally or alternatively, endothelial cells can be obtained from any number of sources such as bone marrow, blood, skin, liver, heart, lung, retina, and any other tissue or organ that harbors endothelial cells. For example, representative endothelial cells include, without limitation, blood endothelial cells, bone marrow endothelial cells, circulating endothelial cells, human aorta endothelial cells, human brain microvascular endothelial cells, human dermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, and combinations thereof. As those of skill in the art would understand, this is not intended to be an exhaustive list of endothelial cells.

EPCs may be obtained from peripheral blood by isolating peripheral blood mononuclear cells (PBMC) by density gradient centrifugation. Cell suspensions are seeded in any receptacle capable of sustaining cells, particularly culture flasks, culture plates or roller bottles, and more particularly in small culture flasks such as 25 $cm^2$ culture flasks. Cells cultured in suspension may be resuspended at approximately $5\times10^4$ to about $2\times10^5$ cells/mL (for example, about $1\times10^5$ cells/mL). Cells plated on a fixed substrate may be plated at approximately 2 to about $3\times10^3$ cells/$cm^2$. Optionally, the culture plates are coated with a matrix protein such as collagen. The cells may be placed into any known culture medium capable of supporting cell growth, including HEM, DMEM, RPMI, F-12, and the like, containing supplements which are required for cellular metabolism such as glutamine and other amino acids, vitamins, minerals and proteins such as transferrin and the like. The culture medium may also contain antibiotics to prevent contamination with yeast, bacteria and fungi such as penicillin, streptomycin, gentamicin and the like. The culture medium may contain serum derived from bovine, equine, chicken and the like. Conditions for culturing generally should be close to physiological conditions. The pH of the culture medium should be close to physiological pH. (for example, between pH 6-8, between about pH 7 to 7.8, or at pH 7.4). Physiological temperatures range between about 30° C. to 40° C. EPCs may be cultured at temperatures between about 32° C. to about 38° C. (for example, between about 35° C. to about 37° C.).

Optionally, the culture medium is supplemented with at least one proliferation-inducing ("mitogenic") growth factor. A "growth factor" is protein, peptide or other molecule having a growth, proliferation-inducing, differentiation inducing, or trophic effect on EPCs. "Proliferation-inducing growth factors" are trophic factor that allows EPCs to proliferate, including any molecule that binds to a receptor on the surface of the cell to exert a trophic, or growth-inducing effect on the cell. Proliferation-inducing growth factors include EGF, amphiregulin, acidic fibroblast growth factor (aFGF or FGF-1), basic fibroblast growth factor (bFGF or FGF-2), transforming growth factor alpha (TGFα), VEGF and combinations thereof. Growth factors are usually added to the culture medium at concentrations ranging between about 1 fg/mL to 1 mg/mL. Concentrations between about 1 to 100 ng/mL are usually sufficient. Simple titration assays can easily be performed to determine the optimal concentration of a particular growth factor. The biological effects of growth and trophic factors are generally mediated through binding to cell surface receptors. The receptors for a number of these factors have been identified and antibodies and molecular probes for specific receptors are available. EPCs can be analyzed for the presence of growth factor receptors at all stages of differentiation. In many cases, the identification of a particular receptor provides guidance for the strategy to use in further differentiating the cells along specific developmental pathways with the addition of exogenous growth or trophic factors.

Generally, after about 3-10 days in vitro, the culture medium of EPCs is replenished by aspirating the medium, and adding fresh medium to the culture flask. Optionally, the aspirated medium is collected, filtered and used as a condition medium to subsequently passage EPCs. For example the 10%, 20%, 30%, 40% or more condition medium is used. The EPC cell culture can be easily passaged to reinitiate proliferation. For example, after about 3 to about 7 days in vitro, the culture flasks are shaken well and EPCs are then transferred to a 50 mL centrifuge tube and centrifuged at low speed. The medium is aspirated, the EPCs are resuspended in a small amount of culture medium, the cells are then counted and replated at the desired density to reinitiate proliferation. This procedure can be repeated weekly to result in a logarithmic increase in the number of viable cells at each passage. The procedure is continued until the desired number of EPCs is obtained.

EPCs and EPC progeny can be cryopreserved by any method known in the art until they are needed. (See, e.g., U.S. Pat. No. 5,071,741, PCT International patent applications WO93/14191, WO95/07611, WO96/27287, WO96/29862, and WO98/14058, Karlsson et al., 65 Biophysical J. 2524-2536 (1993)). The EPCs may be suspended in an isotonic solution, preferably a cell culture medium, containing a particular cryopreservant. Such cryopreservants include dimethyl sulfoxide (DMSO), glycerol and the like. These cryopreservants may be used at a concentration of 5-15% (for example, 8-10%). Cells are frozen gradually to a temperature of $-10°$ C. to $-150°$ C. (for example, $-20°$ C. to $-100°$ C., or $-70°$ C. to $-80°$ C.).

Depending on the culture conditions, EPCs may be differentiated into endothelial cells or smooth muscle cells. EPCs can be differentiated into endothelial cells or smooth muscle cells EPCs on a fixed substrate in a culture medium with a differentiation-inducing growth factor. Differentiation of the EPCs can also be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Instead of proliferation-inducing growth factors for the proliferation of EPCs (see above), differentiation-inducing growth factors can be added to the culture medium to influence differentiation of the EPCs. Other differentiation inducing growth factors include platelet derived growth factor (PDGF), thyrotropin releasing hormone (TRH), transforming growth factor betas (TGF,s), insulin-like growth factor (IGF-1) and the like.

Differentiated endothelial cells or smooth muscle cells may be detected using immunocytochemical techniques know in the art. Immunocytochemistry (e.g. dual-label immunofluorescence and immunoperoxidase methods) uses antibodies that detect cell proteins to distinguish the cellular characteristics or phenotypic properties of endothelial cells or smooth muscle cells Cellular markers for endothelialcells include for example, VE-cadherin. CD144, CD141, CD 106, or CD142 whereas cellular markers for smooth muscle cells includes Flk. Immunocytochemistry can also be used to identify endothelial cells, by detecting the expression of endothelial cell genes such as CD31 and e-NOS.

In situ hybridization histochemistry may also be performed, using cDNA or RNA probes specific for the endothelial gene mRNAs. These techniques can be combined with immunocytochemical methods to enhance the identification of specific phenotypes. If necessary, the antibodies and molecular probes discussed above can be applied to Western and Northern blot procedures respectively to aid in cell identification.

Endothelial cells can be obtained, for example, from one of the many depositories of biological material around the world. See, for example, the American Type Culture Collection (ATCC.org on the World Wide Web) or the International Depositary Authority of Canada (IDAC; nml-lnm.gc.ca on the World Wide Web). Endothelial cells or endothelial progenitor cells also can be obtained from the individual that will be the recipient of the transplanted tissue or organ matrix. These cells would be considered to be autologous to the recipient. Additionally, under certain circumstances, the relationship between the tissue or organ matrix and the endothelial cells or endothelial progenitor cells can be allogeneic (i.e., different individuals from the same species); in other instances, the relationship between the tissue or organ matrix and the endothelial cells or endothelial progenitor cells can be xenogeneic (i.e., individuals from different species). In certain instances, the tissue or organ matrix is xenogeneic to the recipient and the endothelial or endothelial-progenitor cells are allogeneic to the recipient.

A composition that includes endothelial cells or endothelial progenitor cells typically is delivered to a tissue or organ matrix in a solution that is compatible with the cells (e.g., in a physiological composition) under physiological conditions (e.g., $37°$ C.). A physiological composition, as referred to herein, can include, without limitation, buffers, nutrients (e.g., sugars, carbohydrates), enzymes, expansion and/or differentiation medium, cytokines, antibodies, repressors, growth factors, salt solutions, or serum-derived proteins. As used herein, a composition that "consists essentially of" endothelial cells or endothelial progenitor cells is a composition that is substantially free of cells other than endothelial cells or endothelial progenitor cells but may still include any of the components that might be found in a physiological composition (e.g., buffers, nutrients, etc.).

To optimize re-endothelialization, endothelial cells or endothelial progenitor cells generally are introduced into an organ or tissue matrix by perfusion. As with the pre-cellular perfusion, and as described in WO 2007/025233, perfusion occurs via the vasculature or vasculature-type structure (e.g., other lumens or conduits) of the organ or tissue matrix. Perfusion to re-endothelialize an organ or tissue matrix should be at a flow rate that is sufficient to circulate the physiological composition of cells through the vasculature and vasculature-type structures; however, perfusion to re-endothelialize a tissue or organ matrix typically is performed under little to no pressure (e.g., less pressure than is used in the pre-cellular perfusion step to expand and flush the vascular bed). Perfusion with the endothelial cells or endothelial progenitor cells can be multi-directional (e.g., antegrade and retrograde) to even further optimize re-endothelialization.

The number of endothelial cells or endothelial progenitor cells that is introduced into a tissue or organ matrix for re-endothelialization is dependent on both the organ or tissue (e.g., which organ or tissue, the size and weight of the organ or tissue, the developmental stage of the organ or tissue, and/or the extent of vascularization of the organ or tissue) and the type and developmental stage of the endothelial cells, endothelial derived, immature endothelial cells, or endothelial progenitor cells. In addition, more than one type of endothelial cells or endothelial progenitor cells (e.g., a cocktail of endothelial cells or endothelial progenitor cells) can be perfused into an organ or tissue matrix. Different types of endothelial cells or endothelial progenitor cells may have different tendencies as to the population density those cells will reach, and, similarly, different organ or tissue matrices may be re-endothelialized at different densities. Simply by way of example, at least about 100 (e.g., at least about $10^3$, $10^4$, $10^5$, $10^6$, $10^7$, $10^9$ or $10^{10}$) endothelial cells or endothelial progenitor cells can be introduced into an organ or tissue matrix.

Prior to implantation the matrix or graft should contain a majority of mature endothelial cells as defined by the expression of cellular markers for endothelialcells include for example, VE-cadherin, CD 144, CD141, CD 106, or CD142. Immunocytochemistry may also be used to identify endothelial cells, by detecting the expression of endothelial cell genes such as CD31 and e-NOS. A non-destructive method of endothelial isolation would be the brief perfusion of trypsin (0.25% or less) or other cell detachment method to enable the removal of a small fraction <0.01% of the endothelial cells which then can be assayed for the expression of endothelial cell markers including but not limited to CD105, CD31 and functional expression of e-NOS. In additional function of the endothelial cells may be assessed through endothelial tube formation in Matrigel assays. In brief, wells of a 96-well plate were coated with 50 µL ice cold Matrigel™ followed by incubation at 37° C. for one hour. Thereafter, 100 µL EGM-2 medium containing about 25,000 to about 50,000 endothelial cells are added to the Matrigel™. Incubation is carried out for 16 hours in a humidified atmosphere at 37° C. with 5% $CO_2$. Tube formation is assessed with an inverted microscope and digital photomicrographs of each single well were taken at a four times magnification and the total number of tubes, the branching points, the length of the tubes as well as the sum of the lengths of the tubes can be calculated for each well were the presence of endothelial tubes defined functional endothelial cells.

In addition, measurement of re-endothelialization can be completed through the use of standard hemocompatibility tests and assays including but not limited to, platelet activation, oxidative burst, hemolysis, fibrinolysis, fibrin formation, generation of thrombin, contact activation, and complement activation. Non-destructive methods include the use of proliferation assay such at CellTiter Blue or other metabolic assays to determine the density of endothelial cells present in the matrix which can be extrapolated to known values of native tissue where the goal is to have >50% endothelial cell density of a native tissue.

Measurement of re-endothelialization may be conducted through the use of standard hemocompatibility tests and assays including but not limited to, platelet activation, oxidative burst, hemolysis, fibrinolysis, fibrin formation, generation of thrombin, contact activation, and complement activation. Non-destructive methods include the use of proliferation assay such at CellTiter Blue or other metabolic assays to determine the density of endothelial cells present in the matrix which can be extrapolated to known values of native tissue where the goal is to have >50% endothelial cell density of a native tissue.

Perfusion pressures for the introduction of endothelial cells generally corresponds to the native perfusion pressures of the tissues or organs of which the matrix or scaffold had been derived within in range of +/−300% as the vasculature is capable of sustaining pressures >300 mm Hg.

A re-endothelialized tissue or organ matrix as described herein can be transplanted into a recipient. Such a re-endothelialized tissue or organ matrix exhibits very little thrombogenesis and very little immunogenicity. Such a re-endothelialized tissue or organ matrix, once transplanted, can be further recellularized in vivo. After transplantation, such a re-endothelialized tissue or organ matrix can be recellularized in vivo (i.e., with native cells from the recipient). Recellularization in vivo can include further re-endothelialization and/or recellularization with cells other than endothelial cells or endothelial progenitor cells (e.g., tissue- or organ-specific cells such as hepatocytes, bile duct epithelial cells, stem cells, progenitor cells, iPS cells, bone marrow mononuclear cells, smooth muscle cells cardiomyocytes, cardiac fibroblasts, fibroblasts, kuffner cells, skeletal muscle cells, satellite cell, kidney glomerulus parietal cell, kidney glomerulus podocyte, kidney proximal tubule brush border cell, loop of Henle thin segment cell, kidney distal tubule cell, kidney collecting duct cell, type I pneumocyte (lining air space of lung cell), pancreatic duct cell (centroacinar cell), beta cell, islet cells, cell, intercalated cell, intestinal brush border cell (with microvilli), exocrine gland striated duct cell, gall bladder epithelial cell, epididymal principal cell, interstitial kidney cells, and/or epididymal basal cells).

Optionally, a tissue or organ matrix can be recellularized in vitro with cells other than endothelial or endothelial progenitor cells before the tissue or organ matrix is re-endothelialized or after the tissue or organ matrix has been re-endothelialized. As used herein, cells "other than endothelial, endothelial derived or endothelial progenitor cells" refer to all the other types of cells that populate a particular tissue or organ. In the methods described herein, stem cells or progenitor cells (e.g., embryonic stem cells (ESC), adult stem cells, or induced pluripotent stem (iPS)) can be used to recellularize the parenchyma of a tissue or organ, or tissue- or organ-specific cells (i.e., differentiated or partially-differentiated cells) can be used to recellularize the parenchyma of a tissue or organ. With tissue- or organ-specific cells, the particular type of cell delivered typically depends on the type of tissue or organ that is ultimately being produced. For example, when recellularizing a heart, cardiocytes, smooth muscle cells, cardiac fibroblasts and/or cardiac stem cells can be introduced into or onto the tissue or organ matrix; when recellularizing a liver, hepatocytes, bile duct cells, smooth muscle cells, fibroblasts and/or hepatocyte progenitor cells can be introduced into or onto the tissue or organ matrix; when recellularizing a kidney, podocytes, glomerular cells, and/or epithelial cells can be introduced into or onto the tissue or organ matrix; when recellularizing a lung, epithelial cells, clara cells, goblet cells, alveolar type 1, and/or alveolar type II cells can be introduced into or onto the tissue or organ matrix; when recellularizing a pancreas, beta-cells and/or islet cells can be introduced into or onto the tissue or organ matrix.

As with the endothelial cells or endothelial progenitor cells, cells other than the endothelial or endothelial progenitor cells can be delivered to a tissue or organ matrix in a physiological composition (e.g., with buffers, nutrients, enzymes, growth or differentiation medium), and can be delivered or introduced using any number of routes (e.g., injection (e.g., at multiple locations), perfusion, infusion, and/or topical application).

In embodiments in which the cells other than the endothelial or endothelial progenitor cells are introduced following the re-endothelialization of the tissue or organ matrix, it may be beneficial to allow the endothelial cells or endothelial progenitor cells some Lime to adhere to and become established within the vasculature of the tissue or organ matrix before any other cells are delivered. A sufficient time for endothelial cells or endothelial progenitor cells to adhere to the tissue or organ matrix is, for example, 30 to 180 minutes. However, the endothelial cells or endothelial progenitor cells can be allowed to adhere and become established in the tissue or organ matrix for up to, for example, 28-30 days (e.g., about 1 month).

In one embodiment, a decellularized liver graft or lobe is re-endothealized with arterial, venous and/or liver sinusoidal endothelial cells to create a transplantable liver graft capable of being transplanted and anastomosed into the native liver blood supply. The liver graft is recellularized naturally in vivo through the migration of cells from the adjacent liver.

In another embodiment, a decellularized liver graft or lobe is re-endothealized with arterial, venous and/or liver sinusoidal endothelial cells to create a transplantable liver graft capable of being transplanted and anastomosed into the native liver blood supply. After transplant, other cells are perfused via the patient's vasculature or injected into the interstitium of the liver graft, such as hepatocytes (autologous, allogenic, stem cell derived or iPS derived).

In another embodiment, a decellularized liver graft or lobe is first re-endothealized and secondly injected with hepatocytes to create a transplantable liver graft capable of being transplanted and anastomosed into the native liver blood supply.

In another embodiment, a decellularized cardiac graft or patch is re-endothealized to create a transplantable cardiac graft capable of being transplanted and anastomosed into the native cardiac blood supply. The graft is anastomosed and placed over an ischemic region of the heart.

In another embodiment, a decellularized cardiac graft or patch is re-endothealized to create a transplantable cardiac graft capable of being transplanted and anastomosed into the native cardiac blood supply. After transplant, other cells are perfused via the patients vasculature or injected into the interstitium of the cardiac graft, such as cardiomyocytes (autologous, allogenic, stem cell derived or iPS derived).

In another embodiment, a decellularized cardiac graft or patch is re-endothealized to create a transplantable cardiac graft capable of being transplanted and anastomosed into the native cardiac blood supply. Ischemic tissue for the heart is removed and the reendothelialized graft is anastomosed and surgically implanted.

In another embodiment, a decellularized cardiac graft or patch is first re-endothealized and later injected with cardiomyocytes to create a transplantable cardiac graft capable of being transplanted and anastomosed into the native cardiac blood supply. Ischemic tissue for the heart is removed and the contractile graft is anastomosed and surgically implanted.

In one embodiment, a decellularized lung graft or lobe is re-endothealized with endothelial cells to create a transplantable lung graft capable of being transplanted and anastomosed into the native liver blood supply. The lung graft is recellularized naturally in vivo through the migration of cells from the adjacent lung tissue.

In another embodiment, a decellularized lung graft or lobe is re-endothealized with arterial, venous and/or liver sinusoidal endothelial cells to create a transplantable lung graft capable of being transplanted and anastomosed into the native liver blood supply. After transplant, other cells are perfused via the patients vasculature or injected into the interstitium of the graft into the lung graft, such as lung epithelial cells (autologous, allogenic, stem cell derived or iPS derived).

In one embodiment, a decellularized kidney graft or lobe is re-endothealized with endothelial cells to create a transplantable kidney graft capable of being transplanted and anastomosed into the native liver blood supply. The lung graft is recellularized naturally in vivo through the migration of cells from the adjacent kidney.

In another embodiment, a decellularized kidney graft or lobe is re-endothealized with endothelial cells to create a transplantable liver graft capable of being transplanted and anastomosed into the native kidney blood supply. After transplant, other cells are perfused via the patients vasculature or injected into the interstitium of the graft into the kidney graft, such as kidney tubule cells (autologous, allogenic, stem cell derived or iPS derived).

In one embodiment, a decellularized pancreas graft or lobe is re-endothealized with endothelial cells to create a transplantable pancreas graft capable of being transplanted and anastomosed into the native liver blood supply. The lung graft is recellularized naturally in vivo through the migration of cells from the adjacent pancreas.

In another embodiment, a decellularized pancreas graft or lobe is re-endothealized with endothelial cells to create a transplantable liver graft capable of being transplanted and anastomosed into the native pancreas blood supply. After transplant, other cells are perfused via the patients vasculature or injected into the interstitium of the graft into the pancreas graft, such as beta cells (autologous, allogenic, stem cell derived or iPS derived).

In one embodiment, the stating material is a perfusion decellularized liver lobe. In another embodiment, the stating material is part of a perfusion decellularized liver lobe. In another embodiment, the starting material is a perfusion decellularized cardiac graft isolated from the left ventricle. In another embodiment the starting material is a perfusion decellularized cardiac graft isolated from the right ventricle. In another embodiment, the starting material is a perfusion decellularized lung graft isolated from a lung lobe. In another embodiment, the starting material is a perfusion decellularized lung lobe. In another embodiment, the starting material is a perfusion decellularized kidney. In another embodiment, the starting material is a perfusion decellularized kidney graft isolated from a portion of the kidney. In another embodiment, the starting material is a perfusion decellularized pancreas. In another embodiment, the starting material is a perfusion decellularized pancreas graft isolated from a portion of the pancreas.

As indicated herein, the recellularization methods described herein, which result in extensive re-endothelialization of the tissue or organ matrix, produce a tissue or organ matrix that, when transplanted into a recipient, exhibits very little thrombogenicity. Such a re-endothelialized tissue or organ matrix also exhibits very little immunogenicity, based on the amount of inflammation observed in the transplanted tissue or organ and/or the inflammatory response mounted by the recipient following transplantation.

In accordance with the present disclosure, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Animals

All experiments were performed in accordance with US Animal Welfare Act and were approved by the Institutional Animal Care and Use Committee at the University of Minnesota. Heart matrices were derived from Sprague Dawley (250-319 g) or Fisher 344 rats (196-296 g). Fisher 344 matrices were used in transplant studies. All rats used in the generation of heart scaffolds were anesthetized with 100 mg of ketamine per kg of body weight (Phoenix Pharmaceutical) and 10 mg xylazine per kg of body weight (Phoenix Pharmaceutical) followed by systemic heparinization.

Example 2—Decellularization of Cadaveric Rat Hearts

Cadaveric rat hearts were decellularized following previously published methods (Ou et al., 2008; Nature Med., 14(2):213-21). Briefly, rats were anesthetized. Next, a median sternotomy was performed followed by dissection of the pericardium and removal of the retrosternal fat body to expose the mediastinal vessels. The first three branches off the ascending thoracic aorta and both superior vena cavae were ligated and transected. The inferior vena cava (IVC) and the pulmonary vessels (veins and arteries) were transected. The isolated heart was then removed from the thoracic cavity, placed in a petri dish containing PBS, catheterized, and flushed with PBS. The heart was then gravity perfused with 1% SDS followed by washes with deionized water, 1% Triton-X100 (Sigma), and antibiotic-containing PBS (100 U/ml penicillin, 100 U/ml streptomycin; Gibco).

Example 3—Recellularization of Rat Heart Scaffolds

Rat aortic endothelial cells (RAECs) were purchased from Vec Technologies (Rensselaer, N.Y.). RAECs between passages 14 and 20 were used in all experiments. RAECs were cultured on gelatin-coated T185 flasks in complete MCDB-131 (Vec Technologies) and passed using TrypLE Express (Invitrogen). For recellularization via the aorta, retrograde aortic perfusion of cell suspensions was performed into the decellularized scaffolds; for recellularizations via the brachiocephalic artery (BA), constructs under continuous retrograde aortic media perfusion had cells infused into the BA. Constructs that were recellularizaed via the IVC had a catheter placed into the IVC followed by RAEC perfusion. For all constructs, cells were infused at 10 million cells per mL. Unless otherwise specified, constructs were cultured with continuous media perfusion via the aorta (complete MCDB-131) for seven days in a tissue culture incubator. The media reservoir was continuously injected with carbogen (5% $CO_2$ and 95% $O_2$) for the duration of the experiment.

Example 4—Cell Labeling

In a subset of studies, RAECs were labeled with DiI or DiO on the day of recellularization. Briefly, media was removed from a confluent plate of RAECs and replaced with DPBS containing 5 μM SP-DiIC$_{18}$ or SP-DiOC$_{18}$ (Invitrogen). After 5 minutes of incubation at 37° C., plates were transferred to a refrigerator and incubated for 15 minutes at 4° C. Plates were then washed once with PBS and allowed to recover for 2 hours at 37° C. in culture media before isolation and construct seeding. At the end of the experiment, constructs were removed from the bioreactor and imaged on a Stereo Discovery V20 Macro Stereo (Carl Zeiss Inc.), dissected, placed in Slowfade (Invitrogen) and imaged on a 510 Meta Confocal microscope (Carl Zeiss Inc.).

In separate studies, RAECs seeded constructs were labeled with Cell Tracker Green CMFDA (Invitrogen) on the last day of culture (Day 7), by removing the complete culture media and circulating serum free CMFDA containing DMEM (Cellgro) for 45 minutes at 37° C. CMFDA containing media was then replaced with complete MCDB-131 and the constructs were incubated for 45 minutes. CMFDA-labeled constructs were then removed from the bioreactor, dissected, placed in Slowfade (Invitrogen) and imaged on a 510 Meta Confocal microscope (Carl Zeiss Inc.).

Example 5—Histology and Cell Nuclei/Vessel Quantification

On the last day of culture, constructs were removed from the bioreactor, sectioned into four short axis views randomly distributed from the base to the apex, and then paraffin embedded. After paraffin embedding, sectioning and rehydration, they were hematoxylin- and eosin- or Verhoeff van Gieson-stained following standard protocols. Slides were imaged using a Nikon Eclipse TE200 inverted microscope (Fryer Co. Inc.). For nuclei quantification, unstained slides were mounted in Vectashield containing DAPI (Vectorlabs), and 5 random high powered images per section were taken. DAPI-positive nuclei were then quantified and normalized to tissue area. For vessel diameter quantification, 5 randomly distributed high-powered images were taken of Verhoeff-van Gieson-stained sections and processed as described previously. The diameter was estimated by measuring the short axial diameter of cell containing vessel with ImageJ software (NIH). All imaging was performed using a Nikon Eclipse TE200 inverted microscope (Fryer Co. Inc.).

Example 6—Immunofluorescent Staining

Paraffin sections were rehydrated through changes of xylene and graded alcohols. Slides were boiled in 10 mM citrate buffer with 0.05% Tween-20 at pH 6.0 for 20 min. Blocking was preformed with 3% BSA in PBS for one hour. Primary antibodies to PCNA, PECAM-1 (rabbit polyclonal, Santa Cruz), vWF, eNOS, Calretinin, Vimentin (rabbit polyclonal, Abcam), vWF (goat polyclonal, Santa Cruz), FLK-1 (mouse monoclonal, BD Bioscience), CD34, CD45, CD11b (mouse monoclonal, Santa Cruz), alpha-smooth muscle actin (mouse monoclonal, Sigma), and CD8 (rabbit monoclonal Abcam), were diluted to 10 μg/ml in PBS and incubated overnight at 4° C. Slides were washed with three changes of PBS with 0.05% Tween-20 between steps. Appropriate secondary antibodies conjugated to either FITC or Texas Red (Jackson Immunoresearch) were diluted 1:250 and incubated for one hour. The slides were mounted with DAPI-containing mounting medium and visualized on a Nikon Eclipse TE200 fluorescent microscope.

Example 7—G6PDH Assay

Media was harvested daily from the bioreactor and stored at −20° C. On the day of the assay, samples were thawed and, following the manufacturer's instructions, G6PDH activity was quantified using the Vybrant Cytotoxicity Assay Kit (Invitrogen).

Example 8—TUNEL

After seven days of culture, re-endothelialized constructs were fixed with formalin, cut into four representative short axis views from the base to the apex, paraffin embedded, and then sectioned. The DeadEnd Colorimetric TUNEL system (Promega) was used to stain for nicked DNA. The manufacturer's directions for paraffin-embedded samples were followed with the following modifications: after the samples were deparaffinized and rehydrated through an ethanol series, they were microwaved for 2 min in a 10 mM citrate buffer solution (trater et al., 1995, *Histochem. Cell Biol.*, 103(2):157-60); and instead of using horseradish-peroxidase conjugated to streptavidin, samples were treated with a DyLight 594-conjugated streptavidin (Jackson ImmunoResearch). Slides were mounted with Vectashield containing DAPI (Vectorlabs) and imaged using a Nikon Eclipse TE200 inverted microscope (Fryer Co. Inc., Huntley, Ill.).

Example 9—In Vitro Thrombomodulin Assay

The thrombomodulin assay was adapted from previously published work (Calnek & Grinnell, 1998, Experimen. Cell Res., 238(1):294-8; Ibrahim & Ramamurthi, 2008, *J. Tissue Eng. Regen. Med.*, 2(1):22-32). On the last day of culture (day seven), constructs were washed three times with phenol red-free DMEM/F12 (Invitrogen) at a flow rate of 1 mL/min for a total of 45 minutes. Four milliliters of phenol-red free DMEM/F12 containing human alpha-thrombin (0.1 NIH U/mL; Haematologic Technologies) and human protein C (12 µg/mL; Haematologic Technologies) was then continuously circulated through the heart constructs via the aorta for 45 min at 1 ml/min. In triplicate, 100 µL of media was transferred to a 96-well plate, mixed with 50 µL of hirudin stock (12 ATU/mL; American Diagnostica) and incubated for 5 min at 37° C. To each sample-containing well, 50 µL of the substrate S-2366 (final concentration 0.75 mM; Chromogenix) was added and incubated at room temperature for 5 min. The absorbance at 410 nm and 490 nm was measured using a Sprectra MAX 340 (Molecular Devices). The final relative absorbance was calculated by subtracting the absorbance at 490 nm from 410 nm and then normalized by acellular scaffold controls.

Example 10—Heterotopic Transplant

Recipient rats, RNU nude (213-388 g) or Fisher 344 (278-351 g) were anesthetized with sodium pentobarbital (60 mg/Kg of body weight, intraperitoneal injection). A mid-line incision in the abdominal wall was used to expose the descending aorta and inferior vena cava. An end-to-side anastomosis of the donor heart's ascending aorta and left pulmonary artery to the recipient rat's abdominal aorta and vena cava was performed with 9-0 suture following Ono & Lindsey (Ono, 1969, *J. Thorac. Cardiovasc. Surg.*, 57(2):225-9). Rats were pre-heparinized before transplant, with nude matrix-only transplants receiving continued anticoagulative therapy (sodium heparin at 100 i.u. per Kg body weight twice on day of transplant, 200 i.u per Kg body weight, subcutaneous for the next 2 days) and coumadin (0.25 mg/Kg body weight/Day) in drinking water.

Example 11—Perfusion and Distribution of Rat Aortic Endothelial Cells

Three recellularization methods were explored to determine the optimal technique for endothelial cell delivery: (a) direct perfusion of the RAECs via the aorta. (b) cell perfusion through the BA with media flow through the aorta, or (c) a combined delivery of cells: first via the IVC followed by a second infusion via the BA as described. After delivery, constructs were cultured under retrograde aortic perfusion of media for one week before being analyzed. To ascertain the localization of the cells and quantify the cellularity after seven days of culture, constructs were fixed, sectioned into 4 short axis views distributed from base to apex, paraffin embedded, stained and the DAPI positive nuclei quantified (FIG. 1A). In each delivery method, cells were retained within the construct and lined vessel lumens. A statistically significant difference was not seen in the number of endothelial cells in the matrix when 20 million cells were delivered via the aorta or the BA (FIG. 1A). However, cells delivered via the aorta did not achieve a uniform distribution throughout the heart, but instead, localized to the apex while the base of the heart remained acellular. A statistically significant increase in the quantified cellularity was observed when the cell seeding number was doubled. The greatest cellularity was observed with IVC- and BA-seeded constructs, which was statistically significant even compared to a single BA infusion of the same cell number.

Figure 1B:
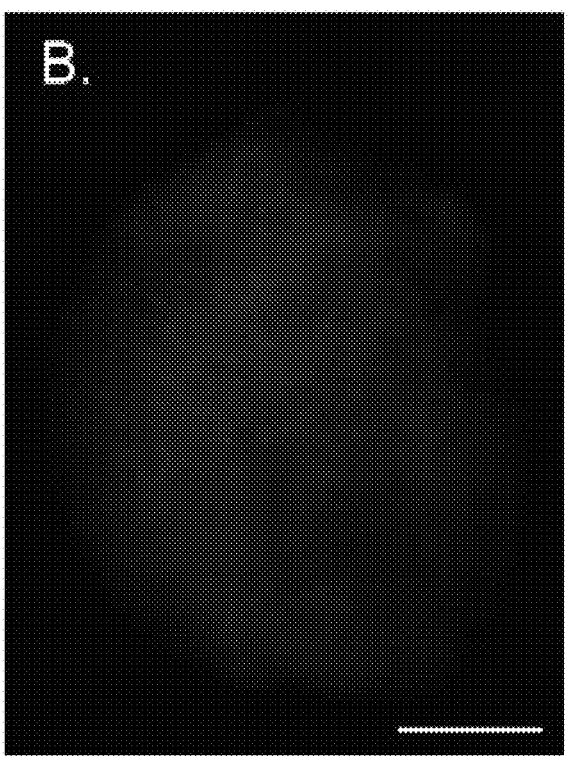
Figure 1C:
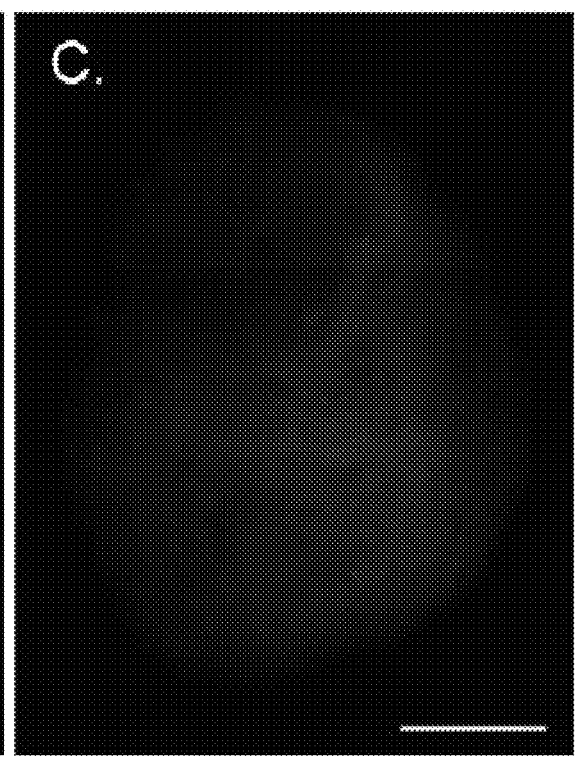
Figure 1D:
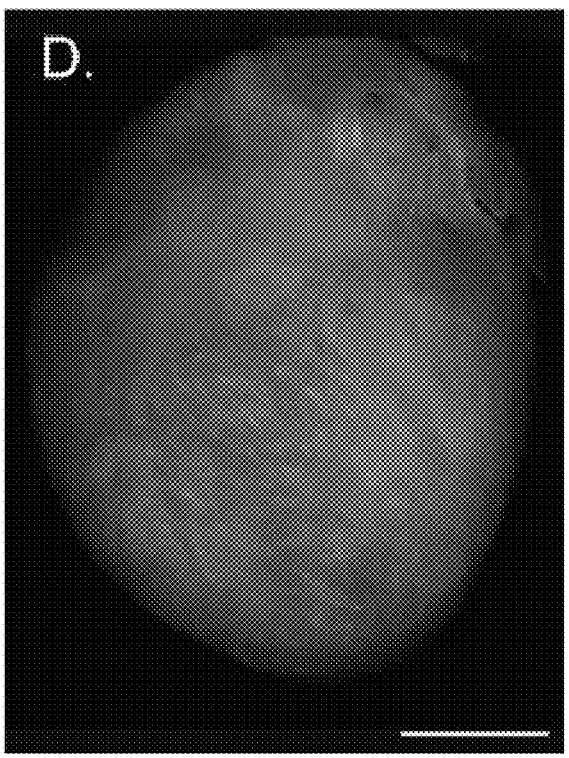
Figure 1E:
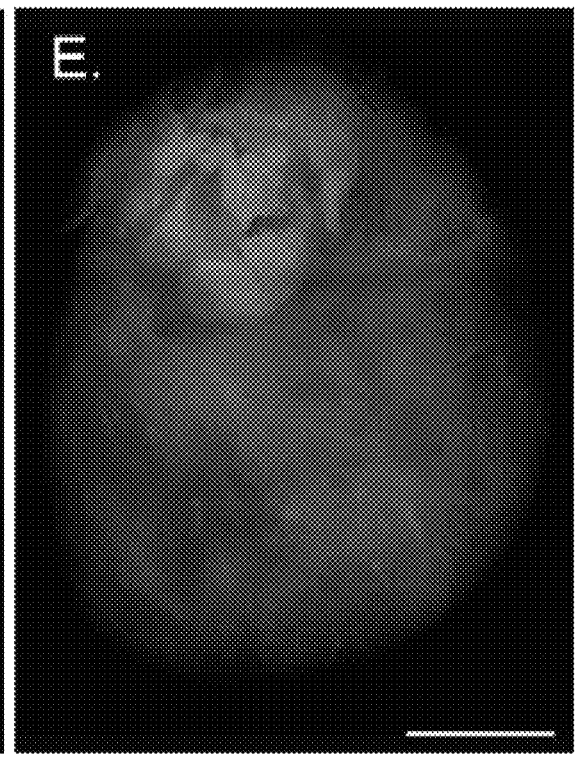
Figure 2A:
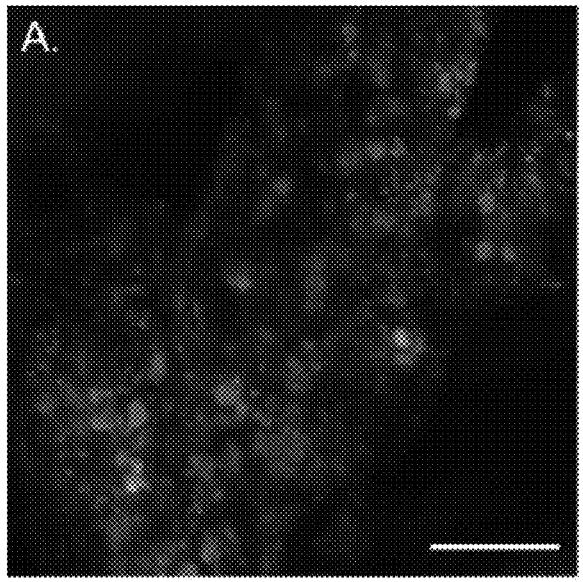
FIGS. 2A-2E are photographs in which 20 million DiO (GREEN) labeled RAECs were delivered via the IVC and 20 million DiI (RED) RAECs were delivered via the BA and visualized seven days after seeding into decellularized scaffolds (Panels A-E). Labeled RAECs were seen in different distributions in the ventricle walls (Panels A-C) and on the endocardial surface (Panels D-E). DAPI positive nuclei are BLUE (Panels A-E). The scale bar in Panels A-E is 50 microns.
Figure 2B:
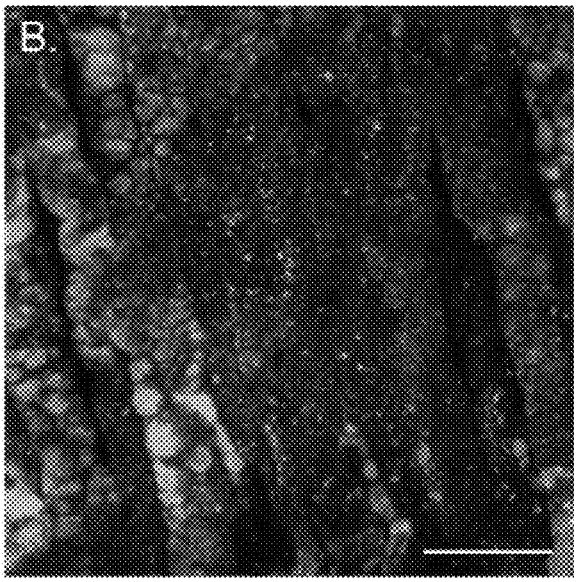
Figure 2C:
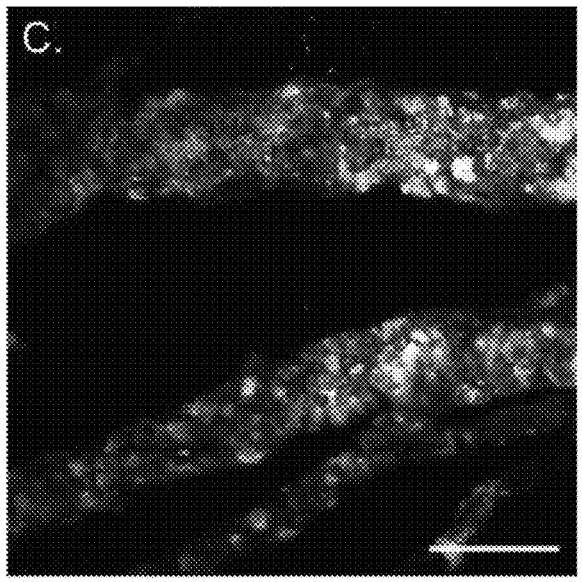
Figure 2D:
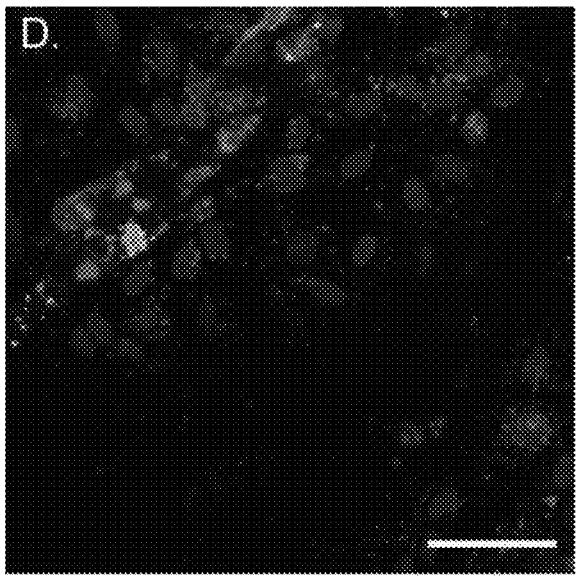
Figure 2E:
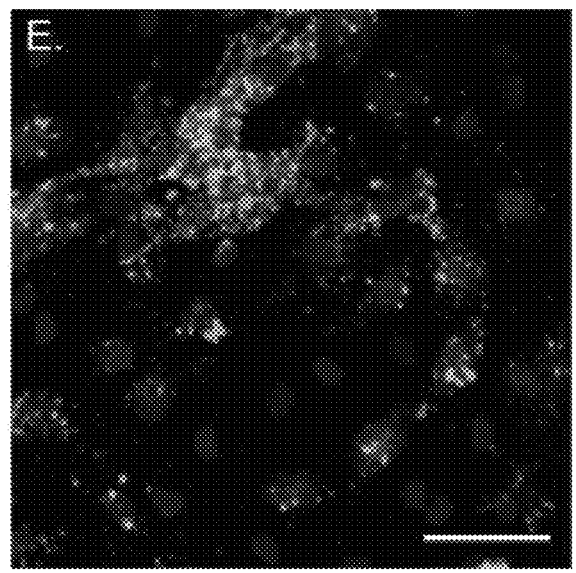

Labeling RAECs with DiI and DiO prior to recellularization confirmed the uniform distribution of cells throughout the heart matrix for constructs that were seeded with cells delivered via the BA (FIG. 1B-C) or IVC plus BA (FIG. 1D-E). Similarly, after IVC RAEC perfusion (DiO positive) cells could be observed throughout the heart from the apex to the base. Examination of constructs with both DiO- and DiI-labeled cell seeding revealed that, in the ventricle wall, vessels could be found that were resurfaced with cells delivered via a single route (FIGS. 2A and B) (i.e., either BA or IVC delivered cells), or containing cells delivered via both routes (FIG. 2C). The endocardial surface of the left ventricle was predominantly recellularized with cells delivered into the BA while the endocardial surface of the right ventricle was relined with RAECs delivered via the IVC (FIGS. 2D and E).

Figure 3A:
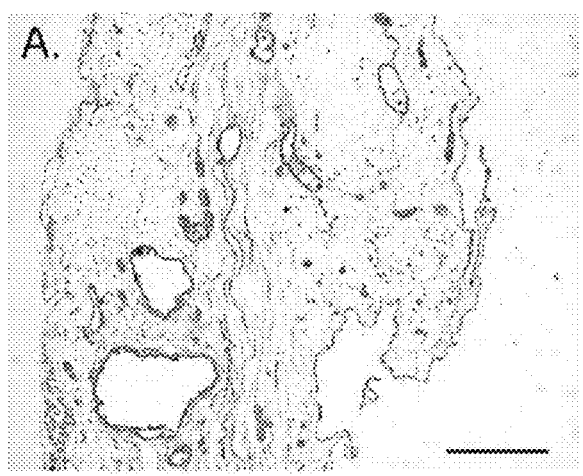
Figure 3B:
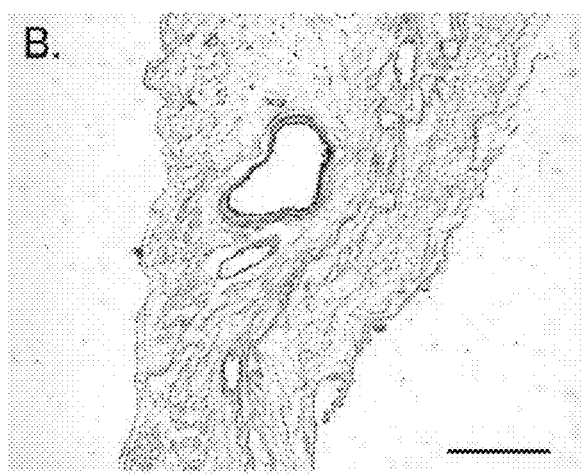

Histology (hematoxylin and eosin and Verhoeff-von Gieson staining) of constructs that were cultured for seven days shows that vessels of varying diameters were relined (FIG. 3A-D), as were both elastin positive arterial vessels and elastin negative vessels (FIGS. 3B and D). These results indicated that RAECs exhibit no observable vessel preference during recellularization and subsequent in vitro culturing. Quantification of vessel diameter within the mid-ventricular wall revealed that the combined delivery of cells via the IVC and BA resulted in a statistically significant increase in the number of small vessels (11 to 25 microns in diameter) than did BA RAEC delivery alone (FIG. 3E). When apical sections were examined, this delivery-dependence in the vessel diameter distribution was not observed.

Example 12—Rat Aortic Endothelial Cell Survival in Culture

Figure 4A:
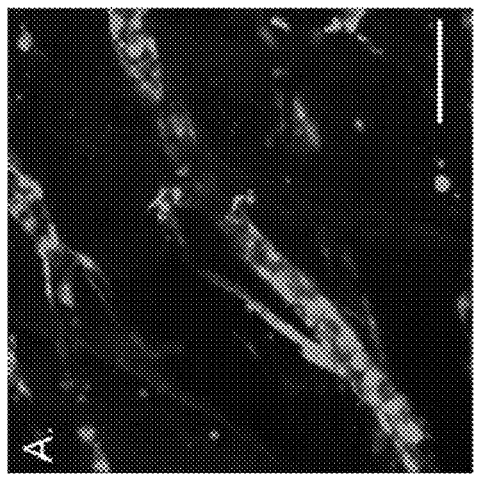
Figure 4B:
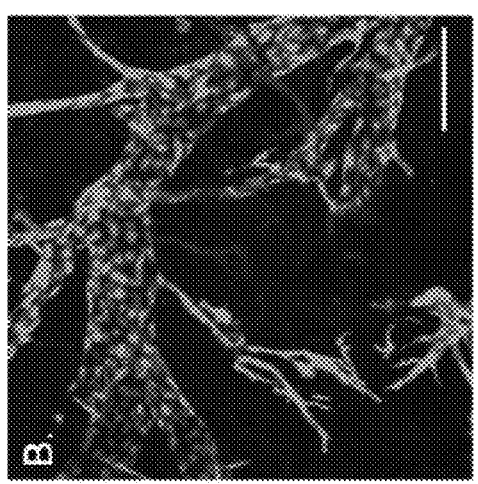
Figure 4C:
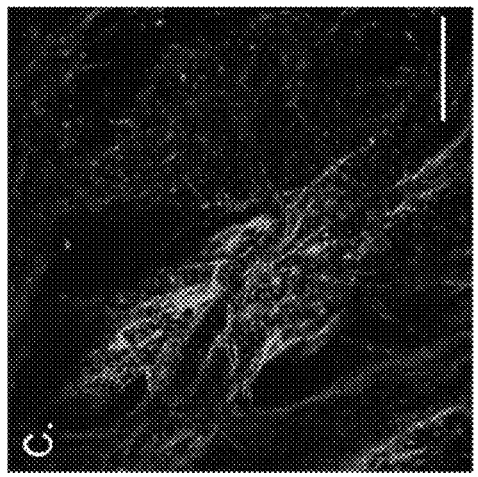
Figure 4D:
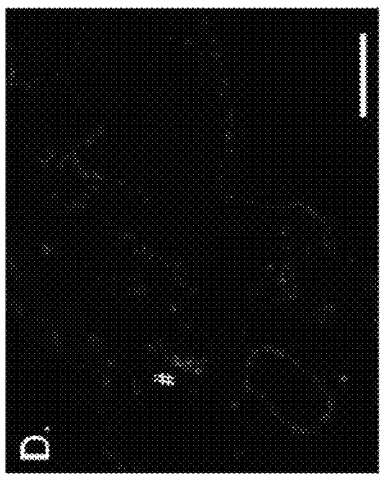
Figure 4E:
Figure 4F:
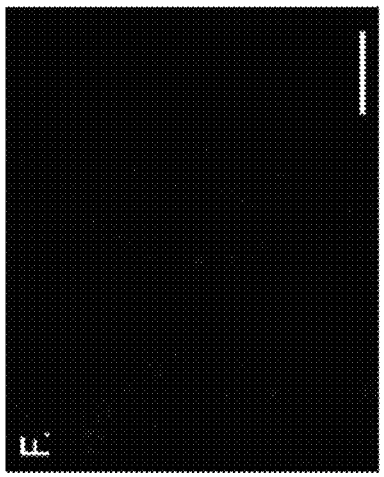
Figure 4J:
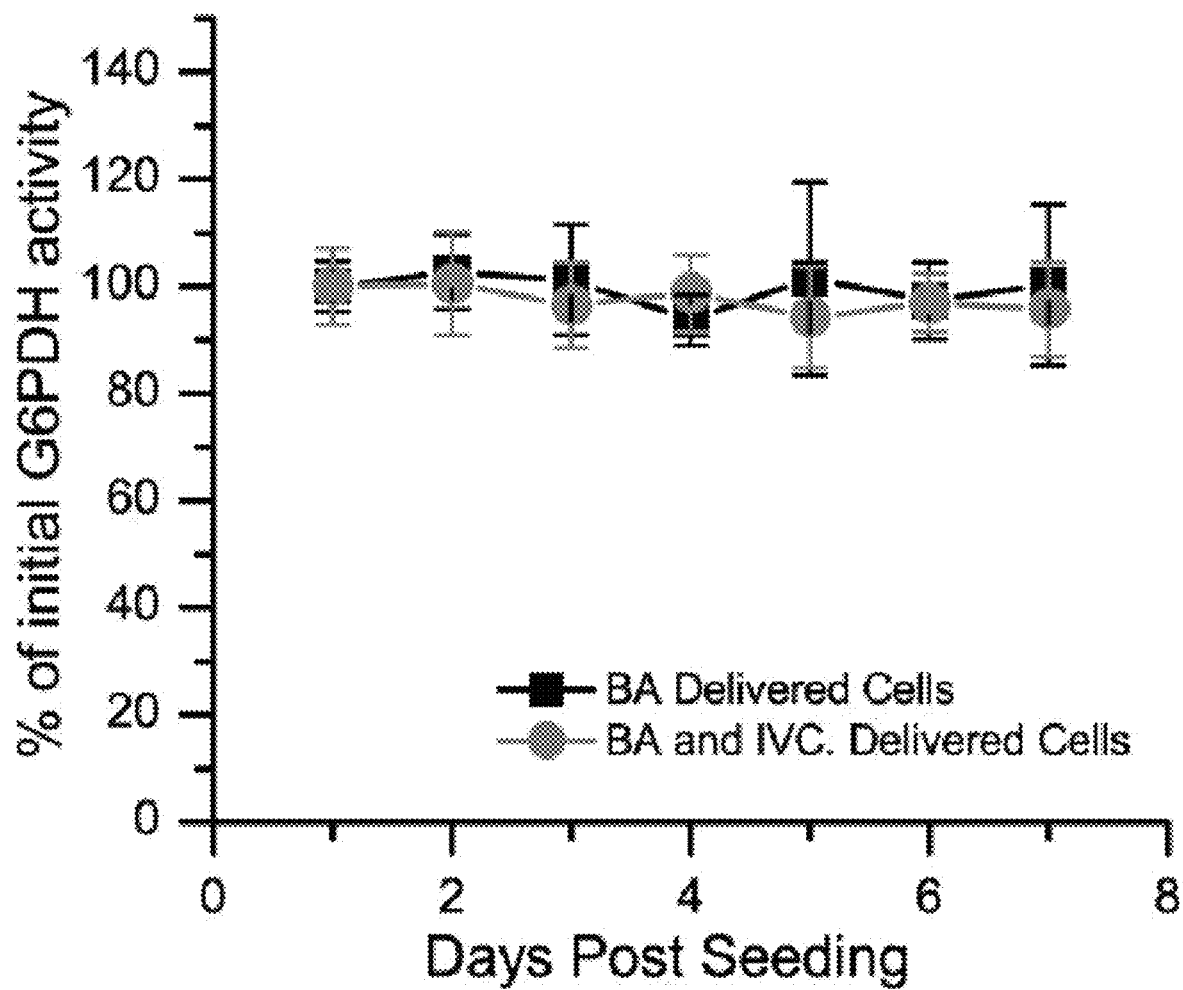

To ascertain whether or not retrograde perfusion was sufficient to maintain RAEC phenotype and prevent cell death in recellularized constructs, three different assays were employed: (a) CMFDA cell labeling at the end of in vitro culture, (b) TUNEL staining, and (c) quantification of glucose-6-phosphate dehydrogenase (G6PDH) activity in the construct perfusate over a seven day period. Constructs were recellularized, either via the BA or the IVC alone, cultured for seven days as described, and then CMFDA-labeled. CMFDA was used since it can only label and be cleaved by viable cells. Both BA- and IVC-delivered cells were capable of cleaving CMFDA (FIG. 4A-C) at day seven. Endocardial cells lining the right ventricle were labeled (FIG. 4C), indicating rudimentary coronaries. TUNEL analysis showed that very few, if any, RAEC were apoptotic on day seven (FIG. 4D-I), regardless of cell location (LV, RV or septum). As an indicator of ongoing cell death, G6PDH activity was quantified. No increase was observed in the G6PDH for the duration of the experiment, regardless of the cell delivery method (FIG. 4J). These results indicate that aortic perfusion is sufficient to maintain RAECs throughout a recellularized heart construct regardless of how they were delivered.

Example 13—In Vitro Phenotypic Analysis of Re-Endothelialized Constructs

Figure 5A:
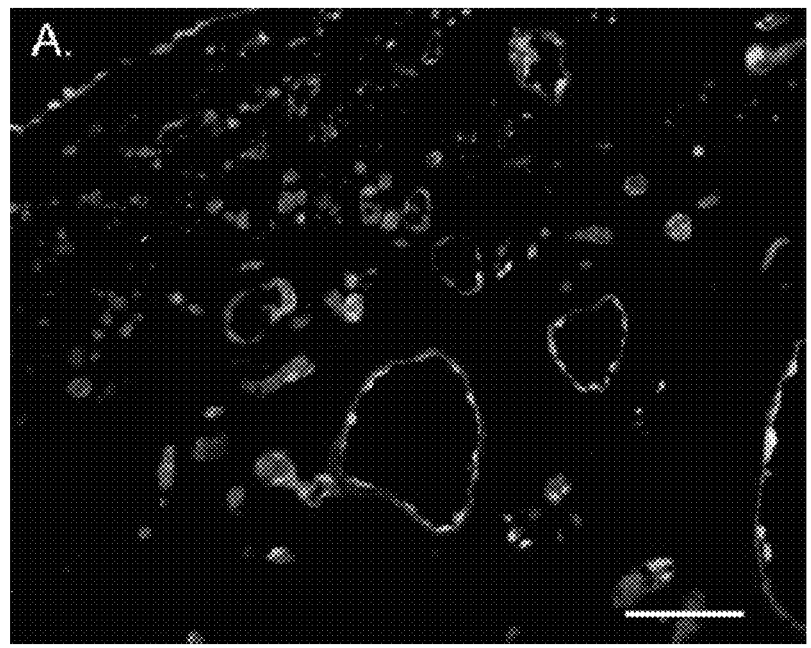
Figure 5B:
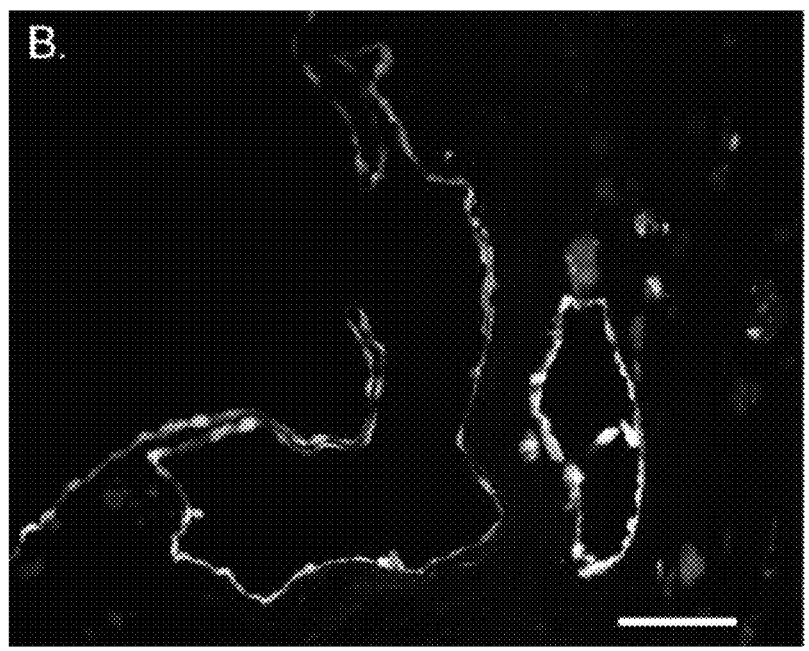
Figure 5C:
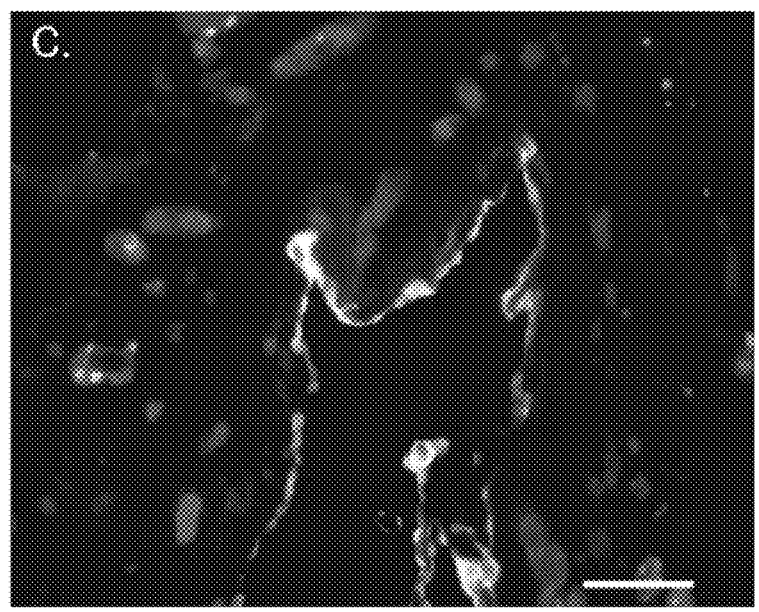
Figure 5D:
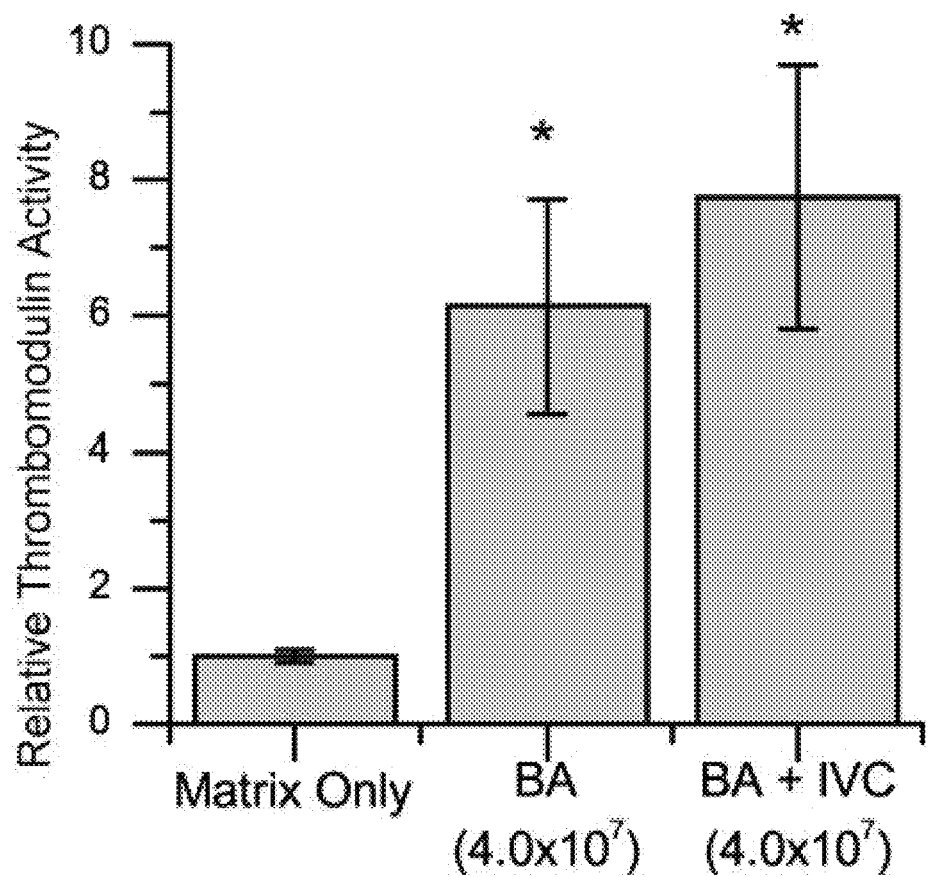
Figure 7A:
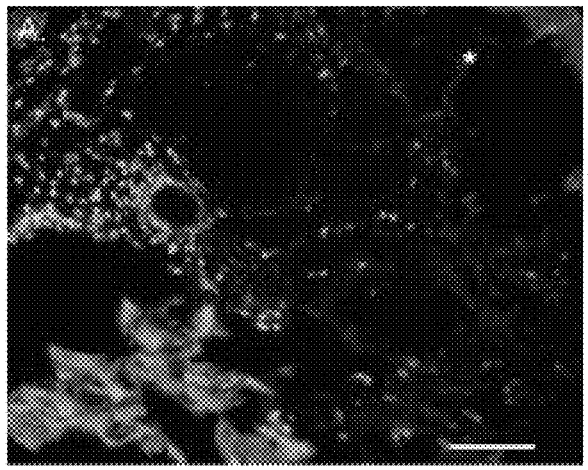
Figure 7B:
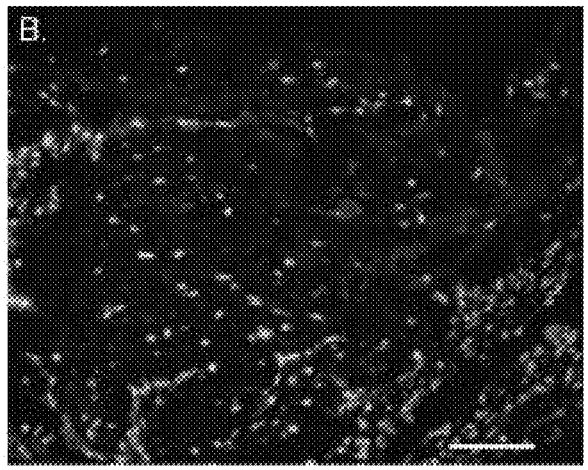
Figure 7C:
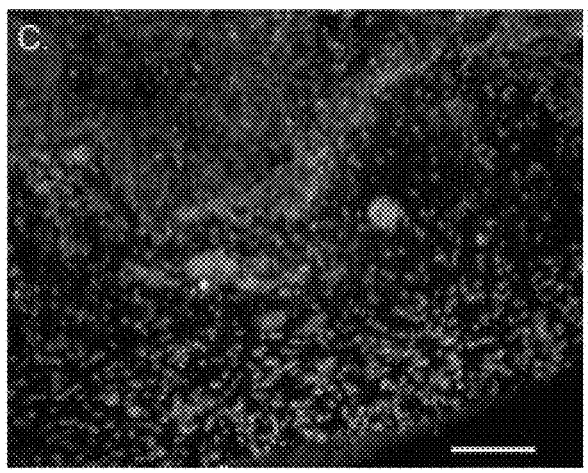
Figure 7D:
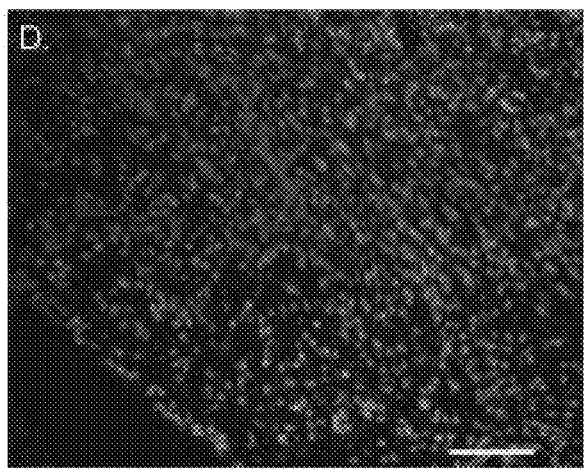

RAEC phenotype and function was examined by immunofluorescent staining of cells in the constructs at day seven post-recellularization. Throughout the constructs, PCNA$^+$ cells could be found, suggesting that proliferation was continuing (FIG. 5A). Likewise, eNOS$^+$ cells could be found throughout the vascular tree, implying that the cells remain functional (FIG. 5B). Lastly, RAECs expressed Von Willebrand factor (FIG. 5C), indicating the potential for regulating coagulation. To determine whether or not re-endothelialized constructs were capable of inhibiting the coagulation pathway, an in vitro thrombomodulin assay was performed on perfusate circulating through the construct. To do so, on day seven, a solution containing thrombin and protein C was circulated through recellularized constructs or acellular scaffolds. A statistically significant 6- to 8-fold increase in thrombomodulin and thrombin-mediated protein C activity was seen (FIG. 5D). Protein C is a negative regulator of the coagulation cascade; thus, these results indicate that the recellularized constructs can potentially inhibit the coagulation cascade since they retain the capacity for activating protein C. BA- and BA plus IVC-recellularized constructs performed similarly, though there was a trend towards BA plus IVC cell delivered constructs performing better.

Example 14—Characterization of Heterotopic Explants

Both acellular scaffolds and BA RAEC re-endothelialized constructs were heterotopically transplanted into the abdomen of recipient rats. Prior to transplant, re-endothelialized contructs were cultured for seven days to allow for RAEC attachment and growth. On day seven after transplant, constructs were explanted and examined (FIG. 6). A clot formed in the aorta but was reduced in the recellularized constructs (FIGS. 6A and E). Examination of the LV wall and ventricle showed greater thrombogenesis in the acellular scaffold transplants compared to re-endothelialized constructs (FIGS. 6B and F). More loose blood was observed in the parenchyma of the acellular scaffolds (FIGS. 6C and G) while patent vessels filled with blood were observed in re-endothelialized constructs (FIGS. 6D and I). Characterization of recruited cells by immunofluorescent staining (Table 1) showed that very few (less than 4%) were positive for macrophage (CD11b) or lymphocyte (CD8) markers. In addition, smooth muscle (SMA), mesothelium (calrentinin), endothelial progenitor (CD34), endotheilial (vWF) and fibroblast (vimentin) markers were only expressed by a small subset of the recruited cells (Table 1). The majority of recruited cells expressed the cell markers PECAM$^+$ and VEGFR2$^+$ regardless of whether the construct was recellularized or not (FIG. 7). However, the progenitor cell markers, CD34 and hematopoietic stem cells (CD45), were only expressed by a small subset of the recruited cells (Table 1).

TABLE 1

| Marker | Positive cells per high power field | % of DAPI positive nuclei |
|---|---|---|
| CD11b | 44.00 | 3.87 |
| CD45 | 22.50 | 2.37 |
| CD8 | 23.20 | 0.89 |
| Calretinin | 20.00 | 1.69 |
| CD34 | 6.00 | 0.13 |
| vWF | 19.00 | 1.11 |
| Vimentin | 17.80 | 0.39 |
| SMA | 3.20 | 0.09 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An ex vivo method of reendothelializing a mammalian tissue or organ matrix, comprising the steps of: a) providing a perfusion decellularized mammalian tissue or organ matrix perfused with a physiological buffer under pressure; and b) reendothelializing the perfusion decellularized mammalian tissue or organ matrix by perfusing, antegrade and retrograde, the decellularized mammalian tissue or organ matrix with a physiological composition comprising a substantially pure population of mammalian endothelial cells or mammalian endothelial progenitor cells, wherein the reendothelialization of the decellularized mammalian tissue or organ matrix after perfusing the composition having the cells antegrade and retrograde is enhanced relative to the reendothelialization of a corresponding decellularized mammalian tissue or organ matrix after perfusing a composition having the same number of cells antegrade or retrograde.

2. The method of claim 1, wherein the mammalian endothel cells are selected from the group consisting of blood endothelial cells, bone marrow endothelial cells, circulating endothelial cells, human aorta endothelial cells, human brain microvascular endothelial cells, humandermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, liver sinusoidal endothelial cells, colony forming unit-endothelial cells (CFU-ECs), circulating angiogenic cells (CACs), circulating endothelial precursors (CEPS), endothelial colony-forming cells (ECFC), low proliferative potential EGFC (LPP-ECFC) high proliferative ECFC (HPP-ECFC), and combinations thereof.

3. The method of claim 1, wherein the mammalian endothelial cells or endothelial progenitor cells are embryonic stem cells (ESCs)- or induced pluripotent stem cells (iPSCs)-derivedendothelial cells or endothelial progenitor cells.

4. The method of claim 1, wherein the mammalian tissue or organ matrix originates from an organ selected from the group consisting of a heart, kidney, liver, lung, pancreas, intestine, muscle, skin, breast, esophagus, trachea, or omentum.

5. The method of claim 1, wherein the mammalian tissue or organ matrix and the mammalian endothelial cells or mammalian endothelial precursor cells are xenogeneic.

6. The method of claim 1, wherein the mammalian tissue or organ matrix and the mammalian endothelial cells or mammalian endothelial precursor cells are allogeneic.

7. The method of claim 1 further comprising introducing mammalian cells other than mammalian endothelial or mammalian endothelial progenitor cells into or onto the mammalian tissue or organ matrix before step b).

8. The method of claim 1 further comprising introducing mammalian cells other than mammalian endothelial or mammalian endothelial progenitor cells into or onto the mammalian tissue or organ matrix after step b).

9. A method of reducing thrombogenesis and immunogenicity in a recellularized mammalian tissue or organ following transplantation into a mammalian recipient, comprising:
a) providing a decellularized mammalian tissue or organ matrix perfused with a physiological buffer under pressure;
b) reendothelializing the decellularized mammalian tissue or organ matrix by perfusing, antegrade and retrograde, the mammalian tissue or organ matrix with a physiological composition comprising an amount of a substantially pure population of mammalian endothelial cells or of mammalian endothelial progenitor cells; and c) transplanting the reendothelialized tissue or organ matrix into the mammalian recipient, wherein the reendothelialized mammalian tissue or organ matrix has reduced thrombogenesis and immunogenicity relative to a corresponding mammalian tissue or organ matrix that is re-endothelialized antegrade or retrograde with the same amount of mammalian endothelial cells or mammalian endothelial progenitor cells.

10. The method of claim 9, wherein the mammalian endothelial cells are selected from the group consisting of blood endothelial cells, bone marrow endothelial cells, circulating endothelial cells, human aorta endothelial cells, human brain microvascular endothelial cells, humandermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, liver sinusoidalendothelial cells, colony forming unit-endothelial cells (CFU-ECs), circulating angiogenic cells (CACs), circulating endothelial precursors (CEPS), endothelial colony-forming cells (ECFC), low proliferative potential ECFC (LPP-ECFC), high proliferative ECFC (HPP-ECFC), and combinations thereof.

11. The method of claim 9, wherein the mammalian endothelial cells or mammalian endothelial progenitor cells are embryonic stem cells (ESCs)- or induced pluripotent stem cells (iPSCs)-derivedendothelial cells or endothelial progenitor cells.

12. The method of claim 9, wherein the mammalian tissue or organ matrix originates from an organ selected from the group consisting of a heart, kidney, liver, lung, pancreas, intestine, muscle, skin, breast, esophagus, trachea, or omentum.

13. The method of claim 9, wherein the mammalian tissue or organ matrix and the mammalian endothelial cells or mammalian endothelial precursor cells are xenogeneic.

14. The method of claim 9, wherein the mammalian tissue or organ matrix and the mammalian endothelial cells or mammalian endothelial precursor cells are allogeneic.

15. The method of claim 9, wherein the mammalian tissue or organ matrix is xenogeneic to the recipient and wherein mammalian endothelial cells or mammalian endothelial progenitor cells are allogeneic to the recipient.

16. The method of claim 9 further comprising introducing mammalian cells other than mammalian endothelial or mammalian endothelial progenitor cells into or onto the mammalian tissue or organ matrix before step b).

17. The method of claim 9 further comprising introducing mammalian cells other than mammalian endothelial or mammalian endothelial progenitor cells into or onto the mammalian tissue or organ matrix after step b).

18. The method of claim 9 further comprising introducing mammalian cells other than mammalian endothelial cells or mammalian endothelial progenitor cells into or onto the mammalian tissue or organ matrix after step c).

19. The method of claim 16, wherein the mammalian cells other than mammalian endothelial cells or mammalian endothelial progenitor cells are introduced to the mammalian tissue or organ matrix via perfusion, direct injection, topical application, or combinations thereof.

20. The method of claim 9, wherein the provided mammalian tissue or organ matrix is perfusion decellularized.

21. The method of claim 17, wherein the mammalian cells other than mammalian endothelial cells or mammalian endothelial progenitor cells are introduced to the mammalian tissue or organ matrix via perfusion, direct injection, to topical application, or combinations thereof.

* * * * *

UNITED STATES PATENT AND TRADEMARK OFFICE
CERTIFICATE OF CORRECTION

PATENT NO. : 11,414,644 B2
APPLICATION NO. : 16/260997
DATED : August 16, 2022
INVENTOR(S) : Taylor et al.

It is certified that error appears in the above-identified patent and that said Letters Patent is hereby corrected as shown below:

On the Title Page

On page 2, in Column 1, item (56) under "U.S. Patent Documents", Line 26, delete "2007/0002061" and insert --2007/0020610-- therefor On page 4, in Column 1, item (56) under "Other Publications", Line 42, delete ""Austrialian" and insert --"Australian-- therefor On page 4, in Column 1, item (56) under "Other Publications", Line 44, delete ""Austrialian" and insert --"Australian-- therefor On page 7, in Column 1, item (56) under "Other Publications", Line 37, delete "Human Human" and insert --Human-- therefor On page 7, in Column 1, item (56) under "Other Publications", Line 37, delete "Celis" and insert --Cells-- therefor On page 7, in Column 1, item (56) under "Other Publications", Line 40, delete "gtransplantation" and insert --transplantation-- therefor On page 8, in Column 1, item (56) under "Other Publications", Line 35, delete "decellurized" and insert --decellularized-- therefor On page 9, in Column 1, item (56) under "Other Publications", Line 68, delete "signais" and insert --signals-- therefor On page 9, in Column 2, item (56) under "Other Publications", Line 5, delete "Determinatino"," and insert --Determination",-- therefor Signed and Sealed this
Twenty-second Day of November, 2022

Katherine Kelly Vidal
*Director of the United States Patent and Trademark Office*

CERTIFICATE OF CORRECTION (continued)
U.S. Pat. No. 11,414,644 B2

On page 10, in Column 1, item (56) under "Other Publications", Line 40, delete "ceils"," and insert --cells,"-- therefor On page 10, in Column 2, item (56) under "Other Publications", Line 45, delete "Respomse" and insert --Response-- therefor On page 12, in Column 2, item (56) under "Other Publications", Line 1, delete "EmbryonicStem" and insert --Embryonic Stem-- therefor On page 12, in Column 2, item (56) under "Other Publications", Line 2, delete "CellsExpressing" and insert --Cells Expressing-- therefor In the Specification In Column 2, Line 19, delete "interstial" and insert --interstitial-- therefor In Column 2, Line 27, delete "interstial" and insert --interstitial-- therefor In Column 5, Line 30, delete "eNOS." and insert --eNOS,-- therefor In Column 5, Line 31, delete "DAPI:" and insert --DAPI;-- therefor In Column 6, Line 34, after "Nat", insert --.--

In Column 7, Line 22, delete "supplements." and insert --supplements,-- therefor In Column 7, Line 30, delete "O2," and insert --$O_2$,-- therefor In Column 7, Line 31, delete "CO2;" and insert --$CO_2$;-- therefor In Column 8, Line 53, delete "immunogenicity." and insert --immunogenicity,-- therefor In Column 9, Line 1, delete "bFGF." and insert --bFGF,-- therefor In Column 9, Line 50, delete "Fit-1)," and insert --Flt-1),-- therefor In Column 11, Line 60, delete "VE-cadherin." and insert --VE-cadherin,-- therefor In Column 13, Line 8, delete "$10^4$." and insert --$10^4$,-- therefor In Column 14, Line 49, delete "type 1," and insert --type I,-- therefor In Column 14, Line 65, delete "Lime" and insert --time-- therefor In Column 17, Line 14, delete "(Ou" and insert --(Ott-- therefor

CERTIFICATE OF CORRECTION (continued)
U.S. Pat. No. 11,414,644 B2

In Column 19, Line 64, delete "aorta." and insert --aorta,-- therefor

In the Claims

In Column 22, Line 66, in Claim 2, delete "endothel" and insert --endothelial-- therefor In Column 23, Line 15, in Claim 2, delete "(CEPS)," and insert --(CEPs),-- therefor In Column 23, Line 16, in Claim 2, delete "EGFC (LPP-ECFC)" and insert --ECFC (LPP-ECFC),-- therefor In Column 24, Line 15, in Claim 10, delete "(CEPS)," and insert --(CEPs),-- therefor In Column 24, Line 60, in Claim 21, after "injection,", delete "to"